(12) United States Patent
Hara et al.

(10) Patent No.: US 7,736,876 B2
(45) Date of Patent: *Jun. 15, 2010

(54) PEPTIDE-FORMING ENZYME GENE

(75) Inventors: Seiichi Hara, Kawasaki (JP); Kenzo Yokozeki, Kawasaki (JP); Isao Abe, Kawasaki (JP); Naoto Tonouchi, Kawasaki (JP); Yasuko Jojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/141,428

(22) Filed: Jun. 18, 2008

(65) Prior Publication Data

US 2008/0274530 A1 Nov. 6, 2008

Related U.S. Application Data

(60) Division of application No. 11/841,151, filed on Aug. 20, 2007, which is a division of application No. 10/855,533, filed on May 28, 2004, now Pat. No. 7,288,389, which is a continuation of application No. PCT/JP03/09468, filed on Jul. 25, 2003.

(30) Foreign Application Priority Data

Jul. 26, 2002 (JP) ............................. 2002-218957
Jan. 24, 2003 (JP) ............................. 2003-016765

(51) Int. Cl.
  *C12P 21/06* (2006.01)
  *C12N 9/00* (2006.01)
  *C12N 1/20* (2006.01)
  *C12N 15/00* (2006.01)
  *C07H 21/04* (2006.01)

(52) U.S. Cl. .................... 435/183; 435/69.1; 435/252.3; 435/320.1; 536/23.2

(58) Field of Classification Search ....................... None
See application file for complete search history.

(56) References Cited

U.S. PATENT DOCUMENTS

| 7,288,389 | B2 * | 10/2007 | Hara et al. ................... 435/68.1 |
| 7,338,780 | B2 * | 3/2008 | Yokozeki et al. ............ 435/68.1 |
| 7,361,458 | B2 * | 4/2008 | Yokozeki et al. ............ 435/4 |
| 2004/0204577 | A1 | 10/2004 | Hara et al. |
| 2008/0050773 | A1 | 2/2008 | Hara et al. |
| 2008/0166761 | A1 | 7/2008 | Hara et al. |

FOREIGN PATENT DOCUMENTS

| EP | 0 278 787 | 8/1988 |
| EP | 0 359 399 | 3/1990 |
| JP | 53-92729 | 8/1978 |
| JP | 1-96194 | 4/1989 |
| JP | 6-234715 | 8/1994 |
| JP | 2000-78971 | 3/2000 |
| WO | WO 90/01555 | 2/1990 |
| WO | WO 99/61050 | 12/1999 |
| WO | WO 00/58478 | 10/2000 |
| WO | WO 01/70937 A1 | 9/2001 |
| WO | WO 03/010187 | 2/2003 |
| WO | WO 03/010189 | 2/2003 |
| WO | WO 03/010307 | 2/2003 |

OTHER PUBLICATIONS

S. Akabori, et al., "Protection of Amide-Nitrogen for Peptide Synthesis. A Novel Synthesis of Peptides Containing C-Terminal Glutamine", Bull. Chem. Soc. Jpn., 34, May 1961, p. 739.
Y. Shimonishi, et al., "Studies on the Synthesis of Peptides Containing Glutamine as the C-Terminal. I. Protection of Amide-Nitrogen With Xanthyl Group During Peptide Synthesis", Bull. Chem. Soc. Jpn., vol. 35, No. 12, Dec. 1962, pp. 1966-1970.
Y. Shimonishi, "Studies of the Synthesis of Peptides Containing C-Terminal Glutamine. II. The Synthesis and Use of Alpha-P-Nitrobenzyl Gamma-Methyl L-Glutamate", Bull. Chem. Soc. Jpn., vol. 37, No. 2, Feb. 1964, pp. 200-203.
K. Morihara, et al., "Alpha-Chymotrypsin as the Catalyst for Peptide Synthesis", Biochem. J., 1977, 163, pp. 531-542.
F. Krieg, et al., "Enzymatic Peptide Synthesis by the Recombinant Proline-Specific Endopeptidase From Flavobacterium Meningosepticum and Its Mutationally Altered CYS-556 Variant", Appl Microbiol Biotechnol, 1995, 42, pp. 844-852.
P. Vandamme, et al., "New Perspectives in the Classification of the Flavobacteria: Description of Chryseobacterium Gen. Nov., Bergeyella Gen. Nov., and Empedobacter Nom. Rev.", International Journal of Systematic Bacteriology, vol. 44, No. 4, Oct. 1994, pp. 827-831, XP-009050959.
J.J. Polderman-Tijmes, et al., "Cloning Sequence Analysis, and Expression in *Escherichia coli* of the Gene Encoding an Alpha-Amino Acid Ester Hydrolase From Acetobacter Turbidans", Applied and Enviromental Microbiology, vol. 68, No. 1, Jan. 2002, pp. 211-218, XP-001121414.
Guo, et al. Protein tolerance to random amino acid change, PNAS, 101/25, 9205-9210, 2004.

* cited by examiner

*Primary Examiner*—Christian L Fronda
(74) *Attorney, Agent, or Firm*—Oblon, Spivak, McClelland, Maier & Neustadt, L.L.P.

(57) ABSTRACT

DNA and recombinant DNA that encode a peptide-forming enzyme, a method for producing a peptide-forming enzyme, and a method for producing a dipeptide are disclosed. A method for producing a dipeptide includes producing a dipeptide from a carboxy component and an amine component by using a culture of a microbe belonging to the genus *Sphingobacterium* and having the ability to form the dipeptide from the carboxy component and the amine component, a microbial cell separated from the culture, treated microbial cell product of the microbe or a peptide-forming enzyme derived from the microbe.

14 Claims, 4 Drawing Sheets

■ : L-Ala-L-Gln PRODUCED IN ENZYME - ADDED LOT
× : RESIDUAL L-Ala-OMe IN ENZYME - ADDED LOT
▲ : L-Ala-L-Gln PRODUCED IN ENZYME - NON - ADDED LOT

```
                        SEQUENCE LISTING

<160> NUMBER OF SEQ ID NOS: 27

<210> SEQ ID NO 1
<211> LENGTH: 9
<212> TYPE: PRT
<213> ORGANISM: Empedobacter brevis

<400> SEQUENCE: 1

Leu Phe Thr Ala Ile Tyr Gln Pro Lys
1               5

<210> SEQ ID NO 2
<211> LENGTH: 9
<212> TYPE: PRT
<213> ORGANISM: Empedobacter brevis

<400> SEQUENCE: 2

Thr Asn Val Thr Tyr Thr Met Pro Asp
1               5

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (9)..(9)
<223> OTHER INFORMATION: n = a, c, g, or t

<400> SEQUENCE: 3
ttyacngcna thtaycarcc                                               20

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = a, c, g, or t
<220> FEATURE:
<221> NAME/KEY: misc_feature
<222> LOCATION: (9)..(9)
```

-continued

```
<223> OTHER INFORMATION: n = a, c, g, or t
<220> FEATURE:
<221> NAME/KEY: misc_feature
<222> LOCATION: (15)..(15)
<223> OTHER INFORMATION: n = a, c, g, or t
<220> FEATURE:
<221> NAME/KEY: misc_feature
<222> LOCATION: (18)..(18)
<223> OTHER INFORMATION: n = a, c, g, or t

<400> SEQUENCE: 4
tcnggcatng trtangtnac rtt                                             23

<210> SEQ ID NO 5
<211> LENGTH: 2024
<212> TYPE: DNA
<213> ORGANISM: Empedobacter brevis
<220> FEATURE:
<221> NAME/KEY: CDS
<222> LOCATION: (61)..(1908)
<223> OTHER INFORMATION:

<400> SEQUENCE: 5
atttcttaat aaaaactgaa atcttaatac atttatacta tcgtaaaatt tattgaacac     60 gtg aaa aaa tta aca tta aaa gta act cta ctt aca ctt ttg ttg gga     108
Val Lys Lys Leu Thr Leu Lys Val Thr Leu Leu Thr Leu Leu Leu Gly
1               5                   10                  15 agt aca gtt gga ttt gcg caa gat gca aaa gca gat tct gct tat gtg    156
Ser Thr Val Gly Phe Ala Gln Asp Ala Lys Ala Asp Ser Ala Tyr Val
                20                  25                  30 cgc gac aat tac gaa aaa ata gaa caa gta att ccg atg cgc gat ggt    204
Arg Asp Asn Tyr Glu Lys Ile Glu Gln Val Ile Pro Met Arg Asp Gly
            35                  40                  45 aca aag tta ttt aca gct att tat cag cca aaa gat aaa aca aaa caa    252
Thr Lys Leu Phe Thr Ala Ile Tyr Gln Pro Lys Asp Lys Thr Lys Gln
        50                  55                  60 tat ccc gtt ttg tta aat cgt acg cct tat aca gtt gcg cct tat ggt    300
Tyr Pro Val Leu Leu Asn Arg Thr Pro Tyr Thr Val Ala Pro Tyr Gly
65                  70                  75                  80 gta aat gaa tac aag aaa tcg tta gga aat ttt cct aca gaa atg cgc    348
Val Asn Glu Tyr Lys Lys Ser Leu Gly Asn Phe Pro Thr Glu Met Arg
                85                  90                  95 gaa ggt ttt att ttt gtt tac caa gat gtg aga gga aaa tgg atg agc    396
Glu Gly Phe Ile Phe Val Tyr Gln Asp Val Arg Gly Lys Trp Met Ser
            100                 105                 110 gaa ggc gaa ttt gaa gat gtt cga cct ata aat cct tca aaa agt aaa    444
Glu Gly Glu Phe Glu Asp Val Arg Pro Ile Asn Pro Ser Lys Ser Lys
        115                 120                 125 aag gca att gac gaa agc aca gat aca ttt gat acg cta gaa tgg ctt    492
Lys Ala Ile Asp Glu Ser Thr Asp Thr Phe Asp Thr Leu Glu Trp Leu
    130                 135                 140 gct aaa aac ttg aag aat tac acg aaa aaa gct gga att tat gga att    540
Ala Lys Asn Leu Lys Asn Tyr Thr Lys Lys Ala Gly Ile Tyr Gly Ile
145                 150                 155                 160 tcg tat cct ggt ttt tat tcg aca atg agt ttg gtt aat tcg cat cca    588
Ser Tyr Pro Gly Phe Tyr Ser Thr Met Ser Leu Val Asn Ser His Pro
                165                 170                 175 act cta aaa gcc gtt tcg cca caa gcg ccc gtt acc aat tgg ttt tta    636
Thr Leu Lys Ala Val Ser Pro Gln Ala Pro Val Thr Asn Trp Phe Leu
            180                 185                 190 ggt gac gat ttt cat cat aat gga gtt tta ttc ttg aat gat tct ttc    684
Gly Asp Asp Phe His His Asn Gly Val Leu Phe Leu Asn Asp Ser Phe
        195                 200                 205
```

| | | |
|---|---|---|
| tca ttt atg act ttt ttt ggt gta aaa cgt ccg caa cca att acg cca<br>Ser Phe Met Thr Phe Phe Gly Val Lys Arg Pro Gln Pro Ile Thr Pro<br>210                   215                   220 | | 732 |
| gat aaa ggt ccg aaa cgt ttt gaa tat cca ata aaa gat aat tat aga<br>Asp Lys Gly Pro Lys Arg Phe Glu Tyr Pro Ile Lys Asp Asn Tyr Arg<br>225                  230                   235                  240 | | 780 |
| ttt tat gca agt ggc tct gta aaa gag ttg aaa gat aaa tat ttg caa<br>Phe Tyr Ala Ser Gly Ser Val Lys Glu Leu Lys Asp Lys Tyr Leu Gln<br>                    245                   250                   255 | | 828 |
| gat aat atc aag ttt tac aat gat tta ttt gcg cat cca gat tac gat<br>Asp Asn Ile Lys Phe Tyr Asn Asp Leu Phe Ala His Pro Asp Tyr Asp<br>260                   265                   270 | | 876 |
| caa ttt tgg caa gat cgt aat gtt tta cca cat tta act aac gtg caa<br>Gln Phe Trp Gln Asp Arg Asn Val Leu Pro His Leu Thr Asn Val Gln<br>                    275                   280                   285 | | 924 |
| cct gct gta atg acg gtt gga ggt ttt ttt gat gca gaa gat gtc tac<br>Pro Ala Val Met Thr Val Gly Gly Phe Phe Asp Ala Glu Asp Val Tyr<br>290                   295                   300 | | 972 |
| ggc gct ttc gaa acg tat aaa gca att gag aaa caa aat ccg aaa gca<br>Gly Ala Phe Glu Thr Tyr Lys Ala Ile Glu Lys Gln Asn Pro Lys Ala<br>305                    310                   315                  320 | | 1020 |
| aca aat att atg gtt gcc gga cct tgg ttt cat ggt ggt tgg gtt cgt<br>Thr Asn Ile Met Val Ala Gly Pro Trp Phe His Gly Gly Trp Val Arg<br>                    325                   330                   335 | | 1068 |
| agc aac gga agt act ttt gga gat atg caa ttt gca tcg aat aca agt<br>Ser Asn Gly Ser Thr Phe Gly Asp Met Gln Phe Ala Ser Asn Thr Ser<br>340                   345                   350 | | 1116 |
| gag cat tat cag caa gaa ata gaa ttg cct ttt ttt aat tat tac tta<br>Glu His Tyr Gln Gln Glu Ile Glu Leu Pro Phe Phe Asn Tyr Tyr Leu<br>                    355                   360                   365 | | 1164 |
| aaa gat aaa ggt aat ttt aaa cca acc gaa gct aca att ttt att acg<br>Lys Asp Lys Gly Asn Phe Lys Pro Thr Glu Ala Thr Ile Phe Ile Thr<br>370                   375                   380 | | 1212 |
| gga tct aac gaa tgg aaa caa ttt gat gct tgg cca cca aaa aat gta<br>Gly Ser Asn Glu Trp Lys Gln Phe Asp Ala Trp Pro Pro Lys Asn Val<br>385                    390                   395                  400 | | 1260 |
| aca aca caa aaa att tat ttg caa caa aat ggt aaa ata gct ttt aat<br>Thr Thr Gln Lys Ile Tyr Leu Gln Gln Asn Gly Lys Ile Ala Phe Asn<br>                    405                   410                   415 | | 1308 |
| aaa acc aat aca aca act act ttt gac gaa tat gtt gca gat cca aat<br>Lys Thr Asn Thr Thr Thr Thr Phe Asp Glu Tyr Val Ala Asp Pro Asn<br>420                   425                   430 | | 1356 |
| tct cca gtt cct tat tca gga gga gtt tta gaa act cgt tca aga gaa<br>Ser Pro Val Pro Tyr Ser Gly Gly Val Leu Glu Thr Arg Ser Arg Glu<br>                    435                   440                   445 | | 1404 |
| tat atg gtc gat gat caa cgc ttt gct tct act cgt cct gat gtt atg<br>Tyr Met Val Asp Asp Gln Arg Phe Ala Ser Thr Arg Pro Asp Val Met<br>450                   455                   460 | | 1452 |
| gtg tat caa tct gat att ttg aca gaa gat att acg ctt gct ggt cct<br>Val Tyr Gln Ser Asp Ile Leu Thr Glu Asp Ile Thr Leu Ala Gly Pro<br>465                    470                   475                  480 | | 1500 |
| gtt atc aat cat tta gtg gtt tct act acg gga aca gac gct gat tat<br>Val Ile Asn His Leu Val Val Ser Thr Thr Gly Thr Asp Ala Asp Tyr<br>                    485                   490                   495 | | 1548 |
| gtt gta aaa ttg att gat gtt tat cct gaa aac acg cca aaa ttt aat<br>Val Val Lys Leu Ile Asp Val Tyr Pro Glu Asn Thr Pro Lys Phe Asn<br>500                   505                   510 | | 1596 |
| aac aaa tta atg gct gga tat caa aat ttg att cgt gca gaa att atg<br>Asn Lys Leu Met Ala Gly Tyr Gln Asn Leu Ile Arg Ala Glu Ile Met | | 1644 |

-continued

```
                515                 520                 525
cgc gga aaa tat aga aat agt ttc tct aac ccc gaa gct atg gtt ccg    1692
Arg Gly Lys Tyr Arg Asn Ser Phe Ser Asn Pro Glu Ala Met Val Pro
    530                 535                 540 aat aaa gaa aca aat gta acg tac acg atg cca gat gtt gga cat aca    1740
Asn Lys Glu Thr Asn Val Thr Tyr Thr Met Pro Asp Val Gly His Thr
545                 550                 555                 560 ttt aag aaa gga cat cgc att atg att caa gtt cag aac agt tgg ttt    1788
Phe Lys Lys Gly His Arg Ile Met Ile Gln Val Gln Asn Ser Trp Phe
                565                 570                 575 cct tta gca gat cgc aat ccg caa caa ttt atg aat gtt tac gaa gca    1836
Pro Leu Ala Asp Arg Asn Pro Gln Gln Phe Met Asn Val Tyr Glu Ala
            580                 585                 590 act tct aaa gat tat tta aaa caa acg caa cga att tat cat act tct    1884
Thr Ser Lys Asp Tyr Leu Lys Gln Thr Gln Arg Ile Tyr His Thr Ser
        595                 600                 605 tat atc gaa att ccg gta ttg aaa taacaaaaaa atccagctaa ttagctggat    1938
Tyr Ile Glu Ile Pro Val Leu Lys
    610                 615 ttttttata atgttacttt tcctattttt cctttatttc caactaaaat tacatatttt    1998
ttatcgggcg aaaccgtaca agtatg                                       2024
```

<210> SEQ ID NO 6
<211> LENGTH: 616
<212> TYPE: PRT
<213> ORGANISM: Empedobacter brevis

<400> SEQUENCE: 6

```
Val Lys Lys Leu Thr Leu Lys Val Thr Leu Leu Thr Leu Leu Leu Gly
1               5                   10                  15

Ser Thr Val Gly Phe Ala Gln Asp Ala Lys Ala Asp Ser Ala Tyr Val
            20                  25                  30

Arg Asp Asn Tyr Glu Lys Ile Glu Gln Val Ile Pro Met Arg Asp Gly
        35                  40                  45

Thr Lys Leu Phe Thr Ala Ile Tyr Gln Pro Lys Asp Lys Thr Lys Gln
    50                  55                  60

Tyr Pro Val Leu Leu Asn Arg Thr Pro Tyr Thr Val Ala Pro Tyr Gly
65                  70                  75                  80

Val Asn Glu Tyr Lys Lys Ser Leu Gly Asn Phe Pro Thr Glu Met Arg
                85                  90                  95

Glu Gly Phe Ile Phe Val Tyr Gln Asp Val Arg Gly Lys Trp Met Ser
            100                 105                 110

Glu Gly Glu Phe Glu Asp Val Arg Pro Ile Asn Pro Ser Lys Ser Lys
        115                 120                 125

Lys Ala Ile Asp Glu Ser Thr Asp Thr Phe Asp Thr Leu Glu Trp Leu
    130                 135                 140

Ala Lys Asn Leu Lys Asn Tyr Thr Lys Lys Ala Gly Ile Tyr Gly Ile
145                 150                 155                 160

Ser Tyr Pro Gly Phe Tyr Ser Thr Met Ser Leu Val Asn Ser His Pro
                165                 170                 175

Thr Leu Lys Ala Val Ser Pro Gln Ala Pro Val Thr Asn Trp Phe Leu
            180                 185                 190

Gly Asp Asp Phe His His Asn Gly Val Leu Phe Leu Asn Asp Ser Phe
        195                 200                 205

Ser Phe Met Thr Phe Phe Gly Val Lys Arg Pro Gln Pro Ile Thr Pro
    210                 215                 220
```

```
Asp Lys Gly Pro Lys Arg Phe Glu Tyr Pro Ile Lys Asp Asn Tyr Arg
225                 230                 235                 240

Phe Tyr Ala Ser Gly Ser Val Lys Glu Leu Lys Asp Lys Tyr Leu Gln
            245                 250                 255

Asp Asn Ile Lys Phe Tyr Asn Asp Leu Phe Ala His Pro Asp Tyr Asp
            260                 265                 270

Gln Phe Trp Gln Asp Arg Asn Val Leu Pro His Leu Thr Asn Val Gln
        275                 280                 285

Pro Ala Val Met Thr Val Gly Gly Phe Phe Asp Ala Glu Asp Val Tyr
    290                 295                 300

Gly Ala Phe Glu Thr Tyr Lys Ala Ile Glu Lys Gln Asn Pro Lys Ala
305                 310                 315                 320

Thr Asn Ile Met Val Ala Gly Pro Trp Phe His Gly Trp Val Arg
                325                 330                 335

Ser Asn Gly Ser Thr Phe Gly Asp Met Gln Phe Ala Ser Asn Thr Ser
            340                 345                 350

Glu His Tyr Gln Gln Glu Ile Glu Leu Pro Phe Phe Asn Tyr Tyr Leu
        355                 360                 365

Lys Asp Lys Gly Asn Phe Lys Pro Thr Glu Ala Thr Ile Phe Ile Thr
    370                 375                 380

Gly Ser Asn Glu Trp Lys Gln Phe Asp Ala Trp Pro Pro Lys Asn Val
385                 390                 395                 400

Thr Thr Gln Lys Ile Tyr Leu Gln Gln Asn Gly Lys Ile Ala Phe Asn
            405                 410                 415

Lys Thr Asn Thr Thr Thr Phe Asp Glu Tyr Val Ala Asp Pro Asn
        420                 425                 430

Ser Pro Val Pro Tyr Ser Gly Gly Val Leu Glu Thr Ser Arg Glu
    435                 440                 445

Tyr Met Val Asp Asp Gln Arg Phe Ala Ser Thr Arg Pro Asp Val Met
450                 455                 460

Val Tyr Gln Ser Asp Ile Leu Thr Glu Asp Ile Thr Leu Ala Gly Pro
465                 470                 475                 480

Val Ile Asn His Leu Val Val Ser Thr Thr Gly Thr Asp Ala Asp Tyr
            485                 490                 495

Val Val Lys Leu Ile Asp Val Tyr Pro Glu Asn Thr Pro Lys Phe Asn
        500                 505                 510

Asn Lys Leu Met Ala Gly Tyr Gln Asn Leu Ile Arg Ala Glu Ile Met
    515                 520                 525

Arg Gly Lys Tyr Arg Asn Ser Phe Ser Asn Pro Glu Ala Met Val Pro
530                 535                 540

Asn Lys Glu Thr Asn Val Thr Tyr Thr Met Pro Asp Val Gly His Thr
545                 550                 555                 560

Phe Lys Lys Gly His Arg Ile Met Ile Gln Val Gln Asn Ser Trp Phe
            565                 570                 575

Pro Leu Ala Asp Arg Asn Pro Gln Gln Phe Met Asn Val Tyr Glu Ala
        580                 585                 590

Thr Ser Lys Asp Tyr Leu Lys Gln Thr Gln Arg Ile Tyr His Thr Ser
    595                 600                 605

Tyr Ile Glu Ile Pro Val Leu Lys
610                 615

<210> SEQ ID NO 7
<211> LENGTH: 40
```

```
<212> TYPE: DNA
<213> ORGANISM: Artificial Sequence
<220> FEATURE:
<223> OTHER INFORMATION: Synthetic DNA

<400> SEQUENCE: 7
gtatcacgag gccctagctg tggtgtcatg gtcggtgatc                              40

<210> SEQ ID NO 8
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8
ttcgggaatt ccatatgata ccctttttac gtgaacttgc                              40

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9
gggaattcca tatgaaaaaa ttaacattaa agtaact                                 38

<210> SEQ ID NO 10
<211> LENGTH: 36
<212> TYPE: DNA
<213> ORGANISM: Artificial Sequence
<220> FEATURE:
<223> OTHER INFORMATION: Synthetic DNA

<400> SEQUENCE: 10
gggggctgca gtacttgtac ggtttcgccc gataaa                                  36

<210> SEQ ID NO 11
<211> LENGTH: 1935
<212> TYPE: DNA
<213> ORGANISM: Sphingobacterium sp.
<220> FEATURE:
<221> NAME/KEY: CDS
<222> LOCATION: (61)..(1917)
<223> OTHER INFORMATION:

<400> SEQUENCE: 11
gaaaccaagt gtaaaattat aatttacacc aaagaatgta ctgaacaaat aattatctga        60 atg aaa aat aca att tcg tgc cta act tta gcg ctt tta agc gca agc        108
Met Lys Asn Thr Ile Ser Cys Leu Thr Leu Ala Leu Leu Ser Ala Ser
1               5                   10                  15 cag tta cat gct caa aca gct gcc gac tcg gct tat gtt aga gat cat        156
Gln Leu His Ala Gln Thr Ala Ala Asp Ser Ala Tyr Val Arg Asp His
            20                  25                  30 tat gaa aag acc gaa gta gca att ccc atg cga gat ggg aaa aaa tta        204
Tyr Glu Lys Thr Glu Val Ala Ile Pro Met Arg Asp Gly Lys Lys Leu
        35                  40                  45 ttt act gcg atc tac agt cca aaa gac aaa tcc aag aaa tat cca gtt        252
Phe Thr Ala Ile Tyr Ser Pro Lys Asp Lys Ser Lys Lys Tyr Pro Val
    50                  55                  60 ttg ctc aat aga acg ccc tac acg gtt tca cct tat ggg cag aac gaa        300
Leu Leu Asn Arg Thr Pro Tyr Thr Val Ser Pro Tyr Gly Gln Asn Glu
65                  70                  75                  80
```

```
tat aaa aaa agc ttg gga aac ttt ccc caa atg atg cgt gaa ggc tat        348
Tyr Lys Lys Ser Leu Gly Asn Phe Pro Gln Met Met Arg Glu Gly Tyr
                 85                  90                  95 att ttc gtt tac cag gat gtc cgt ggc aag tgg atg agc gaa ggt gat        396
Ile Phe Val Tyr Gln Asp Val Arg Gly Lys Trp Met Ser Glu Gly Asp
            100                 105                 110 ttt gaa gat ata cgt ccg acc acg tac agc aaa gat aaa aaa gca atc        444
Phe Glu Asp Ile Arg Pro Thr Thr Tyr Ser Lys Asp Lys Lys Ala Ile
        115                 120                 125 gat gaa agt acg gat acc tat gat gcg ctt gaa tgg tta cag aaa aat        492
Asp Glu Ser Thr Asp Thr Tyr Asp Ala Leu Glu Trp Leu Gln Lys Asn
    130                 135                 140 ctc aaa aac tat aat ggc aaa gcc ggg ctc tat ggg att tcc tat cca        540
Leu Lys Asn Tyr Asn Gly Lys Ala Gly Leu Tyr Gly Ile Ser Tyr Pro
145                 150                 155                 160 ggc ttc tat tct acc gtc gga ttg gtc aaa aca cac ccg agc ttg aag        588
Gly Phe Tyr Ser Thr Val Gly Leu Val Lys Thr His Pro Ser Leu Lys
                165                 170                 175 gca gtc tcc cca cag gct ccc gta aca gac tgg tat atc ggc gac gac        636
Ala Val Ser Pro Gln Ala Pro Val Thr Asp Trp Tyr Ile Gly Asp Asp
            180                 185                 190 ttc cac cat aat ggc gta ttg ttt ctt cag gat gca ttt aca ttc atg        684
Phe His His Asn Gly Val Leu Phe Leu Gln Asp Ala Phe Thr Phe Met
        195                 200                 205 tca acc ttt ggt gtc cct cgt cca aaa ccc att aca ccg gat caa ttt        732
Ser Thr Phe Gly Val Pro Arg Pro Lys Pro Ile Thr Pro Asp Gln Phe
    210                 215                 220 aag ggc aaa att cag atc aaa gaa gcc gat aaa tat aac ttt ttt gca        780
Lys Gly Lys Ile Gln Ile Lys Glu Ala Asp Lys Tyr Asn Phe Phe Ala
225                 230                 235                 240 gaa gca gga aca gcg cgg gaa ctc aaa gaa aag tat ttt ggt gac tcc        828
Glu Ala Gly Thr Ala Arg Glu Leu Lys Glu Lys Tyr Phe Gly Asp Ser
                245                 250                 255 gta caa ttt tgg aat gac ctg ttt aag cat ccc gac tat gat gat ttt        876
Val Gln Phe Trp Asn Asp Leu Phe Lys His Pro Asp Tyr Asp Asp Phe
            260                 265                 270 tgg aaa tcg cgt gtg atc acg aat tct tta cag gag gta aaa cca gct        924
Trp Lys Ser Arg Val Ile Thr Asn Ser Leu Gln Glu Val Lys Pro Ala
        275                 280                 285 gtg atg gtg gtt ggt ggt ttc ttt gac gcg gaa gat gct tat gga aca        972
Val Met Val Val Gly Gly Phe Phe Asp Ala Glu Asp Ala Tyr Gly Thr
    290                 295                 300 ttt aag acc tac caa tcg att gag gat aaa agc aaa aaa aac aac tcg       1020
Phe Lys Thr Tyr Gln Ser Ile Glu Asp Lys Ser Lys Lys Asn Asn Ser
305                 310                 315                 320 att tta gtc gcg gga cct tgg tat cat ggc ggt tgg gtt cgt gca gaa       1068
Ile Leu Val Ala Gly Pro Trp Tyr His Gly Gly Trp Val Arg Ala Glu
                325                 330                 335 gga aac tat tta ggt gat atc caa ttt gag aaa aaa acc agt att act       1116
Gly Asn Tyr Leu Gly Asp Ile Gln Phe Glu Lys Lys Thr Ser Ile Thr
            340                 345                 350 tat cag gaa caa ttt gaa caa cca ttt ttc aaa tat tac cta aaa gat       1164
Tyr Gln Glu Gln Phe Glu Gln Pro Phe Phe Lys Tyr Tyr Leu Lys Asp
        355                 360                 365 gaa gga aac ttc gcc cct tcc gaa gct aac att ttt gtt tca ggc agc       1212
Glu Gly Asn Phe Ala Pro Ser Glu Ala Asn Ile Phe Val Ser Gly Ser
    370                 375                 380 aac gaa tgg aaa cat ttc gaa cag tgg cca cca aaa aat gta gag aca       1260
Asn Glu Trp Lys His Phe Glu Gln Trp Pro Pro Lys Asn Val Glu Thr
385                 390                 395                 400
```

```
aaa aaa cta tac ttc caa cct cag ggg aaa ctt gga ttt gac aaa gtt      1308
Lys Lys Leu Tyr Phe Gln Pro Gln Gly Lys Leu Gly Phe Asp Lys Val
            405                 410                 415 caa cgt aca gat tcc tgg gat gaa tat gta aca gac cct aat aaa cct      1356
Gln Arg Thr Asp Ser Trp Asp Glu Tyr Val Thr Asp Pro Asn Lys Pro
        420                 425                 430 gtt ccg cat caa ggt ggg gta att caa aac cga aca cgg gag tat atg      1404
Val Pro His Gln Gly Gly Val Ile Gln Asn Arg Thr Arg Glu Tyr Met
    435                 440                 445 gta gat gat caa cgt ttc gcg gct agt cgc cct gat gtc atg gtt tat      1452
Val Asp Asp Gln Arg Phe Ala Ala Ser Arg Pro Asp Val Met Val Tyr
450                 455                 460 caa acg gaa ccg ttg acg gag gac ctg acg ata gta ggc cca atc aaa      1500
Gln Thr Glu Pro Leu Thr Glu Asp Leu Thr Ile Val Gly Pro Ile Lys
465                 470                 475                 480 aac ttt ctc aaa gtt tct tca aca gga aca gac gcg gac tat gtt gtc      1548
Asn Phe Leu Lys Val Ser Ser Thr Gly Thr Asp Ala Asp Tyr Val Val
                485                 490                 495 aaa ctg att gac gtt tat ccg aat gat gca gca agt tat caa gga aaa      1596
Lys Leu Ile Asp Val Tyr Pro Asn Asp Ala Ala Ser Tyr Gln Gly Lys
            500                 505                 510 aca atg gct gga tat caa atg atg gta cgt ggt gag atc atg gcg ggg      1644
Thr Met Ala Gly Tyr Gln Met Met Val Arg Gly Glu Ile Met Ala Gly
        515                 520                 525 aaa tac cga aat ggt ttc gat aaa gcg cag gcc ttg act cca ggt atg      1692
Lys Tyr Arg Asn Gly Phe Asp Lys Ala Gln Ala Leu Thr Pro Gly Met
    530                 535                 540 gtc gaa aag gtg aat ttt gaa atg cca gac gtt gcg cat acc ttc aaa      1740
Val Glu Lys Val Asn Phe Glu Met Pro Asp Val Ala His Thr Phe Lys
545                 550                 555                 560 aaa gga cat cgc att atg gtt cag gta caa aac tca tgg ttt ccg ctg      1788
Lys Gly His Arg Ile Met Val Gln Val Gln Asn Ser Trp Phe Pro Leu
                565                 570                 575 gca gaa cga aat cca cag gtg ttt tta gca cct tat aca gct acc aaa      1836
Ala Glu Arg Asn Pro Gln Val Phe Leu Ala Pro Tyr Thr Ala Thr Lys
            580                 585                 590 gct gat ttc cgc aaa gct acc caa cgt att ttt cac gat gtg aac aat      1884
Ala Asp Phe Arg Lys Ala Thr Gln Arg Ile Phe His Asp Val Asn Asn
        595                 600                 605 gcc aca tac atc gaa ttt tct gtc ctc aaa gat tagcaggtaa attcgaaa     1935
Ala Thr Tyr Ile Glu Phe Ser Val Leu Lys Asp
    610                 615
```

<210> SEQ ID NO 12
<211> LENGTH: 619
<212> TYPE: PRT
<213> ORGANISM: Sphingobacterium sp.

<400> SEQUENCE: 12

```
Met Lys Asn Thr Ile Ser Cys Leu Thr Leu Ala Leu Leu Ser Ala Ser
1               5                   10                  15

Gln Leu His Ala Gln Thr Ala Ala Asp Ser Ala Tyr Val Arg Asp His
            20                  25                  30

Tyr Glu Lys Thr Glu Val Ala Ile Pro Met Arg Asp Gly Lys Lys Leu
        35                  40                  45

Phe Thr Ala Ile Tyr Ser Pro Lys Asp Lys Ser Lys Lys Tyr Pro Val
    50                  55                  60

Leu Leu Asn Arg Thr Pro Tyr Thr Val Ser Pro Tyr Gly Gln Asn Glu
65                  70                  75                  80
```

```
Tyr Lys Lys Ser Leu Gly Asn Phe Pro Gln Met Met Arg Glu Gly Tyr
                85                  90                  95

Ile Phe Val Tyr Gln Asp Val Arg Gly Lys Trp Met Ser Glu Gly Asp
            100                 105                 110

Phe Glu Asp Ile Arg Pro Thr Thr Tyr Ser Lys Asp Lys Lys Ala Ile
        115                 120                 125

Asp Glu Ser Thr Asp Thr Tyr Asp Ala Leu Glu Trp Leu Gln Lys Asn
    130                 135                 140

Leu Lys Asn Tyr Asn Gly Lys Ala Gly Leu Tyr Gly Ile Ser Tyr Pro
145                 150                 155                 160

Gly Phe Tyr Ser Thr Val Gly Leu Val Lys Thr His Pro Ser Leu Lys
                165                 170                 175

Ala Val Ser Pro Gln Ala Pro Val Thr Asp Trp Tyr Ile Gly Asp Asp
            180                 185                 190

Phe His His Asn Gly Val Leu Phe Leu Gln Asp Ala Phe Thr Phe Met
        195                 200                 205

Ser Thr Phe Gly Val Pro Arg Pro Lys Pro Ile Thr Pro Asp Gln Phe
    210                 215                 220

Lys Gly Lys Ile Gln Ile Lys Glu Ala Asp Lys Tyr Asn Phe Phe Ala
225                 230                 235                 240

Glu Ala Gly Thr Ala Arg Glu Leu Lys Glu Lys Tyr Phe Gly Asp Ser
                245                 250                 255

Val Gln Phe Trp Asn Asp Leu Phe Lys His Pro Asp Tyr Asp Asp Phe
            260                 265                 270

Trp Lys Ser Arg Val Ile Thr Asn Ser Leu Gln Glu Val Lys Pro Ala
        275                 280                 285

Val Met Val Val Gly Gly Phe Phe Asp Ala Glu Asp Ala Tyr Gly Thr
    290                 295                 300

Phe Lys Thr Tyr Gln Ser Ile Glu Asp Lys Ser Lys Lys Asn Asn Ser
305                 310                 315                 320

Ile Leu Val Ala Gly Pro Trp Tyr His Gly Gly Trp Val Arg Ala Glu
                325                 330                 335

Gly Asn Tyr Leu Gly Asp Ile Gln Phe Glu Lys Lys Thr Ser Ile Thr
            340                 345                 350

Tyr Gln Glu Gln Phe Glu Gln Pro Phe Lys Tyr Tyr Leu Lys Asp
        355                 360                 365

Glu Gly Asn Phe Ala Pro Ser Glu Ala Asn Ile Phe Val Ser Gly Ser
    370                 375                 380

Asn Glu Trp Lys His Phe Glu Gln Trp Pro Lys Asn Val Glu Thr
385                 390                 395                 400

Lys Lys Leu Tyr Phe Gln Pro Gln Gly Lys Leu Gly Phe Asp Lys Val
                405                 410                 415

Gln Arg Thr Asp Ser Trp Asp Gly Tyr Val Thr Asp Pro Asn Lys Pro
            420                 425                 430

Val Pro His Gln Gly Gly Val Ile Gln Asn Arg Thr Arg Glu Tyr Met
        435                 440                 445

Val Asp Asp Gln Arg Phe Ala Ala Ser Arg Pro Asp Val Met Val Tyr
    450                 455                 460

Gln Thr Glu Pro Leu Thr Glu Asp Leu Thr Ile Val Gly Pro Ile Lys
465                 470                 475                 480

Asn Phe Leu Lys Val Ser Ser Thr Gly Thr Asp Ala Asp Tyr Val Val
                485                 490                 495
```

```
Lys Leu Ile Asp Val Tyr Pro Asn Asp Ala Ala Ser Tyr Gln Gly Lys
            500                 505                 510
Thr Met Ala Gly Tyr Gln Met Met Val Arg Gly Glu Ile Met Ala Gly
        515                 520                 525
Lys Tyr Arg Asn Gly Phe Asp Lys Ala Gln Ala Leu Thr Pro Gly Met
    530                 535                 540
Val Glu Lys Val Asn Phe Glu Met Pro Asp Val Ala His Thr Phe Lys
545                 550                 555                 560
Lys Gly His Arg Ile Met Val Gln Val Gln Asn Ser Trp Phe Pro Leu
                565                 570                 575
Ala Glu Arg Asn Pro Gln Val Phe Leu Ala Pro Tyr Thr Ala Thr Lys
            580                 585                 590
Ala Asp Phe Arg Lys Ala Thr Gln Arg Ile Phe His Asp Val Asn Asn
        595                 600                 605
Ala Thr Tyr Ile Glu Phe Ser Val Leu Lys Asp
    610                 615
```

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
gggaattcca tatgaaaaat acaatttcgt                                    30

<210> SEQ ID NO 14
<211> LENGTH: 29
<212> TYPE: DNA
<213> ORGANISM: Artificial Sequence
<220> FEATURE:
<223> OTHER INFORMATION: Synthetic DNA

<400> SEQUENCE: 14
gctctagact aatctttgag gacagaaaa                                     29

<210> SEQ ID NO 15
<211> LENGTH: 17
<212> TYPE: DNA
<213> ORGANISM: Artificial Sequence
<220> FEATURE:
<223> OTHER INFORMATION: Synthetic DNA

<400> SEQUENCE: 15
gaygayttyc aycayaa                                                  17

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t

<400> SEQUENCE: 16
tgrtcrtcna ccatrtaytc                                               20

<210> SEQ ID NO 17
<211> LENGTH: 1974

-continued

```
<212> TYPE: DNA
<213> ORGANISM: Pedobacter heparinus
<220> FEATURE:
<221> NAME/KEY: CDS
<222> LOCATION: (61)..(1935)
<223> OTHER INFORMATION:

<400> SEQUENCE: 17
aaacctatcc cgtattcagc aatcaattcc atatatttat ccttaaaaaa accttcctct     60
```

| | | | | | | | | | | | | | | | | |
|---|---|---|---|---|---|---|---|---|---|---|---|---|---|---|---|---|
| atg | act | cct | ttc | aaa | tcg | ttc | tcc | ttc | att | ttt | ctc | ttt | att | ttt | acc | 108 |
| Met | Thr | Pro | Phe | Lys | Ser | Phe | Ser | Phe | Ile | Phe | Leu | Phe | Ile | Phe | Thr | |
| 1 | | | | 5 | | | | | 10 | | | | | 15 | | |

| agt | ctt | tct | gct | tct | gca | caa | cag | tcc | gac | tct | gct | tat | ata | cgt | cag | 156 |
|---|---|---|---|---|---|---|---|---|---|---|---|---|---|---|---|---|
| Ser | Leu | Ser | Ala | Ser | Ala | Gln | Gln | Ser | Asp | Ser | Ala | Tyr | Ile | Arg | Gln | |
| | | | 20 | | | | | 25 | | | | | 30 | | | |

| aac | tat | acc | aaa | ata | gaa | agg | ctg | atc | cct | atg | cgg | gat | ggc | att | aag | 204 |
|---|---|---|---|---|---|---|---|---|---|---|---|---|---|---|---|---|
| Asn | Tyr | Thr | Lys | Ile | Glu | Arg | Leu | Ile | Pro | Met | Arg | Asp | Gly | Ile | Lys | |
| | | 35 | | | | | 40 | | | | | 45 | | | | |

| cta | ttt | aca | gcc | att | tac | atc | ccc | aaa | gac | aaa | agc | aag | aag | tat | cct | 252 |
|---|---|---|---|---|---|---|---|---|---|---|---|---|---|---|---|---|
| Leu | Phe | Thr | Ala | Ile | Tyr | Ile | Pro | Lys | Asp | Lys | Ser | Lys | Lys | Tyr | Pro | |
| 50 | | | | | 55 | | | | | 60 | | | | | | |

| ttt | atg | ctc | aac | cgt | act | cct | tat | acc | gtt | tcg | cct | tat | ggc | gaa | aac | 300 |
|---|---|---|---|---|---|---|---|---|---|---|---|---|---|---|---|---|
| Phe | Met | Leu | Asn | Arg | Thr | Pro | Tyr | Thr | Val | Ser | Pro | Tyr | Gly | Glu | Asn | |
| 65 | | | | | 70 | | | | | 75 | | | | | 80 | |

| aat | tat | aaa | aca | agc | ctt | ggc | ccc | tct | ccg | ctc | ttt | ata | aaa | gaa | ggc | 348 |
|---|---|---|---|---|---|---|---|---|---|---|---|---|---|---|---|---|
| Asn | Tyr | Lys | Thr | Ser | Leu | Gly | Pro | Ser | Pro | Leu | Phe | Ile | Lys | Glu | Gly | |
| | | | | 85 | | | | | 90 | | | | | 95 | | |

| ttt | atc | ttt | gtt | tat | cag | gat | gta | agg | ggc | aaa | tgg | atg | agt | gag | gga | 396 |
|---|---|---|---|---|---|---|---|---|---|---|---|---|---|---|---|---|
| Phe | Ile | Phe | Val | Tyr | Gln | Asp | Val | Arg | Gly | Lys | Trp | Met | Ser | Glu | Gly | |
| | | | 100 | | | | | 105 | | | | | 110 | | | |

| aaa | ttt | gaa | gac | gta | agg | ccg | caa | ata | gcc | agc | aag | aaa | cgc | aaa | acg | 444 |
|---|---|---|---|---|---|---|---|---|---|---|---|---|---|---|---|---|
| Lys | Phe | Glu | Asp | Val | Arg | Pro | Gln | Ile | Ala | Ser | Lys | Lys | Arg | Lys | Thr | |
| | | 115 | | | | | 120 | | | | | 125 | | | | |

| gat | att | gat | gaa | agc | tcc | gat | act | tat | gat | acg | atc | gac | tgg | ctg | atc | 492 |
|---|---|---|---|---|---|---|---|---|---|---|---|---|---|---|---|---|
| Asp | Ile | Asp | Glu | Ser | Ser | Asp | Thr | Tyr | Asp | Thr | Ile | Asp | Trp | Leu | Ile | |
| | 130 | | | | | 135 | | | | | 140 | | | | | |

| agg | aac | att | cct | gga | aac | aac | cgt | aaa | acc | ggt | att | tac | ggt | atc | tca | 540 |
|---|---|---|---|---|---|---|---|---|---|---|---|---|---|---|---|---|
| Arg | Asn | Ile | Pro | Gly | Asn | Asn | Arg | Lys | Thr | Gly | Ile | Tyr | Gly | Ile | Ser | |
| 145 | | | | | 150 | | | | | 155 | | | | | 160 | |

| tac | cca | ggc | ttt | tat | gct | act | gct | gcc | cta | cca | gat | gcg | cat | cca | tct | 588 |
|---|---|---|---|---|---|---|---|---|---|---|---|---|---|---|---|---|
| Tyr | Pro | Gly | Phe | Tyr | Ala | Thr | Ala | Ala | Leu | Pro | Asp | Ala | His | Pro | Ser | |
| | | | | 165 | | | | | 170 | | | | | 175 | | |

| tta | aag | gca | gta | tcg | ccc | cag | gct | ccg | gtt | acc | gac | tgg | ttt | ata | ggc | 636 |
|---|---|---|---|---|---|---|---|---|---|---|---|---|---|---|---|---|
| Leu | Lys | Ala | Val | Ser | Pro | Gln | Ala | Pro | Val | Thr | Asp | Trp | Phe | Ile | Gly | |
| | | | 180 | | | | | 185 | | | | | 190 | | | |

| gat | gat | ttt | cat | cac | aat | ggc | acc | ttg | ttc | ctt | gca | gat | atc | ttt | agc | 684 |
|---|---|---|---|---|---|---|---|---|---|---|---|---|---|---|---|---|
| Asp | Asp | Phe | His | His | Asn | Gly | Thr | Leu | Phe | Leu | Ala | Asp | Ile | Phe | Ser | |
| | | 195 | | | | | 200 | | | | | 205 | | | | |

| ttc | tat | tat | acc | ttc | ggg | gta | ccg | cga | cct | caa | cca | att | acg | ccc | gac | 732 |
|---|---|---|---|---|---|---|---|---|---|---|---|---|---|---|---|---|
| Phe | Tyr | Tyr | Thr | Phe | Gly | Val | Pro | Arg | Pro | Gln | Pro | Ile | Thr | Pro | Asp | |
| | 210 | | | | | 215 | | | | | 220 | | | | | |

| aaa | cgt | cca | aaa | ccc | ttt | gat | ttc | ccg | gtt | aaa | gac | aac | tac | cgt | ttt | 780 |
|---|---|---|---|---|---|---|---|---|---|---|---|---|---|---|---|---|
| Lys | Arg | Pro | Lys | Pro | Phe | Asp | Phe | Pro | Val | Lys | Asp | Asn | Tyr | Arg | Phe | |
| 225 | | | | | 230 | | | | | 235 | | | | | 240 | |

| ttt | ctt | gaa | ctg | ggc | ccc | tta | aaa | aac | atc | acc | aaa | aaa | tat | tat | ggc | 828 |
|---|---|---|---|---|---|---|---|---|---|---|---|---|---|---|---|---|
| Phe | Leu | Glu | Leu | Gly | Pro | Leu | Lys | Asn | Ile | Thr | Lys | Lys | Tyr | Tyr | Gly | |
| | | | | 245 | | | | | 250 | | | | | 255 | | |

| gat | acc | ata | cga | ttc | tgg | aat | gat | atc | aat | gcg | cat | acc | aat | tat | gat | 876 |
|---|---|---|---|---|---|---|---|---|---|---|---|---|---|---|---|---|
| Asp | Thr | Ile | Arg | Phe | Trp | Asn | Asp | Ile | Asn | Ala | His | Thr | Asn | Tyr | Asp | |
| | | | 260 | | | | | 265 | | | | | 270 | | | |

```
gcc ttc tgg aaa gcc cgt aac att acg ccg cat tta att ggt gta aaa      924
Ala Phe Trp Lys Ala Arg Asn Ile Thr Pro His Leu Ile Gly Val Lys
            275                 280                 285 cct gca gtt ttg gta gtt ggc ggc ttc ttt gat gca gaa gac ctt tac      972
Pro Ala Val Leu Val Val Gly Gly Phe Phe Asp Ala Glu Asp Leu Tyr
290                 295                 300 ggt acg ctt aaa acc tat cag gcc atc gaa aaa caa aat cca tcc tca     1020
Gly Thr Leu Lys Thr Tyr Gln Ala Ile Glu Lys Gln Asn Pro Ser Ser
305                 310                 315                 320 aaa aac aac ctc gtt atg ggc ccc tgg tac cat ggt ggc tgg gca aga     1068
Lys Asn Asn Leu Val Met Gly Pro Trp Tyr His Gly Gly Trp Ala Arg
            325                 330                 335 agt acg gga agc agt ttc ggg gat att aat ttc gga cag cca acc agt     1116
Ser Thr Gly Ser Ser Phe Gly Asp Ile Asn Phe Gly Gln Pro Thr Ser
        340                 345                 350 act tca tac cag caa aat gtt gag ttc cct ttc ttt atg caa tac ctc     1164
Thr Ser Tyr Gln Gln Asn Val Glu Phe Pro Phe Phe Met Gln Tyr Leu
            355                 360                 365 aaa gag gca ccg gat gca aaa att gca gag gca acc att ttt atc act     1212
Lys Glu Ala Pro Asp Ala Lys Ile Ala Glu Ala Thr Ile Phe Ile Thr
370                 375                 380 ggc agc aat gaa tgg aag aaa ttt agc tcc tgg cca cct cag gat aca     1260
Gly Ser Asn Glu Trp Lys Lys Phe Ser Ser Trp Pro Pro Gln Asp Thr
385                 390                 395                 400 gaa gaa aga aca tta tac ctg cag ccc aat ggc aaa ctg agc ttt gag     1308
Glu Glu Arg Thr Leu Tyr Leu Gln Pro Asn Gly Lys Leu Ser Phe Glu
            405                 410                 415 aag gta cag cgg acc gac agc tgg gat gaa tat gta agt gat ccc aat     1356
Lys Val Gln Arg Thr Asp Ser Trp Asp Glu Tyr Val Ser Asp Pro Asn
        420                 425                 430 tca cct gtc cct tat cag gat ggc ata caa acc agc aga acc cgg gaa     1404
Ser Pro Val Pro Tyr Gln Asp Gly Ile Gln Thr Ser Arg Thr Arg Glu
            435                 440                 445 tat atg atc gat gac cag cgt ttt gcc tcg cgc aga ccg gat gta agg     1452
Tyr Met Ile Asp Asp Gln Arg Phe Ala Ser Arg Arg Pro Asp Val Arg
450                 455                 460 gta ttc caa aca gag ccc ctc agt tcc gac ctt aca ctt acc ggc ccg     1500
Val Phe Gln Thr Glu Pro Leu Ser Ser Asp Leu Thr Leu Thr Gly Pro
465                 470                 475                 480 gta ttg gcc aaa ctg gtg gta tca acc aca ggt acg gat gca gat tat     1548
Val Leu Ala Lys Leu Val Val Ser Thr Thr Gly Thr Asp Ala Asp Tyr
            485                 490                 495 gtg gta aaa ctg ata gat gta tat ccg gaa gat aca cca aat cct gta     1596
Val Val Lys Leu Ile Asp Val Tyr Pro Glu Asp Thr Pro Asn Pro Val
        500                 505                 510 cct aac cct aaa aac ctg atc atg ggt ggt tac cag atg ctg gta cgc     1644
Pro Asn Pro Lys Asn Leu Ile Met Gly Gly Tyr Gln Met Leu Val Arg
            515                 520                 525 ggc gag atc atg cgt gga aaa tac cgt aat agc ttt gaa aaa ccc gag     1692
Gly Glu Ile Met Arg Gly Lys Tyr Arg Asn Ser Phe Glu Lys Pro Glu
530                 535                 540 cct ttt gtt cct gga aca att aca aaa gta aac tat gcc ctt ccg gat     1740
Pro Phe Val Pro Gly Thr Ile Thr Lys Val Asn Tyr Ala Leu Pro Asp
545                 550                 555                 560 gta gcc cat acc ttt aaa aaa ggc cac cgc atc atg atc cag gtc cag     1788
Val Ala His Thr Phe Lys Lys Gly His Arg Ile Met Ile Gln Val Gln
            565                 570                 575 aat tca tgg ttt ccc ctg gcc gac cgg aat cca cag cag ttt atg gac     1836
Asn Ser Trp Phe Pro Leu Ala Asp Arg Asn Pro Gln Gln Phe Met Asp
        580                 585                 590
```

```
att tac cag gcc gaa cct ggc gat ttc aga aaa gct acg cat agg atc    1884
Ile Tyr Gln Ala Glu Pro Gly Asp Phe Arg Lys Ala Thr His Arg Ile
        595                 600                 605 ttc cac gat gta cac aat gca tct gca att acg gta aac gta ctg aaa    1932
Phe His Asp Val His Asn Ala Ser Ala Ile Thr Val Asn Val Leu Lys
    610                 615                 620 cct taaaacggat gaaaccagta tattgtgcca tccttactt                     1974
Pro
625

<210> SEQ ID NO 18
<211> LENGTH: 625
<212> TYPE: PRT
<213> ORGANISM: Pedobacter heparinus

<400> SEQUENCE: 18

Met Thr Pro Phe Lys Ser Phe Ser Phe Ile Phe Leu Phe Ile Phe Thr
1               5                   10                  15

Ser Leu Ser Ala Ser Ala Gln Gln Ser Asp Ser Ala Tyr Ile Arg Gln
            20                  25                  30

Asn Tyr Thr Lys Ile Glu Arg Leu Ile Pro Met Arg Asp Gly Ile Lys
        35                  40                  45

Leu Phe Thr Ala Ile Tyr Ile Pro Lys Asp Lys Ser Lys Lys Tyr Pro
    50                  55                  60

Phe Met Leu Asn Arg Thr Pro Tyr Thr Val Ser Pro Tyr Gly Glu Asn
65                  70                  75                  80

Asn Tyr Lys Thr Ser Leu Gly Pro Ser Pro Leu Phe Ile Lys Glu Gly
                85                  90                  95

Phe Ile Phe Val Tyr Gln Asp Val Arg Gly Lys Trp Met Ser Glu Gly
            100                 105                 110

Lys Phe Glu Asp Val Arg Pro Gln Ile Ala Ser Lys Lys Arg Lys Thr
        115                 120                 125

Asp Ile Asp Glu Ser Ser Asp Thr Tyr Asp Thr Ile Asp Trp Leu Ile
    130                 135                 140

Arg Asn Ile Pro Gly Asn Asn Arg Lys Thr Gly Ile Tyr Gly Ile Ser
145                 150                 155                 160

Tyr Pro Gly Phe Tyr Ala Thr Ala Ala Leu Pro Asp Ala His Pro Ser
                165                 170                 175

Leu Lys Ala Val Ser Pro Gln Ala Pro Val Thr Asp Trp Phe Ile Gly
            180                 185                 190

Asp Asp Phe His His Asn Gly Thr Leu Phe Leu Ala Asp Ile Phe Ser
        195                 200                 205

Phe Tyr Tyr Thr Phe Gly Val Pro Arg Pro Gln Pro Ile Thr Pro Asp
    210                 215                 220

Lys Arg Pro Lys Pro Phe Asp Phe Pro Val Lys Asp Asn Tyr Arg Phe
225                 230                 235                 240

Phe Leu Glu Leu Gly Pro Leu Lys Asn Ile Thr Lys Lys Tyr Tyr Gly
                245                 250                 255

Asp Thr Ile Arg Phe Trp Asn Asp Asn Ala His Thr Asn Tyr Asp
            260                 265                 270

Ala Phe Trp Lys Ala Arg Asn Ile Thr Pro His Leu Ile Gly Val Lys
        275                 280                 285

Pro Ala Val Leu Val Val Gly Gly Phe Phe Asp Ala Glu Asp Leu Tyr
    290                 295                 300

Gly Thr Leu Lys Thr Tyr Gln Ala Ile Glu Lys Gln Asn Pro Ser Ser
```

```
            305                 310                 315                 320
Lys Asn Asn Leu Val Met Gly Pro Trp Tyr His Gly Gly Trp Ala Arg
                325                 330                 335

Ser Thr Gly Ser Ser Phe Gly Asp Ile Asn Phe Gly Gln Pro Thr Ser
                340                 345                 350

Thr Ser Tyr Gln Gln Asn Val Glu Phe Pro Phe Met Gln Tyr Leu
                355                 360                 365

Lys Glu Ala Pro Asp Ala Lys Ile Ala Glu Ala Thr Ile Phe Ile Thr
                370                 375                 380

Gly Ser Asn Glu Trp Lys Lys Phe Ser Ser Trp Pro Pro Gln Asp Thr
385                 390                 395                 400

Glu Glu Arg Thr Leu Tyr Leu Gln Pro Asn Gly Lys Leu Ser Phe Glu
                405                 410                 415

Lys Val Gln Arg Thr Asp Ser Trp Asp Glu Tyr Val Ser Asp Pro Asn
                420                 425                 430

Ser Pro Val Pro Tyr Gln Asp Gly Ile Gln Thr Ser Arg Thr Arg Glu
                435                 440                 445

Tyr Met Ile Asp Asp Gln Arg Phe Ala Ser Arg Pro Asp Val Arg
450                 455                 460

Val Phe Gln Thr Glu Pro Leu Ser Ser Asp Leu Thr Leu Thr Gly Pro
465                 470                 475                 480

Val Leu Ala Lys Leu Val Ser Thr Thr Gly Thr Asp Ala Asp Tyr
                485                 490                 495

Val Val Lys Leu Ile Asp Val Tyr Pro Glu Asp Thr Pro Asn Pro Val
                500                 505                 510

Pro Asn Pro Lys Asn Leu Ile Met Gly Gly Tyr Gln Met Leu Val Arg
                515                 520                 525

Gly Glu Ile Met Arg Gly Lys Tyr Arg Asn Ser Phe Glu Lys Pro Glu
                530                 535                 540

Pro Phe Val Pro Gly Thr Ile Thr Lys Val Asn Tyr Ala Leu Pro Asp
545                 550                 555                 560

Val Ala His Thr Phe Lys Lys Gly His Arg Ile Met Ile Gln Val Gln
                565                 570                 575

Asn Ser Trp Phe Pro Leu Ala Asp Arg Asn Pro Gln Gln Phe Met Asp
                580                 585                 590

Ile Tyr Gln Ala Glu Pro Gly Asp Phe Arg Lys Ala Thr His Arg Ile
                595                 600                 605

Phe His Asp Val His Asn Ala Ser Ala Ile Thr Val Asn Val Leu Lys
                610                 615                 620

Pro
625

<210> SEQ ID NO 19
<211> LENGTH: 38
<212> TYPE: DNA
<213> ORGANISM: Artificial Sequence
<220> FEATURE:
<223> OTHER INFORMATION: Synthetic DNA

<400> SEQUENCE: 19
gggaattcca tatgactcct ttcaaatcgt tctccttc                           38

<210> SEQ ID NO 20
<211> LENGTH: 30
<212> TYPE: DNA
<213> ORGANISM: Artificial Sequence
```

```
<220> FEATURE:
<223> OTHER INFORMATION: Synthetic DNA

<400> SEQUENCE: 20
cccaagcttt taaggtttca gtacgtttac                                      30

<210> SEQ ID NO 21
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t

<400> SEQUENCE: 21
athttygtnt aycarga                                                    17

<210> SEQ ID NO 22
<211> LENGTH: 2018
<212> TYPE: DNA
<213> ORGANISM: Taxeobacter gelupurpurascens
<220> FEATURE:
<221> NAME/KEY: CDS
<222> LOCATION: (61)..(1995)
<223> OTHER INFORMATION:

<400> SEQUENCE: 22
```

| | | | | | | | | | | | | | | | | |
|---|---|---|---|---|---|---|---|---|---|---|---|---|---|---|---|---|
| ctgaatgtct gctgacgaat tggaactaca ttaggctcgt tcttcaccta cccttccact | | | | | | | | | | | | | | | | 60 |
| atg | ccc | tac | tct | ttc | ccg | aaa | gtt | gcc | gcc | ctg | agt | ggc | cta | ctg | gtg | 108 |
| Met | Pro | Tyr | Ser | Phe | Pro | Lys | Val | Ala | Ala | Leu | Ser | Gly | Leu | Leu | Val | |
| 1 | | | | 5 | | | | | 10 | | | | | 15 | | |
| gcc | ggt | tta | tcc | ggt | gcc | cac | gcc | caa | act | cct | gtt | acc | tat | ccg | ctg | 156 |
| Ala | Gly | Leu | Ser | Gly | Ala | His | Ala | Gln | Thr | Pro | Val | Thr | Tyr | Pro | Leu | |
| | | 20 | | | | | 25 | | | | | 30 | | | | |
| gct | tct | gag | gct | gaa | aaa | gcg | cag | ctg | gcg | gtg | gta | cta | gcc | gat | acg | 204 |
| Ala | Ser | Glu | Ala | Glu | Lys | Ala | Gln | Leu | Ala | Val | Val | Leu | Ala | Asp | Thr | |
| | | | 35 | | | | | 40 | | | | | 45 | | | |
| gct | tac | atc | aag | gag | cgc | tat | acc | aaa | aca | gaa | tat | cag | att | ccg | atg | 252 |
| Ala | Tyr | Ile | Lys | Glu | Arg | Tyr | Thr | Lys | Thr | Glu | Tyr | Gln | Ile | Pro | Met | |
| 50 | | | | | 55 | | | | | 60 | | | | | | |
| cgc | gat | ggg | gtg | aag | ttg | tac | acc | att | gtg | tac | gcg | ccc | aac | gat | gcc | 300 |
| Arg | Asp | Gly | Val | Lys | Leu | Tyr | Thr | Ile | Val | Tyr | Ala | Pro | Asn | Asp | Ala | |
| 65 | | | | | 70 | | | | | 75 | | | | | 80 | |
| aac | aag | gta | aag | tac | cct | att | ctg | ctc | aac | cgt | acc | cct | tac | gct | att | 348 |
| Asn | Lys | Val | Lys | Tyr | Pro | Ile | Leu | Leu | Asn | Arg | Thr | Pro | Tyr | Ala | Ile | |
| | | | | 85 | | | | | 90 | | | | | 95 | | |
| ggc | ccc | tac | ggc | ccc | ggc | aaa | tac | aag | ctc | aac | ctg | ggc | ccc | agc | agc | 396 |
| Gly | Pro | Tyr | Gly | Pro | Gly | Lys | Tyr | Lys | Leu | Asn | Leu | Gly | Pro | Ser | Ser | |
| | | | 100 | | | | | 105 | | | | | 110 | | | |
| acg | atg | atg | cat | gag | gga | tac | atc | ttc | gcc | tac | cag | gat | gtg | cgt | ggg | 444 |
| Thr | Met | Met | His | Glu | Gly | Tyr | Ile | Phe | Ala | Tyr | Gln | Asp | Val | Arg | Gly | |
| | | 115 | | | | | 120 | | | | | 125 | | | | |
| cga | tat | atg | tcg | gaa | gga | gag | ttt | gtg | gat | gtg | cgc | ccc | gaa | aag | gac | 492 |
| Arg | Tyr | Met | Ser | Glu | Gly | Glu | Phe | Val | Asp | Val | Arg | Pro | Glu | Lys | Asp | |
| | | | 130 | | | | | 135 | | | | | 140 | | | |
| atg | cac | aaa | ggc | aag | aac | gac | atc | gat | gaa | ggc | acc | gac | acc | tac | gat | 540 |
| Met | His | Lys | Gly | Lys | Asn | Asp | Ile | Asp | Glu | Gly | Thr | Asp | Thr | Tyr | Asp | |
| 145 | | | | | 150 | | | | | 155 | | | | | 160 | |
| acc | att | gag | tgg | ctt | ctg | aag | cac | ggg | ccc | aag | aat | aac | ggc | cgc | gta | 588 |
| Thr | Ile | Glu | Trp | Leu | Leu | Lys | His | Gly | Pro | Lys | Asn | Asn | Gly | Arg | Val | |

```
                    165                 170                 175
ggc cag tgg ggc atc tcc tac ccc ggc tac tat acc gct act ggc cta      636
Gly Gln Trp Gly Ile Ser Tyr Pro Gly Tyr Tyr Thr Ala Thr Gly Leu
            180                 185                 190 ctg agc cgc cac aag gcc cta aag gca tcc tca ccg cag gcc cct att      684
Leu Ser Arg His Lys Ala Leu Lys Ala Ser Ser Pro Gln Ala Pro Ile
        195                 200                 205 gcc gac tgg ttc tgg gac gat ttt cac cac aac ggc gcg ttc ttc ctg      732
Ala Asp Trp Phe Trp Asp Asp Phe His His Asn Gly Ala Phe Phe Leu
    210                 215                 220 ccg cac gct ttt aac ttc ctg gcc tcc ttt ggg ctg gcc cgc ccc cag      780
Pro His Ala Phe Asn Phe Leu Ala Ser Phe Gly Leu Ala Arg Pro Gln
225                 230                 235                 240 ccc acg cct acc ggc aac ccc ggc ttc aag cac ggc acc ccc gat ggc      828
Pro Thr Pro Thr Gly Asn Pro Gly Phe Lys His Gly Thr Pro Asp Gly
                245                 250                 255 tac gat ttt ttc ctg aag atg ggt ccg ctg aaa aac gct gat gcc aac      876
Tyr Asp Phe Phe Leu Lys Met Gly Pro Leu Lys Asn Ala Asp Ala Asn
            260                 265                 270 tac tac aaa ggc aaa gtg gcc ttc tgg aac gaa atg gcc agc cac ccc      924
Tyr Tyr Lys Gly Lys Val Ala Phe Trp Asn Glu Met Ala Ser His Pro
        275                 280                 285 aac tac gac gaa ttc tgg cag gcc cgt aac cta cgc ccc cac ctc aag      972
Asn Tyr Asp Glu Phe Trp Gln Ala Arg Asn Leu Arg Pro His Leu Lys
    290                 295                 300 aac ctc aac aaa ggc acc gcg gtg ctc acg gtt ggt ggc ttc aat gat     1020
Asn Leu Asn Lys Gly Thr Ala Val Leu Thr Val Gly Gly Phe Asn Asp
305                 310                 315                 320 gcc gag gac ctg ttt ggc gcc ctg aaa acc tac gaa agc atc gag aag     1068
Ala Glu Asp Leu Phe Gly Ala Leu Lys Thr Tyr Glu Ser Ile Glu Lys
                325                 330                 335 caa aac ccc ggc atg cgc aac ggc ctc gtg atg ggg ccg tgg gta cac     1116
Gln Asn Pro Gly Met Arg Asn Gly Leu Val Met Gly Pro Trp Val His
            340                 345                 350 ggt ggc tgg gcc cgc ggc act ggc gaa atg gta ggc aat gtg gcc tac     1164
Gly Gly Trp Ala Arg Gly Thr Gly Glu Met Val Gly Asn Val Ala Tyr
        355                 360                 365 ggc gag tcg ccg tcg ttg tat tac cag aag cag att gaa gcg ccg ttc     1212
Gly Glu Ser Pro Ser Leu Tyr Tyr Gln Lys Gln Ile Glu Ala Pro Phe
    370                 375                 380 ttc aaa tca tat ctg aag gat ggc aaa cct gcc gct acc ccc gag gct     1260
Phe Lys Ser Tyr Leu Lys Asp Gly Lys Pro Ala Ala Thr Pro Glu Ala
385                 390                 395                 400 acc atc ttt gaa agc ggc acc aac cgc tgg cgc agc ttc gaa acc tgg     1308
Thr Ile Phe Glu Ser Gly Thr Asn Arg Trp Arg Ser Phe Glu Thr Trp
                405                 410                 415 ccg ccc aaa gaa gcc aaa gag cgc act ttg tac ttt cag tcg gcc ggg     1356
Pro Pro Lys Glu Ala Lys Glu Arg Thr Leu Tyr Phe Gln Ser Ala Gly
            420                 425                 430 aaa atc ggc ttc gag aag cct gcc agt ggc cta gag tac gac cag ttc     1404
Lys Ile Gly Phe Glu Lys Pro Ala Ser Gly Leu Glu Tyr Asp Gln Phe
        435                 440                 445 ctc agc gac ccg gct cac cca gtg cct ttc acc gaa gct acg gct acg     1452
Leu Ser Asp Pro Ala His Pro Val Pro Phe Thr Glu Ala Thr Ala Thr
    450                 455                 460 ggc atg acc cgc gag tac atg acc gac gac cag cgc ttc gcc agc cgc     1500
Gly Met Thr Arg Glu Tyr Met Thr Asp Asp Gln Arg Phe Ala Ser Arg
465                 470                 475                 480 cgc ccc gac gtg ctg acc tac cag acc gaa gcg ctt acc gag gac atg     1548
```

```
                Arg Pro Asp Val Leu Thr Tyr Gln Thr Glu Ala Leu Thr Glu Asp Met
                                485                 490                 495 acg ctg gct ggc cct atc gag gcg ctg ttg cag gta gcc acc acc ggc          1596
Thr Leu Ala Gly Pro Ile Glu Ala Leu Leu Gln Val Ala Thr Thr Gly
            500                 505                 510 acc gat gcc gac tgg gta gtg aag att att gat gtg tac ccc gac gat          1644
Thr Asp Ala Asp Trp Val Val Lys Ile Ile Asp Val Tyr Pro Asp Asp
            515                 520                 525 acg ccc aac aac ccc agc acg aac ccc gcc gtg aaa ctg ggc ggc tac          1692
Thr Pro Asn Asn Pro Ser Thr Asn Pro Ala Val Lys Leu Gly Gly Tyr
            530                 535                 540 cag cag atg gtt cgc tcc gag gtg atg cgc ggt cgt ttc cgc aac agc          1740
Gln Gln Met Val Arg Ser Glu Val Met Arg Gly Arg Phe Arg Asn Ser
545                 550                 555                 560 ttc tcc aag ccc gaa gcc ttt gta ccg gaa cag gta acg gcc gtg ccc          1788
Phe Ser Lys Pro Glu Ala Phe Val Pro Glu Gln Val Thr Ala Val Pro
                565                 570                 575 ttc acg gtg cag gac ctg tgc cac acc ttc cgg aaa gga cac cgc ctg          1836
Phe Thr Val Gln Asp Leu Cys His Thr Phe Arg Lys Gly His Arg Leu
            580                 585                 590 atg gtg cag gtg caa agc agc tgg ttc ccg att gtt gac cgc aac ccg          1884
Met Val Gln Val Gln Ser Ser Trp Phe Pro Ile Val Asp Arg Asn Pro
            595                 600                 605 cag acc ttc gta ccc aat att ttc gag gcc gat gag aag gat ttc cag          1932
Gln Thr Phe Val Pro Asn Ile Phe Glu Ala Asp Glu Lys Asp Phe Gln
            610                 615                 620 gcc gcc acg cat cgg ctg tac cat tcg ccg gcg cat agc tcg cag ctc          1980
Ala Ala Thr His Arg Leu Tyr His Ser Pro Ala His Ser Ser Gln Leu
625                 630                 635                 640 acg ttg cgc gtt ctg taggccactc taaacaggct cgg                            2018
Thr Leu Arg Val Leu
                645

<210> SEQ ID NO 23
<211> LENGTH: 645
<212> TYPE: PRT
<213> ORGANISM: Taxeobacter gelupurpurascens

<400> SEQUENCE: 23

Met Pro Tyr Ser Phe Pro Lys Val Ala Ala Leu Ser Gly Leu Leu Val
1               5                   10                  15

Ala Gly Leu Ser Gly Ala His Ala Gln Thr Pro Val Thr Tyr Pro Leu
                20                  25                  30

Ala Ser Glu Ala Glu Lys Ala Gln Leu Ala Val Val Leu Ala Asp Thr
            35                  40                  45

Ala Tyr Ile Lys Glu Arg Tyr Thr Lys Thr Glu Tyr Gln Ile Pro Met
        50                  55                  60

Arg Asp Gly Val Lys Leu Tyr Thr Ile Val Tyr Ala Pro Asn Asp Ala
65                  70                  75                  80

Asn Lys Val Lys Tyr Pro Ile Leu Leu Asn Arg Thr Pro Tyr Ala Ile
                85                  90                  95

Gly Pro Tyr Gly Pro Gly Lys Tyr Lys Leu Asn Leu Gly Pro Ser Ser
            100                 105                 110

Thr Met Met His Glu Gly Tyr Ile Phe Ala Tyr Gln Asp Val Arg Gly
        115                 120                 125

Arg Tyr Met Ser Glu Gly Glu Phe Val Asp Val Arg Pro Glu Lys Asp
    130                 135                 140

Met His Lys Gly Lys Asn Asp Ile Asp Glu Gly Thr Asp Thr Tyr Asp
```

-continued

```
            145                 150                 155                 160
Thr Ile Glu Trp Leu Leu Lys His Gly Pro Lys Asn Asn Gly Arg Val
                165                 170                 175
Gly Gln Trp Gly Ile Ser Tyr Pro Gly Tyr Tyr Thr Ala Thr Gly Leu
            180                 185                 190
Leu Ser Arg His Lys Ala Leu Lys Ala Ser Ser Pro Gln Ala Pro Ile
        195                 200                 205
Ala Asp Trp Phe Trp Asp Asp Phe His His Asn Gly Ala Phe Phe Leu
210                 215                 220
Pro His Ala Phe Asn Phe Leu Ala Ser Phe Gly Leu Ala Arg Pro Gln
225                 230                 235                 240
Pro Thr Pro Thr Gly Asn Pro Gly Phe Lys His Gly Thr Pro Asp Gly
                245                 250                 255
Tyr Asp Phe Phe Leu Lys Met Gly Pro Leu Lys Asn Ala Asp Ala Asn
                260                 265                 270
Tyr Tyr Lys Gly Lys Val Ala Phe Trp Asn Glu Met Ala Ser His Pro
            275                 280                 285
Asn Tyr Asp Glu Phe Trp Gln Ala Arg Asn Leu Arg Pro His Leu Lys
        290                 295                 300
Asn Leu Asn Lys Gly Thr Ala Val Leu Thr Val Gly Phe Asn Asp
305                 310                 315                 320
Ala Glu Asp Leu Phe Gly Ala Leu Lys Thr Tyr Glu Ser Ile Glu Lys
                325                 330                 335
Gln Asn Pro Gly Met Arg Asn Gly Leu Val Met Gly Pro Trp Val His
            340                 345                 350
Gly Gly Trp Ala Arg Gly Thr Gly Glu Met Val Gly Asn Val Ala Tyr
        355                 360                 365
Gly Glu Ser Pro Ser Leu Tyr Tyr Gln Lys Gln Ile Glu Ala Pro Phe
    370                 375                 380
Phe Lys Ser Tyr Leu Lys Asp Gly Lys Pro Ala Ala Thr Pro Glu Ala
385                 390                 395                 400
Thr Ile Phe Glu Ser Gly Thr Asn Arg Trp Arg Ser Phe Glu Thr Trp
                405                 410                 415
Pro Pro Lys Glu Ala Lys Glu Arg Thr Leu Tyr Phe Gln Ser Ala Gly
            420                 425                 430
Lys Ile Gly Phe Glu Lys Pro Ala Ser Gly Leu Glu Tyr Asp Gln Phe
        435                 440                 445
Leu Ser Asp Pro Ala His Pro Val Pro Phe Thr Glu Ala Thr Ala Thr
    450                 455                 460
Gly Met Thr Arg Glu Tyr Met Thr Asp Gln Arg Phe Ala Ser Arg
465                 470                 475                 480
Arg Pro Asp Val Leu Thr Tyr Gln Thr Glu Ala Leu Thr Glu Asp Met
                485                 490                 495
Thr Leu Ala Gly Pro Ile Glu Ala Leu Leu Gln Val Ala Thr Thr Gly
            500                 505                 510
Thr Asp Ala Asp Trp Val Val Lys Ile Ile Asp Val Tyr Pro Asp Asp
        515                 520                 525
Thr Pro Asn Asn Pro Ser Thr Asn Pro Ala Val Lys Leu Gly Gly Tyr
    530                 535                 540
Gln Gln Met Val Arg Ser Glu Val Met Arg Gly Arg Phe Arg Asn Ser
545                 550                 555                 560
Phe Ser Lys Pro Glu Ala Phe Val Pro Glu Gln Val Thr Ala Val Pro
                565                 570                 575
```

```
Phe Thr Val Gln Asp Leu Cys His Thr Phe Arg Lys Gly His Arg Leu
            580                 585                 590
Met Val Gln Val Gln Ser Ser Trp Phe Pro Ile Val Asp Arg Asn Pro
        595                 600                 605
Gln Thr Phe Val Pro Asn Ile Phe Glu Ala Asp Glu Lys Asp Phe Gln
    610                 615                 620
Ala Ala Thr His Arg Leu Tyr His Ser Pro Ala His Ser Ser Gln Leu
625                 630                 635                 640
Thr Leu Arg Val Leu
                645

<210> SEQ ID NO 24
<211> LENGTH: 1931
<212> TYPE: DNA
<213> ORGANISM: Cyclobacterium marinum
<220> FEATURE:
<221> NAME/KEY: CDS
<222> LOCATION: (29)..(1888)
<223> OTHER INFORMATION:

<400> SEQUENCE: 24
cccaaagcat taacaaaata atttagtc atg aaa cac tgt tac aaa ctt ctg       52
                             Met Lys His Cys Tyr Lys Leu Leu
                               1               5 gtc ttt tac aca tta ttt ttg atg acc aca aac tgg gct tta tca caa    100
Val Phe Tyr Thr Leu Phe Leu Met Thr Thr Asn Trp Ala Leu Ser Gln
         10                  15                  20 gcc att aat gga tat gat aag gca gcc tat gac att cct atg cga gat    148
Ala Ile Asn Gly Tyr Asp Lys Ala Ala Tyr Asp Ile Pro Met Arg Asp
 25                  30                  35                  40 gga gtt cac ctt cac acc atc gtc tat agc ccc aaa gat tta tcg cag    196
Gly Val His Leu His Thr Ile Val Tyr Ser Pro Lys Asp Leu Ser Gln
                 45                  50                  55 ccc tat cct ata ttg atg caa agg aca cct tac agc gcc ggc cct tat    244
Pro Tyr Pro Ile Leu Met Gln Arg Thr Pro Tyr Ser Ala Gly Pro Tyr
             60                  65                  70 ggt cct gga aat atg aaa aat aag ctt ggc cct tct cag ttt tta atg    292
Gly Pro Gly Asn Met Lys Asn Lys Leu Gly Pro Ser Gln Phe Leu Met
         75                  80                  85 aac gat ggc tat ata ttt gtt tac cag gat gta aga ggg cgg tgg atg    340
Asn Asp Gly Tyr Ile Phe Val Tyr Gln Asp Val Arg Gly Arg Trp Met
 90                  95                 100 tcg gaa gga tcc tat gac aac atg cgc cct acc cta tcc aaa tca gaa    388
Ser Glu Gly Ser Tyr Asp Asn Met Arg Pro Thr Leu Ser Lys Ser Glu
105                 110                 115                 120 aga aat tcc aac caa ata gac gaa agc aca gac acc tat gat acc ata    436
Arg Asn Ser Asn Gln Ile Asp Glu Ser Thr Asp Thr Tyr Asp Thr Ile
                125                 130                 135 gaa tgg ttg ctc gcc aat atc aaa aat cac aat gaa aaa gta ggc cta    484
Glu Trp Leu Leu Ala Asn Ile Lys Asn His Asn Glu Lys Val Gly Leu
            140                 145                 150 tgg gga atc agc tat ccc gga ttt tat agt gct gca gcc ctt cct ttt    532
Trp Gly Ile Ser Tyr Pro Gly Phe Tyr Ser Ala Ala Ala Leu Pro Phe
        155                 160                 165 gcc cat cca aac ctg aaa gcc gtt tcc cct caa gca ccc ata ggg gat    580
Ala His Pro Asn Leu Lys Ala Val Ser Pro Gln Ala Pro Ile Gly Asp
    170                 175                 180 ttt tac ttt gat gat ttt cat cat aac ggt gct tac tta tta agt tat    628
Phe Tyr Phe Asp Asp Phe His His Asn Gly Ala Tyr Leu Leu Ser Tyr
185                 190                 195                 200
```

| | |
|---|---:|
| tgg ttg gcc act tct gtt ttc ggc tac caa aaa gac ggc cct aca cag<br>Trp Leu Ala Thr Ser Val Phe Gly Tyr Gln Lys Asp Gly Pro Thr Gln<br>205 210 215 | 676 |
| gaa gca tgg tat ggc atg gtg aat ccg gaa aca aat gac ggc tat cag<br>Glu Ala Trp Tyr Gly Met Val Asn Pro Glu Thr Asn Asp Gly Tyr Gln<br>220 225 230 | 724 |
| ttt ttt atg gat atg ggg cca tta aaa aat gcc gat aaa tgg tat ggt<br>Phe Phe Met Asp Met Gly Pro Leu Lys Asn Ala Asp Lys Trp Tyr Gly<br>235 240 245 | 772 |
| gaa gac aat ttt ttc tgg caa caa ctt aaa aac aat cct gat tac aac<br>Glu Asp Asn Phe Phe Trp Gln Gln Leu Lys Asn Asn Pro Asp Tyr Asn<br>250 255 260 | 820 |
| gct ttc tgg caa aag aga agt att att cct cac tta aaa gaa gtg aag<br>Ala Phe Trp Gln Lys Arg Ser Ile Ile Pro His Leu Lys Glu Val Lys<br>265 270 275 280 | 868 |
| cct gca gtt tta acc gtt ggg ggc tgg ttt gat gca gaa gat ctc tat<br>Pro Ala Val Leu Thr Val Gly Gly Trp Phe Asp Ala Glu Asp Leu Tyr<br>285 290 295 | 916 |
| gga cca ctt aca att tat aaa acc att gaa aaa aat aat cct gag acc<br>Gly Pro Leu Thr Ile Tyr Lys Thr Ile Glu Lys Asn Asn Pro Glu Thr<br>300 305 310 | 964 |
| tac aat acc att gtc atg ggc cct tgg tcc cac gga gat tgg tca agg<br>Tyr Asn Thr Ile Val Met Gly Pro Trp Ser His Gly Asp Trp Ser Arg<br>315 320 325 | 1012 |
| gaa cct gga tca cag gtc att tca aat att tat ttt ggt gat tct atc<br>Glu Pro Gly Ser Gln Val Ile Ser Asn Ile Tyr Phe Gly Asp Ser Ile<br>330 335 340 | 1060 |
| tcc aca tgg tat caa aaa aat ata gaa cgt gtt ttt ttc aat cat ttt<br>Ser Thr Trp Tyr Gln Lys Asn Ile Glu Arg Val Phe Phe Asn His Phe<br>345 350 355 360 | 1108 |
| cta aaa gaa tcc gaa aat agc aat cct gcc ctt cct gaa gcc tac atg<br>Leu Lys Glu Ser Glu Asn Ser Asn Pro Ala Leu Pro Glu Ala Tyr Met<br>365 370 375 | 1156 |
| ttt gat acc gga aaa cat aaa tgg gaa aaa ttt gac gat tgg cct cct<br>Phe Asp Thr Gly Lys His Lys Trp Glu Lys Phe Asp Asp Trp Pro Pro<br>380 385 390 | 1204 |
| aaa gaa agc caa tgg aaa agc ttt tac ttt caa gag aaa gga gag tta<br>Lys Glu Ser Gln Trp Lys Ser Phe Tyr Phe Gln Glu Lys Gly Glu Leu<br>395 400 405 | 1252 |
| act gag gta aca cct gag gga aat agg ttt act acc tat gtc tca gac<br>Thr Glu Val Thr Pro Glu Gly Asn Arg Phe Thr Thr Tyr Val Ser Asp<br>410 415 420 | 1300 |
| ccc tct aat cct gtc ccc tat agt caa gat att aaa cta aac ttc act<br>Pro Ser Asn Pro Val Pro Tyr Ser Gln Asp Ile Lys Leu Asn Phe Thr<br>425 430 435 440 | 1348 |
| ccg aga aaa tac atg gcc gat gac cag cga ttt gca gcc aga aga ccg<br>Pro Arg Lys Tyr Met Ala Asp Asp Gln Arg Phe Ala Ala Arg Arg Pro<br>445 450 455 | 1396 |
| gac gta ctg acc ttt acg agc gaa gta tta agt caa gac atg acg ctt<br>Asp Val Leu Thr Phe Thr Ser Glu Val Leu Ser Gln Asp Met Thr Leu<br>460 465 470 | 1444 |
| gcg ggg gaa gtc atg gca aac tta aaa gtt gcc act tca caa act gat<br>Ala Gly Glu Val Met Ala Asn Leu Lys Val Ala Thr Ser Gln Thr Asp<br>475 480 485 | 1492 |
| gct gat tgg gta gtt aaa atc atc gat ata ttt ccc gga gat cag cca<br>Ala Asp Trp Val Val Lys Ile Ile Asp Ile Phe Pro Gly Asp Gln Pro<br>490 495 500 | 1540 |
| aat cat gcc tat gtt tta gat ggg gtg gac atg ggc aat tac cac cta<br>Asn His Ala Tyr Val Leu Asp Gly Val Asp Met Gly Asn Tyr His Leu | 1588 |

```
                  505                 510                 515                 520
atg gtt cgt tca gag gta att aga ggg agg tat aga gaa agt ttt gag             1636
Met Val Arg Ser Glu Val Ile Arg Gly Arg Tyr Arg Glu Ser Phe Glu
            525                 530                 535 ttt cct aaa ccc ttt gtt cct gat caa atc act gct gtt gat ttc agg             1684
Phe Pro Lys Pro Phe Val Pro Asp Gln Ile Thr Ala Val Asp Phe Arg
        540                 545                 550 tta caa gat ctt ttc cat act ttc aaa aag ggg cat aaa att caa ata             1732
Leu Gln Asp Leu Phe His Thr Phe Lys Lys Gly His Lys Ile Gln Ile
    555                 560                 565 caa ata caa agt act tgg ttt ccc cta att gat cga aat ccc caa aaa             1780
Gln Ile Gln Ser Thr Trp Phe Pro Leu Ile Asp Arg Asn Pro Gln Lys
570                 575                 580 tat gta caa aac ata ttt gaa gct gag gaa gcc gat ttt gtc aaa gcc             1828
Tyr Val Gln Asn Ile Phe Glu Ala Glu Glu Ala Asp Phe Val Lys Ala
585                 590                 595                 600 acc cat agg gtt ttt cat aca gaa aag ttt gcc agc aaa att gaa gta             1876
Thr His Arg Val Phe His Thr Glu Lys Phe Ala Ser Lys Ile Glu Val
            605                 610                 615 atg gtt ctt cct tagaattaga atggtttaaa attactattt gtagcagaag ata            1931
Met Val Leu Pro
            620

<210> SEQ ID NO 25
<211> LENGTH: 620
<212> TYPE: PRT
<213> ORGANISM: Cyclobacterium marinum

<400> SEQUENCE: 25

Met Lys His Cys Tyr Lys Leu Leu Val Phe Tyr Thr Leu Phe Leu Met
1               5                   10                  15

Thr Thr Asn Trp Ala Leu Ser Gln Ala Ile Asn Gly Tyr Asp Lys Ala
            20                  25                  30

Ala Tyr Asp Ile Pro Met Arg Asp Gly Val His Leu His Thr Ile Val
        35                  40                  45

Tyr Ser Pro Lys Asp Leu Ser Gln Pro Tyr Pro Ile Leu Met Gln Arg
    50                  55                  60

Thr Pro Tyr Ser Ala Gly Pro Tyr Gly Pro Gly Asn Met Lys Asn Lys
65                  70                  75                  80

Leu Gly Pro Ser Gln Phe Leu Met Asn Asp Gly Tyr Ile Phe Val Tyr
                85                  90                  95

Gln Asp Val Arg Gly Arg Trp Met Ser Glu Gly Ser Tyr Asp Asn Met
            100                 105                 110

Arg Pro Thr Leu Ser Lys Ser Glu Arg Asn Ser Asn Gln Ile Asp Glu
        115                 120                 125

Ser Thr Asp Thr Tyr Asp Thr Ile Glu Trp Leu Leu Ala Asn Ile Lys
    130                 135                 140

Asn His Asn Glu Lys Val Gly Leu Trp Gly Ile Ser Tyr Pro Gly Phe
145                 150                 155                 160

Tyr Ser Ala Ala Ala Leu Pro Phe Ala His Pro Asn Leu Lys Ala Val
                165                 170                 175

Ser Pro Gln Ala Pro Ile Gly Asp Phe Tyr Asp Asp Phe His His
            180                 185                 190

Asn Gly Ala Tyr Leu Leu Ser Tyr Trp Leu Ala Thr Ser Val Phe Gly
        195                 200                 205

Tyr Gln Lys Asp Gly Pro Thr Gln Glu Ala Trp Tyr Gly Met Val Asn
    210                 215                 220
```

-continued

```
Pro Glu Thr Asn Asp Gly Tyr Gln Phe Phe Met Asp Met Gly Pro Leu
225                 230                 235                 240

Lys Asn Ala Asp Lys Trp Tyr Gly Glu Asp Asn Phe Phe Trp Gln Gln
            245                 250                 255

Leu Lys Asn Asn Pro Asp Tyr Asn Ala Phe Trp Gln Lys Arg Ser Ile
            260                 265                 270

Ile Pro His Leu Lys Glu Val Lys Pro Ala Val Leu Thr Val Gly Gly
            275                 280                 285

Trp Phe Asp Ala Glu Asp Leu Tyr Gly Pro Leu Thr Ile Tyr Lys Thr
290                 295                 300

Ile Glu Lys Asn Asn Pro Glu Thr Tyr Asn Thr Ile Val Met Gly Pro
305                 310                 315                 320

Trp Ser His Gly Asp Trp Ser Arg Glu Pro Gly Ser Gln Val Ile Ser
            325                 330                 335

Asn Ile Tyr Phe Gly Asp Ser Ile Ser Thr Trp Tyr Gln Lys Asn Ile
            340                 345                 350

Glu Arg Val Phe Phe Asn His Phe Leu Lys Glu Ser Glu Asn Ser Asn
            355                 360                 365

Pro Ala Leu Pro Glu Ala Tyr Met Phe Asp Thr Gly Lys His Lys Trp
            370                 375                 380

Glu Lys Phe Asp Asp Trp Pro Lys Glu Ser Gln Trp Lys Ser Phe
385                 390                 395                 400

Tyr Phe Gln Glu Lys Gly Glu Leu Thr Glu Val Thr Pro Glu Gly Asn
                405                 410                 415

Arg Phe Thr Thr Tyr Val Ser Asp Pro Ser Asn Pro Val Pro Tyr Ser
            420                 425                 430

Gln Asp Ile Lys Leu Asn Phe Thr Pro Arg Lys Tyr Met Ala Asp Asp
            435                 440                 445

Gln Arg Phe Ala Ala Arg Pro Asp Val Leu Thr Phe Thr Ser Glu
450                 455                 460

Val Leu Ser Gln Asp Met Thr Leu Ala Gly Glu Val Met Ala Asn Leu
465                 470                 475                 480

Lys Val Ala Thr Ser Gln Thr Asp Ala Asp Trp Val Lys Ile Ile
            485                 490                 495

Asp Ile Phe Pro Gly Asp Gln Pro Asn His Ala Tyr Val Leu Asp Gly
            500                 505                 510

Val Asp Met Gly Asn Tyr His Leu Met Val Arg Ser Glu Val Ile Arg
            515                 520                 525

Gly Arg Tyr Arg Glu Ser Phe Glu Phe Pro Lys Pro Phe Val Pro Asp
530                 535                 540

Gln Ile Thr Ala Val Asp Phe Arg Leu Gln Asp Leu Phe His Thr Phe
545                 550                 555                 560

Lys Lys Gly His Lys Ile Gln Ile Gln Ile Gln Ser Thr Trp Phe Pro
            565                 570                 575

Leu Ile Asp Arg Asn Pro Gln Lys Tyr Val Gln Asn Ile Phe Glu Ala
            580                 585                 590

Glu Glu Ala Asp Phe Val Lys Ala Thr His Arg Val Phe His Thr Glu
            595                 600                 605

Lys Phe Ala Ser Lys Ile Glu Val Met Val Leu Pro
610                 615                 620

<210> SEQ ID NO 26
<211> LENGTH: 2036
```

```
<212> TYPE: DNA
<213> ORGANISM: Psycloserpens burtonensis
<220> FEATURE:
<221> NAME/KEY: CDS
<222> LOCATION: (61)..(1992)
<223> OTHER INFORMATION:

<400> SEQUENCE: 26
catattcgta aaatagctat aagtttttgt aaatttagtc aatcaaaatt ttaaatgtaa        60 atg aag act ctt ttt aaa ttg ttg ctc cta ttt gta ttt gtt cta acg        108
Met Lys Thr Leu Phe Lys Leu Leu Leu Leu Phe Val Phe Val Leu Thr
1               5                   10                  15 tct tgt aat aag gcc aac aaa gac gct act gaa att gtg aaa acc gaa        156
Ser Cys Asn Lys Ala Asn Lys Asp Ala Thr Glu Ile Val Lys Thr Glu
            20                  25                  30 gta gaa gat act tac gtt aaa gat aat tat aac aaa caa gag gtg act        204
Val Glu Asp Thr Tyr Val Lys Asp Asn Tyr Asn Lys Gln Glu Val Thr
        35                  40                  45 att gaa atg cgc gat ggt ata aaa ctt cac acg acc att tat tca cca        252
Ile Glu Met Arg Asp Gly Ile Lys Leu His Thr Thr Ile Tyr Ser Pro
    50                  55                  60 aaa gat gaa agt cag acc tat cct att tta atg atg aga aca cca tat        300
Lys Asp Glu Ser Gln Thr Tyr Pro Ile Leu Met Met Arg Thr Pro Tyr
65              70                  75                  80 agt tct caa cct tat ggt gac aat gag ttt aag acg aaa att ggt cct        348
Ser Ser Gln Pro Tyr Gly Asp Asn Glu Phe Lys Thr Lys Ile Gly Pro
                85                  90                  95 aat gtt cat tta atg aaa gaa ggg aat att gtt gtg tat caa gat gta        396
Asn Val His Leu Met Lys Glu Gly Asn Ile Val Val Tyr Gln Asp Val
            100                 105                 110 cga ggt cgt tgg atg agt gaa ggt gtc tat gat aat atg cgt gct tat        444
Arg Gly Arg Trp Met Ser Glu Gly Val Tyr Asp Asn Met Arg Ala Tyr
        115                 120                 125 atc cca aat aaa aca gag gat tct caa att gat gag gca tca gac act        492
Ile Pro Asn Lys Thr Glu Asp Ser Gln Ile Asp Glu Ala Ser Asp Thr
    130                 135                 140 tat gac acg att gac tgg ctg gta aat aac gta gaa aat aat aac ggg        540
Tyr Asp Thr Ile Asp Trp Leu Val Asn Asn Val Glu Asn Asn Asn Gly
145                 150                 155                 160 aat gtt ggt act tgg gga att tca tat cct ggt ttt tat gct aca tat        588
Asn Val Gly Thr Trp Gly Ile Ser Tyr Pro Gly Phe Tyr Ala Thr Tyr
                165                 170                 175 tct act ata gac gca cac cca gct tta aaa gca gca tcg cct caa gcg        636
Ser Thr Ile Asp Ala His Pro Ala Leu Lys Ala Ala Ser Pro Gln Ala
            180                 185                 190 tgt att gga gat ttc ttt ttt gac gat ttt cat cat aat ggt gct ttt        684
Cys Ile Gly Asp Phe Phe Phe Asp Asp Phe His His Asn Gly Ala Phe
        195                 200                 205 tta tta agt tat ttt aga gca gtg tct tta ttt ggt acg aca aaa gat        732
Leu Leu Ser Tyr Phe Arg Ala Val Ser Leu Phe Gly Thr Thr Lys Asp
    210                 215                 220 aaa cct aca gat tct gct tgg tat aag ttt cca gaa atg aaa aca caa        780
Lys Pro Thr Asp Ser Ala Trp Tyr Lys Phe Pro Glu Met Lys Thr Gln
225                 230                 235                 240 gat caa tat caa ttt ttt ctt gat gct gga cct tta agt aat ttg aac        828
Asp Gln Tyr Gln Phe Phe Leu Asp Ala Gly Pro Leu Ser Asn Leu Asn
                245                 250                 255 aag tat ttc caa tat gac aca cca gac gac aca tct gta tcc aag tct        876
Lys Tyr Phe Gln Tyr Asp Thr Pro Asp Asp Thr Ser Val Ser Lys Ser
            260                 265                 270
```

| | | |
|---|---|---|
| gat agg ata gat gat gtg ttt tgg aaa gaa att gta gag cat cca aac<br>Asp Arg Ile Asp Asp Val Phe Trp Lys Glu Ile Val Glu His Pro Asn<br>275                            280                         285 | 924 | |
| tac gat acg ata tgg aaa tct aaa ggt tta att caa aac cta aaa gat<br>Tyr Asp Thr Ile Trp Lys Ser Lys Gly Leu Ile Gln Asn Leu Lys Asp<br>        290                       295                       300 | 972 | |
| att aag cca agt gta gcg aca atg att gtg gga ggg tta ttt gat gcc<br>Ile Lys Pro Ser Val Ala Thr Met Ile Val Gly Gly Leu Phe Asp Ala<br>305                         310                        315                320 | 1020 | |
| gaa gat tta tat ggg cca ttt gaa act tat aaa acg ata gaa aaa cat<br>Glu Asp Leu Tyr Gly Pro Phe Glu Thr Tyr Lys Thr Ile Glu Lys His<br>                     325                       330                       335 | 1068 | |
| aat cct gat aat tat aat att atg gtt ttt ggg cct tgg gat cat ggt<br>Asn Pro Asp Asn Tyr Asn Ile Met Val Phe Gly Pro Trp Asp His Gly<br>                 340                       345                       350 | 1116 | |
| cgt tgg gct agg agt gac gtt aaa aat tat gtt gga aat tat ttc ttc<br>Arg Trp Ala Arg Ser Asp Val Lys Asn Tyr Val Gly Asn Tyr Phe Phe<br>                     355                       360                       365 | 1164 | |
| gga gat tct ata tct cta aaa ttt caa cgt gat gtt gaa acg aag ttt<br>Gly Asp Ser Ile Ser Leu Lys Phe Gln Arg Asp Val Glu Thr Lys Phe<br>370                         375                        380 | 1212 | |
| ttt aat cat ttt tta aaa gga aaa ggc gac aag aac tca ggg tta cca<br>Phe Asn His Phe Leu Lys Gly Lys Gly Asp Lys Asn Ser Gly Leu Pro<br>385                         390                        395                400 | 1260 | |
| gaa gca tat gta ttt gat tct ggt aaa aag gaa tgg agt agc ttt gac<br>Glu Ala Tyr Val Phe Asp Ser Gly Lys Lys Glu Trp Ser Ser Phe Asp<br>                     405                       410                       415 | 1308 | |
| agc tgg cct cca aag caa gca gaa aaa caa gcc atg tat ctt aat gcc<br>Ser Trp Pro Pro Lys Gln Ala Glu Lys Gln Ala Met Tyr Leu Asn Ala<br>                 420                       425                       430 | 1356 | |
| aac caa gag cta tca gat tca aaa aaa gga aat act agt gag aca ttt<br>Asn Gln Glu Leu Ser Asp Ser Lys Lys Gly Asn Thr Ser Glu Thr Phe<br>                     435                       440                       445 | 1404 | |
| gtt agt gat tta aaa cgc cct gta cct tat tcc gaa gat att aaa aca<br>Val Ser Asp Leu Lys Arg Pro Val Pro Tyr Ser Glu Asp Ile Lys Thr<br>450                         455                        460 | 1452 | |
| gtt ttc aca cca cga aaa tac atg aca gac gat cag cgt ttt gca gca<br>Val Phe Thr Pro Arg Lys Tyr Met Thr Asp Asp Gln Arg Phe Ala Ala<br>465                         470                       475                480 | 1500 | |
| cga cgt cct gat gtt ctt ata ttt gag acc gat att ctt gag gaa gat<br>Arg Arg Pro Asp Val Leu Ile Phe Glu Thr Asp Ile Leu Glu Glu Asp<br>                     485                       490                       495 | 1548 | |
| ata acc tta gct ggt gat att tta gcg cag ctt aat gtg tca act aca<br>Ile Thr Leu Ala Gly Asp Ile Leu Ala Gln Leu Asn Val Ser Thr Thr<br>                 500                       505                       510 | 1596 | |
| ggg aca gat gca gat tgg att gtc aaa ata gta gat gtt cat cca gca<br>Gly Thr Asp Ala Asp Trp Ile Val Lys Ile Val Asp Val His Pro Ala<br>               515                       520                       525 | 1644 | |
| gat gct gag gag caa aaa gaa ggt atg caa gac cat tta tca atg agt<br>Asp Ala Glu Glu Gln Lys Glu Gly Met Gln Asp His Leu Ser Met Ser<br>530                         535                        540 | 1692 | |
| aat tat cat ttg atg gtg agg agt gaa gtg atg cgc ggt cgt ttt aga<br>Asn Tyr His Leu Met Val Arg Ser Glu Val Met Arg Gly Arg Phe Arg<br>545                         550                       555                560 | 1740 | |
| aat agt ttt gaa aac cca gag cca ttt gtg cca aac caa cca aca gat<br>Asn Ser Phe Glu Asn Pro Glu Pro Phe Val Pro Asn Gln Pro Thr Asp<br>                     565                       570                       575 | 1788 | |
| gtc aat atc aag tta caa gat gta cat cat aca ttt aaa aaa ggt cac<br>Val Asn Ile Lys Leu Gln Asp Val His His Thr Phe Lys Lys Gly His<br>                 580                       585                       590 | 1836 | |

-continued

```
aaa tta caa gtg caa gtt cag agt acg tgg ttt cca ctt att gat ttg   1884
Lys Leu Gln Val Gln Val Gln Ser Thr Trp Phe Pro Leu Ile Asp Leu
            595             600             605 aac ccg caa aca ttt gtg cct aat att tat aaa gca aaa gaa agc gat   1932
Asn Pro Gln Thr Phe Val Pro Asn Ile Tyr Lys Ala Lys Glu Ser Asp
610             615             620 ttt aaa acc caa aca cat tcg gtt ttt aac gat tct aaa att gag ttt   1980
Phe Lys Thr Gln Thr His Ser Val Phe Asn Asp Ser Lys Ile Glu Phe
625             630             635             640 acg gtt ttg aaa taagagtaga tgactaaatt tgccaaggta gatttagtct tttt  2036
Thr Val Leu Lys
```

<210> SEQ ID NO 27
<211> LENGTH: 644
<212> TYPE: PRT
<213> ORGANISM: Psycloserpens burtonensis

<400> SEQUENCE: 27

```
Met Lys Thr Leu Phe Lys Leu Leu Leu Phe Val Phe Val Leu Thr
1               5                   10                  15

Ser Cys Asn Lys Ala Asn Lys Asp Ala Thr Glu Ile Val Lys Thr Glu
            20                  25                  30

Val Glu Asp Thr Tyr Val Lys Asp Asn Tyr Asn Lys Gln Glu Val Thr
        35                  40                  45

Ile Glu Met Arg Asp Gly Ile Lys Leu His Thr Thr Ile Tyr Ser Pro
    50                  55                  60

Lys Asp Glu Ser Gln Thr Tyr Pro Ile Leu Met Met Arg Thr Pro Tyr
65                  70                  75                  80

Ser Ser Gln Pro Tyr Gly Asp Asn Glu Phe Lys Thr Lys Ile Gly Pro
                85                  90                  95

Asn Val His Leu Met Lys Glu Gly Asn Ile Val Val Tyr Gln Asp Val
            100                 105                 110

Arg Gly Arg Trp Met Ser Glu Gly Val Tyr Asp Asn Met Arg Ala Tyr
        115                 120                 125

Ile Pro Asn Lys Thr Glu Asp Ser Gln Ile Asp Glu Ala Ser Asp Thr
    130                 135                 140

Tyr Asp Thr Ile Asp Trp Leu Val Asn Asn Val Glu Asn Asn Gly
145                 150                 155                 160

Asn Val Gly Thr Trp Gly Ile Ser Tyr Pro Gly Phe Tyr Ala Thr Tyr
                165                 170                 175

Ser Thr Ile Asp Ala His Pro Ala Leu Lys Ala Ala Ser Pro Gln Ala
            180                 185                 190

Cys Ile Gly Asp Phe Phe Phe Asp Asp Phe His His Asn Gly Ala Phe
        195                 200                 205

Leu Leu Ser Tyr Phe Arg Ala Val Ser Leu Phe Gly Thr Thr Lys Asp
    210                 215                 220

Lys Pro Thr Asp Ser Ala Trp Tyr Lys Phe Pro Glu Met Lys Thr Gln
225                 230                 235                 240

Asp Gln Tyr Gln Phe Phe Leu Asp Ala Gly Pro Leu Ser Asn Leu Asn
                245                 250                 255

Lys Tyr Phe Gln Tyr Asp Thr Pro Asp Asp Thr Ser Val Ser Lys Ser
            260                 265                 270

Asp Arg Ile Asp Asp Val Phe Trp Lys Glu Ile Val Glu His Pro Asn
        275                 280                 285

Tyr Asp Thr Ile Trp Lys Ser Lys Gly Leu Ile Gln Asn Leu Lys Asp
```

-continued

```
                290                 295                 300
Ile Lys Pro Ser Val Ala Thr Met Ile Val Gly Gly Leu Phe Asp Ala
305                 310                 315                 320
Glu Asp Leu Tyr Gly Pro Phe Glu Thr Tyr Lys Thr Ile Glu Lys His
                325                 330                 335
Asn Pro Asp Asn Tyr Asn Ile Met Val Phe Gly Pro Trp Asp His Gly
                340                 345                 350
Arg Trp Ala Arg Ser Asp Val Lys Asn Tyr Val Gly Asn Tyr Phe Phe
                355                 360                 365
Gly Asp Ser Ile Ser Leu Lys Phe Gln Arg Asp Val Glu Thr Lys Phe
                370                 375                 380
Phe Asn His Phe Leu Lys Gly Lys Gly Asp Lys Asn Ser Gly Leu Pro
385                 390                 395                 400
Glu Ala Tyr Val Phe Asp Ser Gly Lys Lys Glu Trp Ser Ser Phe Asp
                405                 410                 415
Ser Trp Pro Pro Lys Gln Ala Glu Lys Gln Ala Met Tyr Leu Asn Ala
                420                 425                 430
Asn Gln Glu Leu Ser Asp Ser Lys Lys Gly Asn Thr Ser Glu Thr Phe
                435                 440                 445
Val Ser Asp Leu Lys Arg Pro Val Pro Tyr Ser Glu Asp Ile Lys Thr
450                 455                 460
Val Phe Thr Pro Arg Lys Tyr Met Thr Asp Asp Gln Arg Phe Ala Ala
465                 470                 475                 480
Arg Arg Pro Asp Val Leu Ile Phe Glu Thr Asp Ile Leu Glu Glu Asp
                485                 490                 495
Ile Thr Leu Ala Gly Asp Ile Leu Ala Gln Leu Asn Val Ser Thr Thr
                500                 505                 510
Gly Thr Asp Ala Asp Trp Ile Val Lys Ile Val Asp Val His Pro Ala
                515                 520                 525
Asp Ala Glu Glu Gln Lys Glu Gly Met Gln Asp His Leu Ser Met Ser
                530                 535                 540
Asn Tyr His Leu Met Val Arg Ser Glu Val Met Arg Gly Arg Phe Arg
545                 550                 555                 560
Asn Ser Phe Glu Asn Pro Glu Pro Phe Val Pro Asn Gln Pro Thr Asp
                565                 570                 575
Val Asn Ile Lys Leu Gln Asp Val His His Thr Phe Lys Lys Gly His
                580                 585                 590
Lys Leu Gln Val Gln Val Gln Ser Thr Trp Phe Pro Leu Ile Asp Leu
                595                 600                 605
Asn Pro Gln Thr Phe Val Pro Asn Ile Tyr Lys Ala Lys Glu Ser Asp
                610                 615                 620
Phe Lys Thr Gln Thr His Ser Val Phe Asn Asp Ser Lys Ile Glu Phe
625                 630                 635                 640
Thr Val Leu Lys
```

PEPTIDE-FORMING ENZYME GENE

CROSS-REFERENCE TO RELATED APPLICATIONS

The present application is a division of U.S. Ser. No. 11/841,151, filed on Aug. 20, 2007, which is a divisional of U.S. Ser. No. 10/855,533, filed on May 28, 2004, which is a continuation of PCT/JP03/09468 filed on Jul. 25, 2003, which claims priority to JP 2003-16765, filed on Jan. 24, 2003, and to JP 2002-218957, filed on Jul. 26, 2002.

TECHNICAL FIELD

The present invention relates to a novel enzyme that can form a peptide easily, at high yield and inexpensively without going through a complex synthetic method. More particularly, the present invention relates to a novel enzyme that catalyzes a peptide-forming reaction from a carboxy component and an amine component, to a microbe that produces the enzyme, and to a method for producing dipeptide using this enzyme or microbe.

BACKGROUND ART

Peptides are used in the fields of pharmaceuticals, foods and various other fields. For example, since L-alanyl-L-glutamine has higher stability and water-solubility than L-glutamine, it is widely used as a component of fluid infusion and serum-free media.

Chemical synthesis methods, which have been known as methods for producing peptides, are not always easy. Known examples of such methods include a method that uses N-benzyloxycarbonylalanine (hereinafter, "Z-alanine") and protected L-glutamine (see Bull. Chem. Soc. Jpn., 34, 739 (1961), Bull. Chem. Soc. Jpn., 35, 1966 (1962)), a method that uses Z-alanine and protected L-glutamic acid-γ-methyl ester (see Bull. Chem. Soc. Jpn., 37, 200 (1964)), a method that uses Z-alanine ester and unprotected glutamic acid (see Japanese Patent Application Laid-open Publication No. H1-96194), a method that involves synthesis of an N-(2-substituted)-propionyl glutamine derivative as an intermediate from a 2-substituted-propionyl halide as a raw material (see Patent Application Laid-open Publication No. H6-234715).

However, since all these methods require the introduction and elimination of protecting groups or the use of an optically active intermediate, they are not considered to be adequately satisfactory in terms of their industrial advantages.

On the other hand, widely known examples of typical peptide production methods using enzymes consist of a condensation reaction that uses an N-protected and C-unprotected carboxy component and an N-unprotected, C-protected amine component (hereinafter, "Reaction 1"), and a substitution reaction that uses an N-protected, C-protected carboxy component and an N-unprotected, C-protected amine component (hereinafter, "Reaction 2"). An example of Reaction 1 is a method for producing Z-aspartylphenylalanine methyl ester from Z-aspartic acid and phenylalanine methyl ester (see Japanese Patent Application Laid-open Publication No. S53-92729), while an example of Reaction 2 is a method for producing acetylphenylalanylleucine amide from acetylphenylalanine ethyl ester and leucine amide (see Biochemical J., 163, 531 (1977)). There have been reported very few research examples of method that uses an N-unprotected, C-protected carboxy component. An example of a substitution reaction that uses an N-unprotected, C-protected carboxy component and an N-unprotected, C-protected amine component (hereinafter, "Reaction 3") is described in International Patent Publication WO 90/01555. For example, a method for producing arginylleucine amide from arginine ethyl ester and leucine amide may be mentioned of. Examples of substitution reactions that use an N-unprotected, C-protected carboxy component and an N-unprotected, C-unprotected amine component (hereinafter, "Reaction 4") are described in European Patent Publication EP 278787A1 and European Patent Publication EP 359399B1. For example, a method for producing tyrosylalanine from tyrosine ethyl ester and alanine amide may be mentioned of.

DISCLOSURE OF THE INVENTION

The most inexpensive production method among the aforementioned methods of Reactions 1 to 4 naturally falls within the class of Reaction 4, which involves the fewest protecting groups.

However, the example of Reaction 4 of the prior art (see European Patent Publication EP 278787A1) had the following major problems: (1) extremely slow rate of peptide production, (2) low peptide production yield, (3) the peptides that can be produced are limited to those that contain amino acids with comparatively high hydrophobicity, (4) the amount of enzyme added is extremely large, and (5) comparatively expensive carboxypeptidase preparations derived from molds, yeasts or plants are required. In the Reaction 4, there is no method known whatsoever that uses an enzyme derived from bacteria or yeasts other than the genus *Saccharomyces*, and there are no known method for producing alanylglutamine and other peptides that are highly hydrophilic. In consideration of this background, there is a need to develop an industrially inexpensive method for producing these peptides.

It is an object of the present invention to provide a novel enzyme that can form a peptide easily, at high yield and inexpensively without going through a complex synthesis method. More particularly, an object of the present invention is to provide a novel enzyme that catalyzes a peptide-forming reaction from a carboxy component and an amine component, a microbe that produces the enzyme, and a method for inexpensively producing a peptide using this enzyme or microbe.

As a result of conducting extensive research in consideration of the above object, the inventors of the present invention have found a novel enzyme that efficiently forms a peptide from newly discovered bacteria belonging to the genus *Empedobacter*, etc. and determined the sequence of this enzyme gene, thereby leading to completion of the present invention.

Namely, the present invention is as described below.

[1] A DNA encoding a protein selected from the group consisting of (A), (C), (E), (G), (I), (K), (M), (O), (Q), (S), (U), and (W), wherein the protein has an amino acid sequence defined as follows:

(A) an amino acid sequence consisting of amino acid residue numbers 23 to 616 of SEQ ID NO:6, (C) an amino acid sequence consisting of amino acid residue numbers 21 to 619 of SEQ ID NO:12, (E) an amino acid sequence consisting of amino acid residue numbers 23 to 625 of SEQ ID NO:18, (G) an amino acid sequence consisting of amino acid residue numbers 23 to 645 of SEQ ID NO:23, (I) an amino acid sequence consisting of amino acid residue numbers 26 to 620 of SEQ ID NO:25, (K) an amino acid sequence consisting of amino acid residue numbers 18 to 644 of SEQ ID NO:27,
(M) an amino acid sequence consisting of SEQ ID NO:6,
(O) an amino acid sequence consisting of SEQ ID NO:12,
(Q) an amino acid sequence consisting of SEQ ID NO:18,
(S) an amino acid sequence consisting of SEQ ID NO:23,
(U) an amino acid sequence consisting of SEQ ID NO:25, or
(W) an amino acid sequence consisting of SEQ ID NO:27,

[2] A recombinant DNA including the DNA according to [1] above.

[3] A transformed cell including the recombinant DNA according to [2] above.

[4] A method for producing a peptide-forming enzyme including:
culturing the transformed cell according to [3] above in a medium for a time and under conditions suitable to produce the peptide-forming enzyme, and
accumulating the peptide-forming enzyme in the medium and/or transformed cell.

[5] A method for producing a dipeptide including:
culturing the transformed cell according to [3] in a medium for a time and under conditions suitable to produce a peptide-forming enzyme in a culture, and
mixing the culture with a carboxy component and an amine component to synthesize a dipeptide by enzymatic catalysis facilitated by a peptide-forming enzyme encoded by the DNA.

[6] The method for producing a dipeptide according to [5] above, wherein the cell is a microbe belonging to the genus *Sphingobacterium* that has an ability to form the dipeptide from the carboxy component and the amine component.

[7] The method for producing a dipeptide according to [6] above, wherein the cell is separated from the culture.

[8] The method for producing a dipeptide according to [6] above, wherein the cell is a treated microbial cell product of the microbe.

[9] A DNA encoding a protein selected from the group consisting of (B), (D), (F), (H), (J), (L), (N), (P), (R), (T), (V), and (X), wherein the protein has an amino acid sequence defined as follows:

(B) an amino acid sequence including substitution, deletion, insertion, addition, and/or inversion of one or a plurality of amino acids in amino acid residue numbers 23 to 616 of SEQ ID NO:6, and has at least 50% of the peptide-forming activity of a protein corresponding to unmutated amino acid residue numbers 23 to 616 of SEQ ID NO:6 at 50° C. and a pH of 8, (D) an amino acid sequence including substitution, deletion, insertion, addition, and/or inversion of one or a plurality of amino acids in amino acid residue numbers 21 to 619 of SEQ ID NO:12, and has at least 50% of the peptide-forming activity of a protein corresponding to unmutated amino acid residue numbers 21 to 619 of SEQ ID NO:12 at 50° C. and a pH of 8, (F) an amino acid sequence including substitution, deletion, insertion, addition, and/or inversion of one or a plurality of amino acids in amino acid residue numbers 23 to 625 of SEQ ID NO:18, and has at least 50% of the peptide-forming activity of a protein corresponding to unmutated amino acid residue numbers 23 to 625 of SEQ ID NO:18 at 50° C. and a pH of 8, (H) an amino acid sequence including substitution, deletion, insertion, addition, and/or inversion of one or a plurality of amino acids in amino acid residue numbers 23 to 645 of SEQ ID NO:23, and has at least 50% of the peptide-forming activity of a protein corresponding to unmutated amino acid residue numbers 23 to 645 of SEQ ID NO:23 at 50° C. and a pH of 8, (J) an amino acid sequence including substitution, deletion, insertion, addition, and/or inversion of one or a plurality of amino acids in amino acid residue numbers 26 to 620 of SEQ ID NO:25, and has at least 50% of the peptide-forming activity of a protein corresponding to unmutated amino acid residue numbers 26 to 620 of SEQ ID NO:25 at 50° C. and a pH of 8, (L) an amino acid sequence including substitution, deletion, insertion, addition, and/or inversion of one or a plurality of amino acids in amino acid residue numbers 18 to 644 of SEQ ID NO:27, and has at least 50% of the peptide-forming activity of a protein corresponding to unmutated amino acid residue numbers 18 to 644 of SEQ ID NO:27 at 50° C. and a pH of 8, (N) a mature protein region, having an amino acid sequence including substitution, deletion, insertion, addition, and/or inversion of one or a plurality of amino acids in an amino acid sequence consisting of SEQ ID NO:6, and has at least 50% of the peptide-forming activity of a protein corresponding to unmutated SEQ ID NO:6 at 50° C. and a pH of 8, (P) a mature protein region, having an amino acid sequence including substitution, deletion, insertion, addition, and/or inversion of one or a plurality of amino acids in an amino acid sequence consisting of SEQ ID NO:12, and has at least 50% of the peptide-forming activity of a protein corresponding to unmutated SEQ ID NO:12 at 50° C. and a pH of 8, (R) a mature protein region, having an amino acid sequence including substitution, deletion, insertion, addition, and/or inversion of one or a plurality of amino acids in an amino acid sequence consisting of SEQ ID NO:18, and has at least 50% of the peptide-forming activity of a protein corresponding to unmutated SEQ ID NO:18 at 50° C. and a pH of 8, (T) a mature protein region, having an amino acid sequence including substitution, deletion, insertion, addition, and/or inversion of one or a plurality of amino acids in an amino acid sequence consisting of SEQ ID NO:23, and has at least 50% of the peptide-forming activity of a protein corresponding to unmutated SEQ ID NO:23 at 50° C. and a pH of 8, (V) a mature protein region, having an amino acid sequence including substitution, deletion, insertion, addition, and/or inversion of one or a plurality of amino acids in an amino acid sequence consisting of SEQ ID NO:25, and has at least 50% of the peptide-forming activity of a protein corresponding to unmutated SEQ ID NO:25 at 50° C. and a pH of 8, or (X) a mature protein region, having an amino acid sequence including substitution, deletion, insertion, addition, and/or inversion of one or a plurality of amino acids in an amino acid sequence consisting of SEQ ID NO:27, and has at least 50% of the peptide-forming activity of a protein corresponding to unmutated SEQ ID NO:27 at 50° C. and a pH of 8.

[10] The DNA according to [9] above, wherein the plurality is 2 to 50 amino acid residues.

[11] A recombinant DNA including the DNA according to [9] above.

[12] A transformed cell including the recombinant DNA according to [11] above.

[13] A method for producing a peptide-forming enzyme including:
culturing the transformed cell according to [12] above, in a medium for a time and under conditions suitable to produce the peptide-forming enzyme, and
accumulating the peptide-forming enzyme in the medium and/or transformed cell.

[14] A method for producing a dipeptide including:
culturing the transformed cell according to [12] above in a medium for a time and under conditions suitable to produce a peptide-forming enzyme in a culture, and
mixing the culture with a carboxy component and an amine component to synthesize a dipeptide by enzymatic catalysis facilitated by a peptide-forming enzyme encoded by the DNA.

[15] The method for producing a dipeptide according to [14] above, wherein the cell is a microbe belonging to the genus *Sphingobacterium* that has an ability to form the dipeptide from the carboxy component and the amine component.

[16] The method for producing a dipeptide according to [15] above, wherein the cell is separated from the culture.

[17] The method for producing a dipeptide according to [15] above, wherein the cell is a treated microbial cell product of the microbe.

[18] A DNA selected from the group consisting of (a), (c), (e), (g), (i), (k), (m), (O), (q), (s), (u), and (w), wherein the DNA has a base sequence defined as follows:
(a) a base sequence consisting of base numbers 127 to 1908 of SEQ ID NO:5,
(c) a base sequence consisting of base numbers 121 to 1917 of SEQ ID NO:11,
(e) a base sequence consisting of base numbers 127 to 1935 of SEQ ID NO:17,
(g) a base sequence consisting of base numbers 127 to 1995 of SEQ ID NO:22,
(i) a base sequence consisting of base numbers 104 to 1888 of SEQ ID NO:24,
(k) a base sequence consisting of base numbers 112 to 1992 of SEQ ID NO:26,
(m) a base sequence consisting of base numbers 61 to 1908 of SEQ ID NO:5,
(o) a base sequence consisting of base numbers 61 to 1917 of SEQ ID NO:11,
(q) a base sequence consisting of base numbers 61 to 1935 of SEQ ID NO:17,
(s) a base sequence consisting of base numbers 61 to 1995 of SEQ ID NO:22,
(u) a base sequence consisting of base numbers 29 to 1888 of SEQ ID NO:24, or
(w) a base sequence consisting of base numbers 61 to 1992 of SEQ ID NO:26.

[19] A recombinant DNA including the DNA according to [18] above.

[20] A transformed cell including the recombinant DNA according to [19] above.

[21] A method for producing a peptide-forming enzyme including:
culturing the transformed cell according to [20] in a medium for a time and under conditions suitable to produce the peptide-forming enzyme, and
accumulating the peptide-forming enzyme in the medium and/or transformed cell.

[22] A method for producing a dipeptide including:
culturing the transformed cell according to [20] in a medium for a time and under conditions suitable to produce a peptide-forming enzyme in a culture, and
mixing the culture with a carboxy component and an amine component to synthesize a dipeptide by enzymatic catalysis facilitated by a peptide-forming enzyme encoded by the DNA.

[23] The method for producing a dipeptide according to [22] above, wherein the cell is a microbe belonging to the genus *Sphingobacterium* that has an ability to form the dipeptide from the carboxy component and the amine component.

[24] The method for producing a dipeptide according to [23], wherein the cell is separated from the culture.

[25] The method for producing a dipeptide according to [23], wherein the cell is a treated microbial cell product of the microbe.

[26] A DNA selected from the group consisting of (b), (d), (f, (h), (j), (l), (n), (p), (r), (t), (v), and (x), wherein the DNA has a base sequence defined as follows:
(b) a base sequence that hybridizes under stringent conditions with a DNA having a base sequence complementary to a base sequence consisting of base numbers 127 to 1908 of SEQ ID NO:5, and encodes a protein that has at least 50% of the peptide-forming activity at 50° C. and a pH of 8 of a protein encoded by unmutated base numbers 127 to 1908 of SEQ ID NO:5,
(d) a base sequence that hybridizes under stringent conditions with a DNA having a base sequence complementary to a base sequence consisting of base numbers 121 to 1917 of SEQ ID NO:11, and encodes a protein that has at least 50% of the peptide-forming activity at 50° C. and a pH of 8 of a protein encoded by unmutated base numbers 121 to 1917 of SEQ ID NO:11,
(f) a base sequence that hybridizes under stringent conditions with a DNA having a base sequence complementary to a base sequence consisting of base numbers 127 to 1935 of SEQ ID NO:17, and encodes a protein that has at least 50% of the peptide-forming activity at 50° C. and a pH of 8 of a protein encoded by unmutated base numbers 127 to 1935 of SEQ ID NO:17,
(h) a base sequence that hybridizes under stringent conditions with a DNA having a base sequence complementary to a base sequence consisting of base numbers 127 to 1995 of SEQ ID NO:22, and encodes a protein that has at least 50% of the peptide-forming activity at 50° C. and a pH of 8 of a protein encoded by unmutated base numbers 127 to 1995 of SEQ ID NO:22,
(j) a base sequence that hybridizes under stringent conditions with a DNA having a base sequence complementary to a base sequence consisting of base numbers 104 to 1888 of SEQ ID NO:24, and encodes a protein that has at least 50% of the peptide-forming activity at 50° C. and a pH of 8 of a protein encoded by unmutated base numbers 104 to 1888 of SEQ ID NO:24,
(l) a base sequence that hybridizes under stringent conditions with a DNA having a base sequence complementary to a base sequence consisting of base numbers 112 to 1992 of SEQ ID NO:26, and encodes a protein that has at least 50% of the peptide-forming activity at 50° C. and a pH of 8 of a protein encoded by unmutated base numbers 112 to 1992 of SEQ ID NO:26,
(n) a base sequence that hybridizes under stringent conditions with a DNA having a base sequence complementary to a base sequence consisting of base numbers 61 to 1908 of SEQ ID NO:5, and encodes a protein that has at least 50% of the peptide-forming activity at 50° C. and a pH of 8 of a protein encoded by unmutated base numbers 61 to 1908 of SEQ ID NO:5, (p) a base sequence that hybridizes under stringent conditions with a DNA having a base sequence complementary to a base sequence consisting of base numbers 61 to 1917 of SEQ ID NO:11, and encodes a protein that has at least 50% of the peptide-forming activity at 50° C. and a pH of 8 of a protein encoded by unmutated base numbers 61 to 1917 of SEQ ID NO:11, (r) a base sequence that hybridizes under stringent conditions with a DNA having a base sequence complementary to a base sequence consisting of base numbers 61 to 1935 of SEQ ID NO:17, and encodes a protein that has at least 50% of the peptide-forming activity at 50° C. and a pH of 8 of a protein encoded by unmutated base numbers 61 to 1935 of SEQ ID NO:17, (t) a base sequence that hybridizes under stringent conditions with a DNA having a base sequence complementary to a base sequence consisting of base numbers 61 to 1995 of SEQ ID NO:22, and encodes a protein that has at least 50% of the peptide-forming activity at 50° C. and a pH of 8 of a protein encoded by unmutated base numbers 61 to 1995 of SEQ ID NO:22, (v) a base sequence that hybridizes under stringent conditions with a DNA having a base sequence complementary to a base sequence consisting of base numbers 29 to 1888 of SEQ ID NO:24, and encodes a protein that has at least 50% of the peptide-forming activity at 50° C. and a pH of 8 of a protein encoded by unmutated base numbers 29 to 1888 of SEQ ID NO:24, or (x) a base sequence that hybridizes under stringent conditions with a DNA having a base sequence complementary to a base sequence consisting of base numbers 61 to 1992 of SEQ ID NO:26, and encodes a protein that has at least 50% of the peptide-forming activity at 50° C. and a pH of 8 of a protein encoded by unmutated base numbers 61 to 1992 of SEQ ID NO:26.

[27] A recombinant DNA including the DNA according to [26] above.

[28] A transformed cell including the recombinant DNA according to [26] above.

[29] A method for producing a peptide-forming enzyme including:
culturing the transformed cell according to [28] in a medium for a time and under conditions suitable to produce the peptide-forming enzyme, and
accumulating the peptide-forming enzyme in the medium and/or transformed cell.

[30] A method for producing a dipeptide including:
culturing the transformed cell according to [28] in a medium for a time and under conditions suitable to produce a peptide-forming enzyme in a culture, and
mixing the culture with a carboxy component and an amine component to synthesize a dipeptide by enzymatic catalysis facilitated by a peptide-forming enzyme encoded by the DNA.

[31] The method for producing a dipeptide according to [30] above, wherein the cell is a microbe belonging to the genus *Sphingobacterium* that has an ability to form the dipeptide from the carboxy component and the amine component.

[32] The method for producing a dipeptide according to [31] above, wherein the cell is separated from the culture.

[33] The method for producing a dipeptide according to [31] above, wherein the cell is a treated microbial cell product of the microbe.

[34] The DNA according to [26] above, wherein stringent conditions are conditions under which washing is carried out at 60° C. at a salt concentration equivalent to 1×SSC and 0.1% SDS.

[35] A recombinant DNA including the DNA according to [34].

[36] A transformed cell including the recombinant DNA according to [35].

[37] A method for producing a peptide-forming enzyme including:
culturing the transformed cell according to [36] in a medium from a time and under conditions suitable to produce the peptide-forming enzyme, and
accumulating the peptide-forming enzyme in the medium and/or transformed cell.

[38] A method for producing a dipeptide including:
culturing the transformed cell according to [36] in a medium and under conditions suitable to produce a dipeptide-forming enzyme in a culture, and
mixing the culture with a carboxy component and an amine component to synthesize a dipeptide by enzymatic catalysis facilitated by a peptide-forming enzyme encoded by the DNA.

Furthermore, the amino acid sequence described in SEQ ID NO: 6 is specified by the DNA described in SEQ ID NO: 5 of the Sequence Listing. The amino acid sequence described in SEQ ID NO: 12 is specified by the DNA described in SEQ ID NO: 11. The amino acid sequence described in SEQ ID NO: 18 is specified by the DNA described in SEQ ID NO: 17. The amino acid sequence described in SEQ ID NO: 23 is specified by the DNA described in SEQ ID NO: 22. The amino acid sequence described in SEQ ID NO: 25 is specified by the DNA described in SEQ ID NO: 24. The amino acid sequence described in SEQ ID NO: 27 is specified by the DNA described in SEQ ID NO: 26.

BEST MODE FOR CARRYING OUT THE INVENTION

Figure 1:
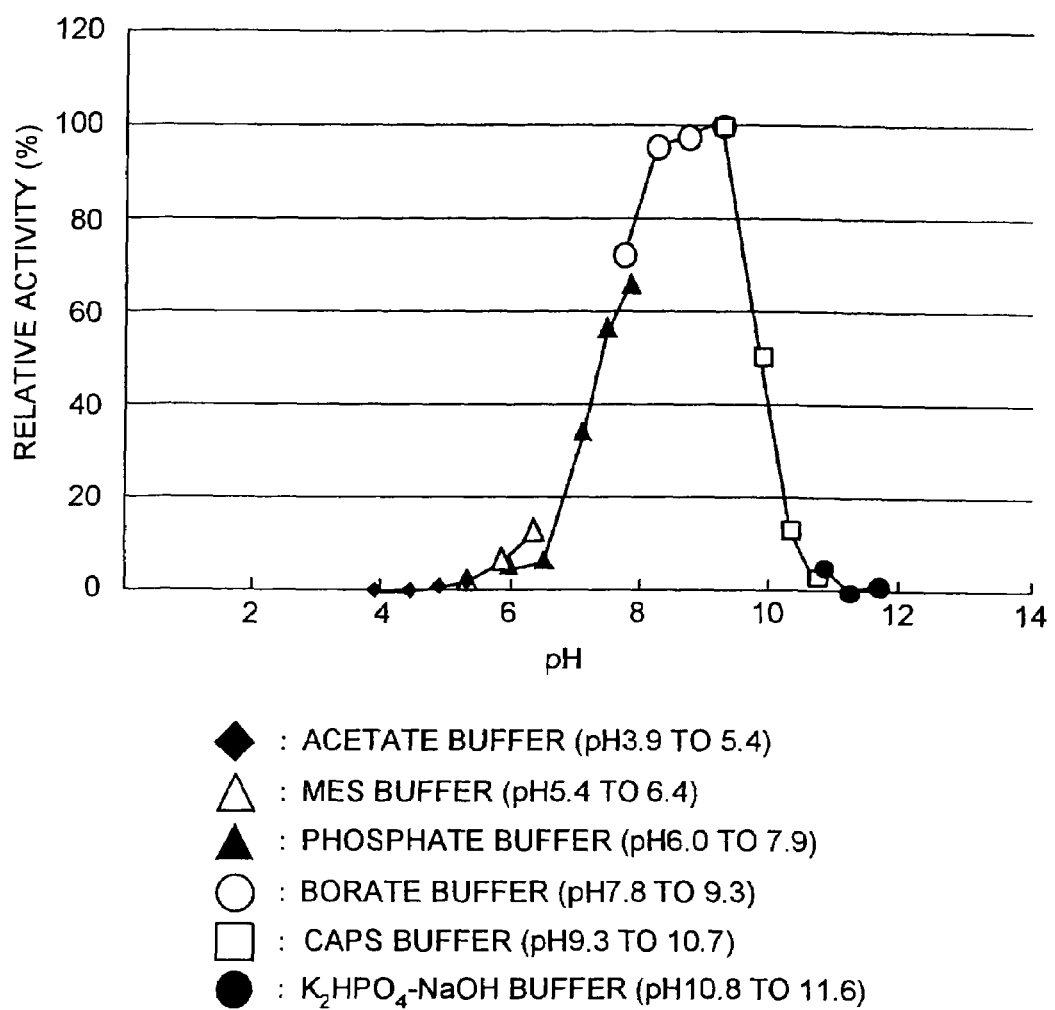
FIG. 1 is a graph illustrating the optimum pH of the enzyme of *Empedobacter* of the present invention.

Hereinafter, the novel dipeptide-forming enzyme gene of the present invention and the dipeptide-forming enzyme that is the product of that gene.

(1) Microbes Harboring the DNA of the Present Invention

The DNA of the present invention encodes a protein having the ability to form a peptide from a carboxy component and an amine component. In the present specification, a carboxy component refers to a component that provides a carbonyl site (CO) in a peptide bond (—CONH—), while an amine component refers to a component that provides an amino site (NH) in a peptide bond. In addition, in the present specification, unless otherwise indicated specifically, the term "peptide" when used alone refers to a polymer having at least one peptide bond. In addition, in the present specification, "dipeptide" refers to a peptide having one peptide bond.

Examples of microbes harboring the DNA of the present invention include bacteria belonging to the genus *Empedobacter*, genus *Sphingobacterium*, genus *Pedobacter*, genus *Taxeobacter*, genus *Cyclobacterium* or genus *Psycloserpens*, while more specific examples thereof include *Empedobacter brevis* strain ATCC 14234 (strain FERM P-18545, strain FERM BP-8113), *Sphingobacterium* sp. strain FERM BP-8124, *Pedobacter heparinus* strain IFO 12017, *Taxeobacter gelupurpurascens* strain DSMZ 11116, *Cyclobacterium marinum* strain ATCC 25205 and *Psycloserpens burtonensis* strain ATCC 700359. *Empedobacter brevis* strain ATCC 14234 (strain FERM P-18545, strain FERM BP-8113), *Sphingobacterium* sp. strain FERM BP-8124, *Pedobacter heparinus* strain IFO 12017, *Taxeobacter gelupurpurascens* strain DSMZ 11116, *Cyclobacterium marinum* strain ATCC 25205 and *Psycloserpens burtonensis* strain ATCC 700359 are microbes that were selected as a result of searching by the inventors of the present invention for microbes that produce an enzyme which forms a peptide from a carboxy component and an amine component at high yield.

Among the aforementioned strains of microbes, those microbes described with FERM numbers have been deposited at the independent administrative corporation, National Institute of Advanced Industrial Science and Technology, International Patent Organism Depository (Chuo Dai-6, 1-1 Higashi 1-Chome, Tsukuba-shi, Ibaraki-ken, Japan), and can be furnished by referring to each number.

Among the aforementioned strains of microbes, those microbes described with ATCC numbers have been deposited at the American Type Culture Collection (P.O. Box 1549, Manassas, Va. 20110, the United States of America), and can be furnished by referring to each number.

Among the aforementioned strains of microbes, those microbes described with IFO numbers have been deposited at the Institute of Fermentation, Osaka (2-17-85 Jusanbon-cho, Yodogawa-ku, Osaka-shi, Japan), and can be furnished by referring to each number.

Among the aforementioned strains of microbes, those microbes described with NBRC numbers have been deposited at the NITE Biological Resource Center of the National Institute of Technology and Evaluation (5-8 Kazusa-Kamaashi 2-Chome, Kisarazu-shi, Chiba-ken, Japan), and can be furnished by referring to each number.

Among the aforementioned strains of microbes, those microbes described with DSMZ numbers have been deposited at the Deutche Sammiung von Mikroorganismen und Zellkulturen GmbH (German Collection of Microbes and Cell Cultures) (Mascheroder Weg 1b, 38124 Braunschweig, Germany), and can be furnished by referring to each number.

*Empedobacter brevis* strain ATCC 14234 (strain FERM P-18545, strain FERM BP-8113) was deposited at the International Patent Organism Depository of the independent administrative corporation, National Institute of Advanced Industrial Science and Technology (Chuo Dai-6, 1-1 Higashi 1-Chome, Tsukuba-shi, Ibaraki-ken, Japan) on Oct. 1, 2001 and assigned the deposit number of FERM P-18545. Control of this organism was subsequently transferred to deposition under the provisions of the Budapest Treaty at the International Patent Organism Depository of the independent administrative corporation, National Institute of Advanced Industrial Science and Technology on Jul. 8, 2002 and was assigned the deposit number of FERM BP-8113 (indication of microbe: *Empedobacter brevis* strain AJ 13933).

*Sphingobacterium* sp. strain AJ 110003 was deposited at the International Patent Organism Depository of the independent administrative corporation, National Institute of Advanced Industrial Science and Technology on Jul. 22, 2002, and was assigned the deposit number of FERM BP-8124. Note that the strain AJ 110003 (FERM BP-8124) was identified to be the aforementioned *Sphingobacterium* sp. by the identification experiment described below. The strain FERM BP-8124 is a Gram-negative rod (0.7 to 0.8×1.5 to 2.0 μm) that forms spores and is not motile. Its colonies are round with a completely smooth border, contain low protrusions and have a glossy, light yellow color. The organism grows at 30° C. and is catalase positive, oxidase positive and negative for the OF test (glucose), and was identified as a bacterium belonging to the genus *Sphingobacterium* based on these properties. Moreover, because of the properties that it is negative for nitrate reduction, negative for indole production, negative for acid production from glucose, arginine dihydrolase negative, urease positive, esculin hydrolysis positive, gelatin hydrolysis negative, β-galactosidase positive, glucose assimilation positive, L-arabinose assimilation negative, D-mannose assimilation positive, D-mannitol assimilation negative, N-acetyl-D-glucosamine assimilation positive, maltose assimilation positive, potassium gluconate assimilation negative, n-capric acid assimilation negative, adipic acid assimilation negative, dl-malic acid assimilation negative, sodium citrate assimilation negative, phenyl acetate assimilation negative and cytochrome oxidase positive, it was determined to have properties that are similar to those of *Sphingobacterium multivorum* or *Sphingobacterium spiritivorum*. Moreover, although results of analyses on the homology of the base sequence of the 16S rRNA gene indicate the highest degree of homology with *Sphingobacterium multivorum* (98.8%), there was no strain with which the bacterial strain matched completely. Accordingly, this bacterial strain was therefore identified as *Sphingobacterium* sp.

(2) Microbe Culturing

In order to obtain microbial cells of microbes having the DNA of the present invention, the microbes can be cultured and grown in a suitable medium. There is no particular restriction on the medium used for this purpose so far as it allows the microbes to grow. This medium may be an ordinary medium containing ordinary carbon sources, nitrogen sources, phosphorus sources, sulfur sources, inorganic ions, and organic nutrient sources as necessary.

For example, any carbon source may be used so far as the microbes can utilize it. Specific examples of the carbon source that can be used include sugars such as glucose, fructose, maltose and amylose, alcohols such as sorbitol, ethanol and glycerol, organic acids such as fumaric acid, citric acid, acetic acid and propionic acid and their salts, hydrocarbons such as paraffin as well as mixtures thereof.

Examples of nitrogen sources that can be used include ammonium salts of inorganic acids such as ammonium sulfate and ammonium chloride, ammonium salts of organic acids such as ammonium fumarate and ammonium citrate, nitrates such as sodium nitrate and potassium nitrate, organic nitrogen compounds such as peptones, yeast extract, meat extract and corn steep liquor as well as mixtures thereof.

In addition, nutrient sources used in ordinary media, such as inorganic salts, trace metal salts and vitamins, can also be suitably mixed and used.

There is no particular restriction on culturing conditions, and culturing can be carried out, for example, for about 12 to about 48 hours while properly controlling the pH and temperature within a pH range of 5 to 8 and a temperature range of 15 to 40° C., respectively, under aerobic conditions.

(3) Purification of Enzyme

The DNA of the present invention encodes a peptide-forming enzyme. This peptide-forming enzyme can be purified from bacteria belonging to, for example, the genus *Empedobacter*. A method for isolating and purifying a peptide-forming enzyme from *Empedobacter brevis* is explained as an example of purification of the enzyme.

First, a microbial cell extract is prepared from the microbial cells of *Empedobacter brevis*, for example, the strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) by disrupting the cells using a physical method such as ultrasonic disruption or an enzymatic method using a cell wall-dissolving enzyme and removing the insoluble fraction by centrifugation and so forth. The peptide-forming enzyme can then be purified by fractionating the microbial cell extract solution obtained in the above manner by combining ordinary protein purification methods such as anion exchange chromatography, cation exchange chromatography or gel filtration chromatography.

An example of a carrier for use in anion exchange chromatography is Q-Sepharose HP (manufactured by Amersham). The enzyme is recovered in the non-adsorbed fraction under conditions of pH 8.5 when the cell extract containing the enzyme is allowed to pass through a column packed with the carrier.

An example of a carrier for use in cation exchange chromatography is MonoS HR (manufactured by Amersham). After adsorbing the enzyme onto the column by allowing the cell extract containing the enzyme to pass through a column packed with the carrier and then washing the column, the enzyme is eluted with a buffer solution having a high salt concentration. At that time, the salt concentration may be sequentially increased or a concentration gradient may be applied. For example, in the case of using MonoS HR, the enzyme adsorbed onto the column is eluted with NaCl of about 0.2 to about 0.5 M.

The enzyme purified in the manner described above can then be further uniformly purified by gel filtration chromatography and so forth. An example of the carrier for use in gel filtration chromatography is Sephadex 200 pg (manufactured by Amersham).

In the aforementioned purification procedure, the fraction containing the enzyme can be verified by assaying the peptide-forming activity of each fraction according to the method indicated in the examples to be described later. The internal amino acid sequence of the enzyme purified in the manner described above is shown in SEQ ID NO: 1 and SEQ ID NO: 2 of the Sequence Listing.

(4) DNA of the Present Invention and Transformants (4-1) DNA of the Present Invention A DNA of the present invention having the base sequence consisting of base numbers 61 to 1908 described in SEQ ID NO: 5 was isolated from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002). The DNA consisting of bases numbers 61-1908 described in SEQ ID NO: 5 is a code sequence (hereinafter, "CDS") portion. The base sequence consisting of bases numbers 61 to 1908 contains a signal sequence region and a mature protein region. The signal sequence region consists of bases numbers 61 to 126, while the mature protein region consists of bases numbers 127 to 1908. Namely, the present invention provides both a peptide enzyme protein gene that contains a signal sequence, and a peptide enzyme protein gene in the form of a mature protein. The signal sequence contained in the sequence described in SEQ ID NO: 5 is a type of leader sequence, and the main function of the leader peptide encoded by this leader sequence is presumed to be excretion from inside the cell membrane to outside the cell membrane. The protein encoded by bases numbers 127 to 1908, namely the site excluding the leader peptide, is a mature protein, and is presumed to exhibit a high degree of peptide-forming activity.

The DNA having a base sequence consisting of bases numbers 61 to 1917 described in SEQ ID NO: 11, which is also a DNA of the present invention, was isolated from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). The DNA having a base sequence consisting of bases numbers 61 to 1917 is a code sequence (CDS) portion. The base sequence consisting of bases numbers 61 to 1917 contains a signal sequence region and a mature protein region. The signal sequence region is a region that consists of bases numbers 61 to 120, while the mature protein region is a region that consists of bases numbers 121 to 1917. Namely, the present invention provides both a gene for a peptide enzyme protein gene that contains a signal sequence, and a gene for a peptide enzyme protein gene in the form of a mature protein. The signal sequence contained in the sequence described in SEQ ID NO: 11 is a kind of leader sequence. The main function of a leader peptide encoded by the leader sequence is presumed to be excretion from inside the cell membrane to outside the cell membrane. The protein encoded by bases numbers 121 to 1917, namely the portion excluding the leader peptide, is a mature protein, and it is presumed to exhibit a high degree of peptide-forming activity.

A DNA of the present invention having the base sequence consisting of bases numbers 61 to 1935 described in SEQ ID NO: 17 was isolated from *Pedobacter heparinus* strain IFO 12017 (Depositary institution: Institute of Fermentation, Osaka, Address of depositary institution: 2-17-85 Jusanbon-cho, Yodogawa-ku, Osaka-shi, Japan). The DNA consisting of bases numbers 61 to 1935 described in SEQ ID NO: 17 is a CDS portion. A signal sequence region and a mature protein region are contained in the base sequence consisting of bases numbers 61 to 1935. The signal sequence region consists of bases numbers 61 to 126, while the mature protein region consists of bases numbers 127 to 1935. Namely, the present invention provides both a peptide enzyme protein gene that contains a signal sequence, and a peptide enzyme protein gene in the form of a mature protein. The signal sequence contained in the sequence described in SEQ ID NO: 17 is a type of leader sequence, and the main function of the leader peptide encoded by this leader sequence region is presumed to be excretion from inside the cell membrane to outside the cell membrane. The protein encoded by bases numbers 127 to 1935, namely the site excluding the leader peptide, is a mature protein, and is presumed to exhibit a high degree of peptide-forming activity.

A DNA of the present invention having a base sequence consisting of bases numbers 61 to 1995 described in SEQ ID NO: 22 was isolated from *Taxeobacter gelupurpurascens* strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany). The DNA consisting of bases numbers 61 to 1995 described in SEQ ID NO: 22 is a CDS portion. A signal sequence region and a mature protein region are contained in the base sequence consisting of bases numbers 61 to 1995. The signal sequence region consists of bases numbers 61 to 126, while the mature protein region consists of bases numbers. 127 to 1995. Namely, the present invention provides both a peptide enzyme protein gene that contains a signal sequence, and a peptide enzyme protein gene in the form of a mature protein. The signal sequence contained in the sequence described in SEQ ID NO: 22 is a type of leader sequence, and the main function of the leader peptide encoded by this leader sequence region is presumed to be excretion from inside the cell membrane to outside the cell membrane. The protein encoded by bases numbers 127 to 1995, namely the site excluding the leader peptide, is a mature protein, and is presumed to exhibit a high degree of peptide-forming activity.

A DNA of the present invention having a base sequence consisting of bases numbers 29 to 1888 described in SEQ ID NO: 24 was isolated from *Cyclobacterium marinum* strain ATCC 25205 (Depositary institution: American Type Culture Collection, Address of depositary institution: P.O. Box 1549, Manassas, Va. 20110, the United States of America). The DNA consisting of bases numbers 29 to 1888 described in SEQ ID NO: 24 is a CDS portion. A signal sequence region and a mature protein region are contained in the base sequence consisting of bases numbers 29 to 1888. The signal sequence region consists of bases numbers 29 to 103, while the mature protein region consists of bases numbers 104 to 1888. Namely, the present invention provides both a peptide enzyme protein gene that contains a signal sequence, and a peptide enzyme protein gene in the form of a mature protein. The signal sequence contained in the sequence described in SEQ ID NO: 24 is a type of leader sequence, and the main function of the leader peptide encoded by this leader sequence region is presumed to be excretion from inside the cell membrane to outside the cell membrane. The protein encoded by bases numbers 104 to 1888, namely the site excluding the leader peptide, is a mature protein, and is presumed to exhibit a high degree of peptide-forming activity.

A DNA of the present invention having a base sequence consisting of bases numbers 61 to 1992 described in SEQ ID NO: 26 was isolated from *Psycloserpens burtonensis* strain ATCC 700359 (Depositary institution: American Type Culture Collection, Address of depositary institution: P.O. Box 1549, Manassas, Va. 20110, the United States of America). The DNA consisting of bases numbers 61 to 1992 described in SEQ ID NO: 26 is a CDS portion. A signal sequence region and a mature protein region are contained in the base sequence consisting of bases numbers 61 to 1992. The signal sequence region consists of bases numbers 61 to 111, while the mature protein region consists of bases numbers 112 to 1992. Namely, the present invention provides both a peptide enzyme protein gene that contains a signal sequence, and a peptide enzyme protein gene in the form of a mature protein. The signal sequence contained in the sequence described in SEQ ID NO: 26 is a type of leader sequence, and the main function of the leader peptide encoded by this leader sequence region is presumed to be excretion from inside the cell membrane to outside the cell membrane. The protein encoded by bases numbers 112 to 1992, namely the site excluding the leader peptide, is a mature protein, and is presumed to exhibit a high degree of peptide-forming activity.

Furthermore, the various gene recombination techniques described below can be carried out in compliance with the descriptions in publications such as Molecular Cloning, 2nd edition, Cold Spring Harbor Press (1989).

The DNA of the present invention can be obtained by polymerase chain reaction (hereinafter, "PCR") (refer to PCR; White T. J. et al., Trends Genet., 5, 185 (1989)) or hybridization from a chromosomal DNA or a DNA library of *Empedobacter brevis*, *Sphingobacterium* sp., *Pedobacter heparinus*, *Taxeobacter gelupurpurascens*, *Cyclobacterium marinum* or *Psycloserpens burtonensis*. Primers for PCR can be designed based on the internal amino acid sequences determined based on peptide-forming enzyme purified as explained in the aforementioned section (3). In addition, since the base sequences of peptide-forming enzyme gene (SEQ ID NO: 5, SEQ ID NO: 11, SEQ ID NO: 22, SEQ ID NO: 24 and SEQ ID NO: 26) have been clearly determined by the present invention, primers or probes for hybridization can be designed on the basis of these base sequences, and the gene can also be isolated using a probe. If primers having sequences corresponding to the 5'-non-translated region and 3'-non-translated region are used as PCR primers, the entire length of the coding region of the present enzyme can be amplified. For example, in amplifying the region containing both the leader sequence and mature protein coding region described in SEQ ID NO: 5, specifically, an example of the 5'-side primer is a primer having the base sequence of the region upstream of base number 61 in SEQ ID NO: 5, while an example of the 3'-side primer is a primer having a sequence complementary to the base sequence of the region downstream of base number 1908.

Primers can be synthesized by the phosphoamidite method (see Tetrahedron Letters (1981), 22, 1859) using, for example, the Model 380B DNA Synthesizer manufactured by Applied Biosystems in accordance with routine methods. The PCR reaction can be carried out, for example, in accordance with the method specified by the supplier such as the manufacturer using the Gene Amp PCR System 9600 (manufactured by Perkin-Elmer) and the Takara LA PCR In Vitro Cloning Kit (manufactured by Takara Shuzo).

Regardless of whether a leader sequence is contained or not, a DNA substantially identical to a DNA consisting of the CDS described in SEQ ID NO: 5 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 5 of the Sequence Listing, or with a probe prepared from the same base sequence, and encodes a protein having peptide-forming activity, from DNAs encoding the present enzyme having a mutation or cells possessing that DNA.

Regardless of whether a leader sequence is contained or not, a DNA substantially identical to a DNA consisting of the CDS described in SEQ ID NO: 11 of the Sequence Listing is also included in the DNA of the present invention. Namely, a DNA substantially identical to the DNA of the present invention can be obtained by isolating a DNA that hybridizes, under stringent conditions, with a DNA having a base sequence complementary to the CDS described in SEQ ID NO: 11 of the Sequence Listing, or with a probe prepared from the same base sequence, and encodes a protein that has peptide-forming activity, from DNAs encoding the present enzyme having a mutation or cells possessing the DNA.

Regardless of whether a leader sequence is contained or not, a DNA substantially identical to a DNA consisting of the CDS described in SEQ ID NO: 17 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 17 of the Sequence Listing, or with a probe prepared from the same base sequence, and encodes a protein having peptide-forming activity, from DNAs encoding the present enzyme having a mutation or cells possessing that DNA.

Regardless of whether a leader sequence is contained or not, a DNA substantially identical to a DNA consisting of the CDS described in SEQ ID NO: 22 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 22 of the Sequence Listing, or with a probe prepared from the same base sequence, and encodes a protein having peptide-forming activity, from DNAs encoding the present enzyme having a mutation or cells possessing that DNA.

Regardless of whether a leader sequence is contained or not, a DNA substantially identical to a DNA consisting of the CDS described in SEQ ID NO: 24 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 24 of the Sequence Listing, or with a probe prepared from the same base sequence, and encodes a protein having peptide-forming activity, from DNAs encoding the present enzyme having a mutation or cells possessing that DNA.

Regardless of whether a leader sequence is contained or not, a DNA substantially identical to a DNA consisting of the CDS described in SEQ ID NO: 26 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 26 of the Sequence Listing, or with a probe prepared from the same base sequence, and encodes a protein having peptide-forming activity, from DNAs encoding the present enzyme having a mutation or cells possessing that DNA.

A probe can be produced, for example, in accordance with established methods based on, for example, the base sequence described in SEQ ID NO: 5 of the Sequence Listing. In addition, a method for isolating a target DNA by using a probe to find a DNA that hybridizes with the probe may also be carried out in accordance with established methods. For example, a DNA probe can be produced by amplifying a base sequence cloned in a plasmid or phage vector, cleaving the base sequence desired to be used as a probe with a restriction enzyme and then extracting the desired base sequence. The portion to be cleaved out can be adjusted depending on the target DNA.

The term "under a stringent condition" as used herein refers to a condition under which a so-called specific hybrid is formed but no non-specific hybrid is formed. It is difficult to precisely express this condition in numerical values. For example, mention may be made of a condition under which DNAs having high homologies, for example, 50% or more, preferably 80% or more, more preferably 90% or more, hybridize with each other and DNAs having lower homologies than these do not hybridize with each other, or ordinary conditions for rinse in Southern hybridization under which hybridization is performed at 60° C. in a salt concentration corresponding to 60° C., 1×SSC and 0.1% SDS, preferably 0.1×SSC and 0.1% SDS. Although the genes that hybridize under such conditions include those genes in which stop codons have occurred at certain locations along their sequences or which have lost activity due to a mutation in the active center, these can be easily removed by ligating them to a commercially available expression vector, expressing them in a suitable host, and assaying the enzyme activity of the expression product using a method to be described later.

However, in the case of a base sequence that hybridizes under stringent conditions as described above, it is preferable that the protein encoded by that base sequence retains about a half or more, preferably 80% or more, and more preferably 90% or more, of the enzyme activity of the protein having the amino acid sequence encoded by the original base sequence serving as the base be retained under conditions of 50° C. and pH 8. For example, when explained for on the case of, for example, a base sequence that hybridizes under stringent conditions with a DNA that has a base sequence complementary to the base sequence consisting of bases numbers 127 to 1908 of the base sequence described in SEQ ID NO: 5, it is preferable that the protein encoded by that base sequence retains about a half or more, preferably 80% or more, and more preferably 90% or more, of the enzyme activity of the protein having an amino acid sequence that consists of amino acid residues numbers 23 to 616 of the amino acid sequence described in SEQ ID NO: 6 under conditions of 50° C. and pH 8.

An amino acid sequence encoded by the CDS described in SEQ ID NO: 5 of the Sequence Listing is shown in SEQ ID NO: 6 of the Sequence Listing. An amino acid sequence encoded by the CDS described in SEQ ID NO: 11 of the Sequence Listing is shown in SEQ ID NO: 12 of the Sequence Listing. An amino acid sequence encoded by the CDS described in SEQ ID NO.: 17 of the Sequence Listing is shown in SEQ ID NO: 18 of the Sequence Listing. An amino acid sequence encoded by the CDS described in SEQ ID NO: 22 of the Sequence Listing is shown in SEQ ID NO: 23 of the Sequence Listing. An amino acid sequence encoded by the CDS described in SEQ ID NO: 24 of the Sequence Listing is shown in SEQ ID NO: 25 of the Sequence Listing. An amino acid sequence encoded by the CDS described in SEQ ID NO: 26 of the Sequence Listing is shown in SEQ ID NO: 27 of the Sequence Listing.

The entire amino acid sequence described in SEQ ID NO: 6 contains a leader peptide and a mature protein region, with amino acid residues numbers 1 to 22 constituting the leader peptide, and amino acid residues numbers 23 to 616 constituting the mature protein region. In addition, the entire amino acid sequence described in SEQ ID NO: 11 includes a leader peptide and a mature protein region, with amino acid residues numbers 1 to 20 constituting the leader peptide, and amino acid residues numbers 21 to 619 constituting the mature protein region.

The entire amino acid sequence described in SEQ ID NO: 18 contains a leader peptide and a mature protein region, with amino acid residues numbers 1 to 22 constituting the leader peptide, and amino acid residues numbers 23 to 625 constituting the mature protein region.

The entire amino acid sequence described in SEQ ID NO: 23 contains a leader peptide and a mature protein region, with amino acid residues numbers 1 to 22 constituting the leader peptide, and amino acid residues numbers 23 to 645 constituting the mature protein region.

The entire amino acid sequence described in SEQ ID NO: 25 contains a leader peptide and a mature protein region, with amino acid residues numbers 1 to 25 constituting the leader peptide, and amino acid residues numbers 26 to 620 constituting the mature protein region.

The entire amino acid sequence described in SEQ ID NO: 27 contains a leader peptide and a mature protein region, with amino acid residues numbers 1 to 17 constituting the leader peptide, and amino acid residues numbers 18 to 644 constituting the mature protein region.

The protein encoded by the DNA of the present invention is a protein in which the mature protein has peptide-forming activity, and a DNA that encodes a protein substantially identical to a protein having the amino acid sequence described in SEQ ID NO: 6, SEQ ID NO: 12, SEQ ID NO: 18, SEQ ID NO: 23, SEQ ID NO: 25, or SEQ ID NO: 27 of the Sequence Listing, regardless of whether it contains a leader peptide or not, is also included in the DNA of the present invention. (Note that, base sequences are specified from amino acid sequences in accordance with the codes of the universal codons.) Namely, the present invention provides DNAs that encode proteins indicated in (A) to (X) below:

(A) a protein having an amino acid sequence consisting of amino acid residues numbers 23 to 616 of an amino acid sequence described in SEQ ID NO: 6 of the Sequence Listing, (B) a protein having an amino acid sequence including substitution, deletion, insertion, addition, and/or inversion of one or a plurality of amino acids in amino acid residues numbers 23 to 616 of the amino acid sequence described in SEQ ID NO: 6 of the Sequence Listing, and having peptide-forming activity, (C) a protein having the amino acid sequence consisting of amino acid residue numbers 21 to 619 of an amino acid sequence described in SEQ ID NO: 12 of the Sequence Listing, (D) a protein having an amino acid sequence including substitution, deletion, insertion, addition, and/or inversion of one or a plurality of amino acids in amino acid residue numbers 21 to 619 of the amino acid sequence described in SEQ ID NO: 12 of the Sequence Listing, and having peptide-forming activity, (E) a protein having an amino acid sequence consisting of amino acid residues numbers 23 to 625 of an amino acid sequence described in SEQ ID NO: 18 of the Sequence Listing, (F) a protein having an amino acid sequence including substitution, deletion, insertion, addition, and/or inversion of one or a plurality of amino acids in amino acid residues numbers 23 to 625 of the amino acid sequence described in SEQ ID NO: 18 of the Sequence Listing, and having peptide-forming activity, (G) a protein having an amino acid sequence consisting of amino acid residues numbers 23 to 645 of an amino acid sequence described in SEQ ID NO: 23 of the Sequence Listing, (H) a protein having an amino acid sequence including substitution, deletion, insertion, addition, and/or inversion of one or a plurality of amino acids in amino acid residues numbers 23 to 645 of the amino acid sequence described in SEQ ID NO: 23 of the Sequence Listing, and having peptide-forming activity, (I) a protein having an amino acid sequence consisting of amino acid residues numbers 26 to 620 of an amino acid sequence described in SEQ ID NO: 25 of the Sequence Listing, (J) a protein having an amino acid sequence including substitution, deletion, insertion, addition, and/or inversion of one or a plurality of amino acids in amino acid residues numbers 26 to 620 of the amino acid sequence described in SEQ ID NO: 25 of the Sequence Listing, and having peptide-forming activity, (K) a protein having an amino acid sequence consisting of amino acid residues numbers 18 to 644 of an amino acid sequence described in SEQ ID NO: 27 of the Sequence Listing, (L) a protein having an amino acid sequence including substitution, deletion, insertion, addition, and/or inversion of one or a plurality of amino acids in amino acid residues numbers 18 to 644 of the amino acid sequence described in SEQ ID NO: 27 of the Sequence Listing, and having peptide-forming activity, (M) a protein having an amino acid sequence described in SEQ ID NO: 6 of the Sequence Listing, (N) a protein containing a mature protein region, having an amino acid sequence including substitution, deletion, insertion, addition, and/or inversion of one or a plurality of amino acids in the amino acid sequence described in SEQ ID NO: 6 of the Sequence Listing, and having peptide-forming activity, (O) a protein having the amino acid sequence described in SEQ ID NO: 12 of the Sequence Listing, (P) a protein containing a mature protein region, having an amino acid sequence including substitution, deletion, insertion, addition, and/or inversion of one or a plurality of amino acids in an amino acid sequence described in SEQ ID NO: 12 of the Sequence Listing, and having peptide-forming activity, (Q) a protein having an amino acid sequence described in SEQ ID NO: 18 of the Sequence Listing, (R) a protein containing a mature protein region, having an amino acid sequence including substitution, deletion, insertion, addition, and/or inversion of one or a plurality of amino acids in the amino acid sequence described in SEQ ID NO: 18 of the Sequence Listing, and having peptide-forming activity, (S) a protein having an amino acid sequence described in SEQ ID NO: 23 of the Sequence Listing, (T) a protein containing a mature protein region, having an amino acid sequence including substitution, deletion, insertion, addition, and/or inversion of one or a plurality of amino acids in the amino acid sequence described in SEQ ID NO: 23 of the Sequence Listing, and having peptide-forming activity, (U) a protein having an amino acid sequence described in SEQ ID NO: 25 of the Sequence Listing, (V) a protein containing a mature protein region, having an amino acid sequence including substitution, deletion, insertion, addition, and/or inversion of one or a plurality of amino acids in the amino acid sequence described in SEQ ID NO: 25 of the Sequence Listing, and having peptide-forming activity;

(W) a protein having an amino acid sequence described in SEQ ID NO: 27 of the Sequence Listing, and (X) a protein containing a mature protein region, having an amino acid sequence in the amino acid sequence described in SEQ ID NO: 27 of the Sequence Listing, and having peptide-forming activity.

Here, although the meaning of the term "a plurality of" varies depending on the locations and types of the amino acid residues in the three-dimensional structure of the protein, it is within a range that does not significantly impair the three-dimensional structure and activity of the protein of the amino acid residues, and is specifically 2 to 50, preferably 2 to 30, and more preferably 2 to 10. However, in the case of amino acid sequences including substitution, deletion, insertion, addition, and/or inversion of one or a plurality of amino acids in amino acid sequences of the proteins of (B), (D), (F), (H), (J), (L), (N), (P), (R), (T), (V) or (X), it is preferable that the proteins retain about half or more, more preferably 80% or more, and even more preferably 90% or more of the enzyme activity of the proteins in the state where no mutation is included, under conditions of 50° C. and pH 8. For example, explanation will be made in the case of (B); in the case of the amino acid sequence (B) including substitution, deletion, insertion, addition, and/or inversion of one or a plurality of amino acids in the amino acid sequence described in SEQ ID NO: 6 of the Sequence Listing, it is preferable that this protein retains about half or more, more preferably 80% or more, and even more preferably 90% or more of the enzyme activity of the protein having the amino acid sequence described in SEQ ID NO: 6 of the Sequence Listing, under conditions of 50° C. and pH 8.

A mutation of an amino acid like that indicated in the aforementioned (B) and so forth is obtained by modifying the base sequence so that an amino acid of a specific site in the present enzyme gene is substituted, deleted, inserted or added by, for example, site-directed mutagenesis. In addition, a modified DNA that described above can also be obtained by mutagenesis treatment known in the art. Mutagenesis treatment refers to, for example, a method in which a DNA encoding the present enzyme is treated in vitro with hydroxylamine and so forth, as well as a method in which bacteria belonging to the genus *Escherichia* that possess a DNA encoding the present enzyme are treated by a mutagen normally used in artificial mutagenesis, such as ultraviolet irradiation, N-methyl-N'-nitro-N-nitrosoguanidine (NTG) or nitrous acid.

In addition, naturally-occurring mutations such as differences attributable to a microbe species or strain are also included in the base substitution, deletion, insertion, addition and/or inversion described above. By expressing a DNA having such a mutation in suitable cells and investigating the enzyme activity of the expression product, a DNA can be obtained that encodes a protein substantially identical to the protein described in SEQ ID NO: 6 or 12 of the Sequence Listing.

(4-2) Preparation of Transformants and Production of Peptide-Forming Enzymes

Peptide-forming enzymes can be produced by introducing a DNA of the present invention into a suitable host and expressing the DNA in that host.

Examples of hosts for expressing a protein specified by a DNA of the present invention that can be used include various prokaryotic cells such as bacteria belonging to the genus *Escherichia* such as *Escherichia coli*, *Empedobacter*, *Sphingobacterium*, *Flavobacterium* and *Bacillus* such as *Bacillus subtilis*, as well as various eukaryotic cells such as *Saccharomyces cerevisiae*, *Pichia stipitis* and *Aspergillus oryzae*.

A recombinant DNA used to introduce a DNA into a host can be prepared by inserting the DNA to be introduced into a vector corresponding to the type of host in which the DNA is to be expressed, in such a form that the protein encoded by that DNA can be expressed. In the case where a promoter unique to a peptide-forming enzyme gene of *Empedobacter brevis* and so forth functions in the host cells, the promoter can be used as a promoter for expressing the DNA of the present invention. In addition, another promoter that acts on in the host cells may be ligated to the DNA of the present invention and the DNA may be expressed under the control of the promoter as necessary.

Examples of transformation methods for introducing a recombinant DNA into host cells include the method of D. M. Morrison (see Methods in Enzymology, 68, 326 (1979)) or the method in which DNA permeability is increased by treating receptor microbial cells with calcium chloride (see Mandel, H. and Higa, A., J. Mol. Biol., 53, 159 (1970)).

In the case of mass production of a protein using recombinant DNA technology, conjugating the protein within a transformant that produces the protein to form an inclusion body of protein is also a preferable mode for carrying out the present invention. Advantages of this expression and production method include protection of the target protein from digestion by proteases present in the microbial cells, and simple and easy purification of the target protein by disrupting the microbial cells, followed by centrifugation and so forth.

The inclusion bodies of protein obtained in this manner are solubilized with a protein denaturant and the solubilized protein is converted to a properly folded, physiologically active protein by going through an activity regeneration procedure that consists primarily of lysing the protein with a protein denaturant followed by removal of the denaturant. There are numerous examples of this, including regeneration of the activity of human interleukin-2 (see Japanese Patent Application Laid-open Publication No. S61-257931).

To obtain an active protein from inclusion bodies of protein, a series of operations including solubilization and activity regeneration are required, and the procedure is more complex than in the case of producing the active protein directly. However, in the case of producing a large volume of protein that has a detrimental effect on microbial growth in microbial cells, that effect can be suppressed by accumulating the proteins in the form of inclusion bodies of inactive protein in the microbial cells.

Examples of mass production methods for producing a large volume of target protein in the form of inclusion bodies include a method in which a target protein is expressed independently under the control of a powerful promoter, and a method in which a target protein is expressed in the form of a fused protein with a protein that is known to be expressed in a large volume.

Hereinafter, the present invention will be explained more specifically taking as an example of a method for producing transformed *Escherichia coli* and using the transformed microbe to produce a peptide-forming enzyme. Furthermore, in the case of producing a peptide-forming enzyme in a microbe such as *Escherichia coli*, a DNA may be incorporated that encodes a precursor protein containing a leader sequence or a DNA may be incorporated that consists only of a mature protein region that does not contain a leader sequence, and the DNA can be suitably selected for the protein encoding sequence depending on the production conditions, form, usage conditions and so forth of the enzyme to be produced.

Promoters normally used in the production of heterogeneous proteins in *Escherichia coli* can be used as promoters for expressing a DNA encoding a peptide-forming enzyme. Examples of such promoters include T7 promoter, lac promoter, trp promoter, trc promoter, tac promoter, lambda phage PR promoter, PL promoter and other powerful promoters. In addition, examples of vectors that can be used include pUC19, pUC18, pBR322, pHSG299, pHSG298, pHSG399, pHSG398, RSF1010, pMW119, pMW118, pMW219, and pMW218. Besides, vectors of phage DNA can also be used. Moreover, expression vectors can be used that contain promoters and are capable of expressing an inserted DNA sequence, including the promoter can be used.

In order to produce a peptide-forming enzyme in the form of an inclusion body of fused protein, a gene that encodes another protein, and preferably a hydrophilic peptide is ligated upstream or downstream of the peptide-forming enzyme gene to obtain a fused protein gene. The gene that encodes another protein in this manner may be any gene that increases the amount of the fused protein accumulated, and enhances the solubility of the fused protein after the denaturation and regeneration steps. Examples of candidates for such genes include T7 gene 10, β-galactosidase gene, dehydrofolate reductase gene, γ-interferon gene, interleukin-2 gene and prochymosin gene.

When these genes are ligated to a gene that encodes a peptide-forming enzymes, the both genes are ligated so that their reading frames of codons are consistent. The genes may be ligated at a proper restriction enzyme site or a synthetic DNA having a proper sequence may be utilized.

Further, to increase a production amount of the peptide-forming enzyme, it is preferable in some cases that a terminator, which is a transcription terminating sequence, be ligated to downstream of the fusion protein gene. The terminator includes, for example, a T7 terminator, an fd phage terminator, a T4 terminator, a tetracycline resistant gene terminator, and an *Escherichia coli* trpA gene terminator.

As the vectors for introducing a gene that encodes a peptide-forming enzyme or a fused protein between the peptide-forming enzyme and another protein in *Escherichia coli* are preferred so-called multi-copy type vectors, examples of which include a plasmid having a replication origin derived from ColE1, for example, a pUC-based plasmid, and a pBR322-based plasmid or derivatives thereof. The "derivatives" as used herein refer to those plasmids that are subjected to modification by substitution, deletion, insertion, addition and/or inversion of bases. Note that the modification as used herein includes modifications by a mutagenesis treatment with a mutagen or UV irradiation, or modifications by spontaneous mutation.

To screen transformants, it is preferable that the vectors have markers such as an ampicillin resistant gene. Such plasmids include commercially available expression vectors having potent promoters (a pUC-based vector (manufactured by Takara Shuzo, Co., Ltd.), pRROK-based vector (manufactured by Clonetech Laboratories, Inc.), pKK233-2 (manufactured by Clonetech Laboratories, Inc.) and so forth.

A recombinant DNA is obtained by ligating a DNA fragment to a vector DNA; in the DNA fragment, a promoter, a gene encoding L-amino acid amide hydrolase or a fused protein consisting of an L-amino acid amide hydrolase and another protein, and depending on the case, a terminator are ligated in that order.

When *E. coli* is transformed using the recombinant DNA and the resulting *E. coli* is cultured, a peptide-forming enzyme or a fused protein consisting of the peptide-forming enzyme and another protein is expressed and produced. Although a strain that is normally used in the expression of a heterogeneous gene can be used as a host to be transformed, *Escherichia coli* strain JM109, for example, is preferable. Methods for carrying out transformation and methods for screening out transformants are described in Molecular Cloning, 2nd Edition, Cold Spring Harbor Press (1989) and other publications.

In the case of expressing a peptide-forming enzyme in the form of a fusion protein, the peptide-forming enzyme may be cleaved out using a restriction protease that uses a sequence not present in the peptide-forming enzyme, such as blood coagulation factor Xa or kallikrein, as the recognition sequence.

A medium normally used for culturing *E. coli*, such as M9-casamino acid medium or LB medium, may be used for as the a production medium. In addition, culturing conditions and production induction conditions are suitably selected according to the marker of the vector used, promoter, type of host microbe and so forth.

The following method can be used to recover the peptide-forming enzyme or fused protein consisting of the peptide-forming enzyme and another protein. If the peptide-forming enzyme or its fused protein has been solubilized in the microbial cells, the microbial cells are recovered and then disrupted or lysed so that they can be used as a crude enzyme liquid. Moreover, the peptide-forming enzyme or its fused protein can be purified prior to use by ordinary techniques such as precipitation, filtration or column chromatography as necessary. In this case, a purification method can also be used that uses an antibody of the peptide-forming enzyme or its fused protein.

In the case where inclusion bodies of protein are formed, the inclusion bodies are solubilized with a denaturant. Although they may be solubilized together with the microbial cell protein, it is preferable in consideration of the subsequent purification procedure that the inclusion bodies are taken out and then solubilized. Conventionally known methods may be used to recover the inclusion bodies from the microbial cells. For example, the inclusion bodies can be recovered by disrupting the microbial cells followed by centrifugation. Examples of denaturants capable of solubilizing the inclusion bodies include guanidine hydrochloride (for example, 6 M, pH 5 to 8) and urea (for example, 8 M) and the like.

A protein that has activity is regenerated by removing these denaturants by dialysis or the like. A Tris-HCl buffer solution, a phosphate buffer solution or the like may be used as a dialysis solution to be used in dialysis, and its concentration may be, for example, 20 mM to 0.5 M, while its pH may be, for example, 5 to 8.

The protein concentration during the regeneration step is preferably held to about 500 µg/ml or less. The dialysis temperature is preferably 5° C. or lower to prevent the regenerated peptide-forming enzyme from undergoing self-crosslinking. Moreover, the method for removing the denaturants includes dilution or ultrafiltration in addition to dialysis, and it is expected the activity can be regenerated whichever denaturant is used.

(5) Properties of Enzyme Encoded by DNA of the Present Invention

The activity of the enzyme encoded by the DNA of the present invention can be assayed by, for example, allowing the enzyme to react in a borate buffer solution containing an amino acid ester and an amine as substrates, and then quantifying the peptide formed. In a more concrete example, the reaction is carried out at 25° C. for several minutes using a borate buffer solution (pH 9.0) containing 100 mM L-alanine methyl ester and 200 mM L-glutamine.

The activity unit of the enzyme used in the present invention is defined such that 1 unit (U) is the amount of enzyme that produces 1 micromole (μmole) of peptide in 1 minute under the condition of reacting at 25° C. using a 100 mM borate buffer solution (pH 9.0) containing 100 mM L-alanine methyl ester and 200 mM L-glutamine.

A protein encoded by the DNA of the present invention is a peptide-forming enzyme protein. Peptide-forming activity refers to the activity that forms a peptide from a carboxy component and an amine component. Hereinafter, a preferable mode of the enzyme encoded by the DNA of the present invention will be explained on its properties.

One preferable mode of the enzyme encoded by the DNA of the present invention includes an enzyme that has the abilities described below, for which the dipeptide production rate is used as an indicator. Namely, one preferable mode of the enzyme of the present invention includes an enzyme that has the ability to form a peptide from a carboxy component and an amino component, and has a production rate of L-alanyl-L-glutamine in the dipeptide formation reaction under the conditions of (i) to (iv) below of preferably 0.03 mM/min or more, more preferably 0.3 mM/min or more, and particularly preferably 1.0 mM/min or more. The conditions of the dipeptide formation reaction are as follows:

(i) the carboxy component is L-alanine methyl ester hydrochloride (100 mM);
(ii) the amine component is L-glutamine (200 mM);
(iii) the pH is 9.0; and,
(iv) the amount of homogenously purified enzyme added is less than 0.61 mg/ml as a protein amount.

The aforementioned production rate far exceeds the conventional production rate for peptide synthesis using an enzyme, and the enzyme of the present invention has the ability to catalyze peptide synthesis at an extremely rapid rate.

The aforementioned amount of enzyme added indicates a final amount of the enzyme that is added to the reaction system, and addition of the enzyme of 0.01 mg/ml or more, and preferably 0.02 mg/ml or more, as protein amount is desirable. The term "protein amount" refers to the value indicated by a calorimetric method with Coomassie brilliant blue using a protein assay CBB solution (manufactured by Nakarai) and bovine serum albumin as a standard substance.

In a specific example of the procedure for assaying the enzyme activity, the enzyme activity can be assayed by allowing the enzyme to react in a borate buffer solution containing an amino acid ester and an amine as substrates and quantifying the resulting peptide. In a more specific example, mention may be made of a method in which the enzyme is allowed to react for several minutes at 25° C. using a 100 mM borate buffer solution (pH 9.0) containing 100 mM L-alanine methyl ester and 200 mM L-glutamine.

In addition, a preferable mode of the enzyme encoded by the DNA of the present invention includes an enzyme having the property by which both an amino acid ester and an amino acid amide can be used as a substrate for the carboxy component. The words "both an amino acid ester and an amino acid amide can be used as a substrate" mean that at least one type or more of amino acid ester and at least one type or more of amino acid amide can be used as a substrate. In addition, one preferable mode of the enzyme of the present invention includes an enzyme that has the property by which all of an amino acid, a C-protected amino acid and an amine can be used as a substrate for the amine component. The words "an amino acid, a C-protected amino acid, and an amine can be used as a substrate" mean that at least one type or more of amino acid, at least one type or more of C-protected amino acid, and at least one type or more of amine can be used as a substrate. Having a wide range of substrate specificity with respect to the carboxy component or the amino component, the enzyme of the present invention is preferable in that a wide range of raw materials can be selected, which in turn is favorable in terms of cost and production equipment in the case of industrial production.

Specific examples of the carboxy component include L-amino acid esters, D-amino acid esters, L-amino acid amides and D-amino acid amides. In addition, the amino acid esters include not only amino acid esters corresponding to naturally-occurring amino acids, but also amino acid esters corresponding to non-naturally-occurring amino acids or their derivatives. Furthermore, examples of the amino acid esters include α-amino acid esters as well as β-, γ-, and ω-amino acid esters and the like, which have different amino group bonding sites. Typical examples of amino acid esters include methyl esters, ethyl esters, n-propyl esters, iso-propyl esters, n-butyl esters, iso-butyl esters, and tert-butyl esters of amino acids.

Specific examples of the amine component include L-amino acids, C-protected L-amino acids, D-amino acids, C-protected D-amino acids and amines. In addition, examples of the amines include not only naturally-occurring amines, but also non-naturally-occurring amines or their derivatives. In addition, examples of the amino acids include not only naturally-occurring amino acids, but also non-naturally-occurring amino acids or their derivatives. These include α-amino acids as well as β-, γ- and ω-amino acids and the like, which have different amino group bonding sites.

Further, in another aspect, one preferable mode of the enzyme encoded by the DNA of the present invention includes an enzyme in which the pH range over which the peptide-forming reaction can be catalyzed is 6.5 to 10.5. The ability of the enzyme of the present invention to catalyze this reaction over such a wide pH range as stated above is preferable in that it allows flexible accommodation of industrial production that could be subject to the occurrence of various restrictions. However, in the actual production of peptides, it is preferable to use the enzyme by further adjusting to an optimum pH corresponding to the obtained enzyme so as to maximize the catalytic performance of the enzyme.

Moreover, in another aspect, one preferable mode of the enzyme encoded by the DNA of the present invention includes an enzyme for which the temperature range over which the enzyme is capable of catalyzing the peptide-forming reaction is within the range of 0 to 60° C. Since the enzyme of the present invention is able to catalyze the reaction over a wide temperature range, it is preferable in that it allows flexible accommodation of industrial production that could be subject to the occurrence of various restrictions. However, in the actual production of peptides, it is preferable to use the enzyme by further adjusting to an optimum temperature corresponding to the obtained enzyme so as to maximize the catalytic performance of the enzyme.

(6) Dipeptide Production Method

The method for producing dipeptide of the present invention includes reaction between a carboxy component and an amine component in the presence of the predetermined enzyme. The dipeptide production method of the present invention includes allowing an enzyme, or enzyme-containing substance, having the ability to form a peptide from a carboxy component and an amine component, to act on the carboxy component and the amine component to synthesize a dipeptide.

The method of allowing the enzyme or enzyme-containing substance used in the present invention to act on the carboxy component and the amine component may be mixing the enzyme or enzyme-containing substance, the carboxy component, and the amine component with each other. More specifically, a method of adding the enzyme or enzyme-containing substance to a solution containing a carboxy component and an amine component and allowing them to react may be used. Alternatively, in the case of using a microbe that produces that enzyme, a method may be used that includes culturing the microbe that forms that enzyme, producing and accumulating the enzyme in the microbe or microbial culture broth, and then adding the carboxy component and amine component to the culture broth. The produced dipeptide can then be collected by established methods and purified as necessary.

The term "enzyme-containing substance" means any substance so far as it contains the enzyme, and examples of specific forms thereof include a culture of microbes that produce the enzyme, microbial cells isolated from the culture, and a product obtained by treating the microbial cells (hereinafter, "treated microbial cell product"). A culture of microbes refers to what is obtained by culturing a microbe, and more specifically, to a mixture of microbial cells, the medium used for culturing the microbe, and substances produced by the cultured microbe, and so forth. In addition, the microbial cells may be washed and used in the form of washed microbial cells. In addition, the treated microbial cell product includes the products of disrupted, lysed or freeze-dried microbial cells, and the like, and also includes a crude enzyme recovered by treating microbial cells, and so forth, as well as a purified enzyme obtained by purification of the crude enzyme, and so forth. A partially purified enzyme obtained by various types of purification methods may be used for the purified enzyme, or immobilized enzymes may be used that have been immobilized by a covalent bonding method, an adsorption method, an entrapment method, or the like. In addition, since some microbes are partially lysed during culturing depending on the microbes used, the culture supernatant may also be used as the enzyme-containing substance in such cases.

In addition, wild strains may be used as the microbes that contain the enzyme, or gene recombinant strains that express the enzyme may also be used. The microbes are not limited to intact microbial cells, but rather acetone-treated microbial cells, freeze-dried microbial cells or other treated microbial cells may also be used. Immobilized microbial cells and an immobilized treated microbial cell product obtained by immobilizing the microbial cells or treated microbial cell product by covalent bonding, adsorption, entrapment or other methods, as well as treated immobilized microbial cells, may also be used.

Furthermore, when using cultures, cultured microbial cells, washed microbial cells or a treated microbial cell product that has been obtained by disrupted or lysing microbial cells, it is often the case that an enzyme exists therein that decomposes the formed peptides without being involved in peptide formation. In this situation, it may be rather preferable in some cases to add a metal protease inhibitor like ethylene diamine tetraacetic acid (EDTA). The addition amount is within the range of 0.1 millimolar (mM) to 300 mM, and preferably 1 mM to 100 mM.

A preferable mode of the dipeptide production method of the present invention is a method in which the transformed cells described in the previously described section (4-2) are cultured in a medium, and a peptide-forming enzyme is allowed to accumulate in the medium and/or transformed cells. Since the peptide-forming enzyme can be easily produced in large volumes by using a transformant, dipeptides can be produced in large amounts and rapidly.

The amount of enzyme or enzyme-containing substance used may be enough if it is an amount at which the target effect is demonstrated (effective amount), and this effective amount can be easily determined through simple, preliminary experimentation by a person with ordinary skill in the art. In the case of using the enzyme, for example, the amount used is about 0.01 U to about 100 U, while in the case of using washed microbial cells, the amount used is about 1 g/L to about 500 g/L.

Any carboxy component may be used as far as it can form a peptide by condensation with the other substrate in the form of the amine component. Examples of carboxy component include L-amino acid esters, D-amino acid esters, L-amino acid amides and D-amino acid amides as well as organic acid esters not having an amino group. In addition, examples of amino acid esters include not only amino acid esters corresponding to naturally-occurring amino acids, but also amino acid esters corresponding to non-naturally-occurring amino acids or their derivatives. In addition, examples of amino acid esters include α-amino acid esters as well as β-, γ- and ω-amino acid esters and the like having different amino group bonding sites. Typical examples of amino acid esters include methyl esters, ethyl esters, n-propyl esters, iso-propyl esters, n-butyl esters, iso-butyl esters and tert-butyl esters of amino acids.

Any amine component may be used as far as it can form a peptide by condensation with the other substrate in the form of the carboxy component. Examples of the amine component include L-amino acids, C-protected L-amino acids, D-amino acids, C-protected D-amino acids and amines. In addition, examples of the amines include not only naturally-occurring amines, but also non-naturally-occurring amines or their derivatives. In addition, examples of the amino acids include not only naturally-occurring amino acids, but also non-naturally-occurring amino acids or their derivatives. These include α-amino acids as well as β-, γ- or ω-amino acids and the like having different amino group bonding sites.

The concentrations of the carboxy component and amine component serving as starting materials are 1 mM to 10 M, and preferably 0.05 M to 2 M, respectively; however, there are cases where it is preferable to add amine component in an amount equimolar or excess molar with respect to the carboxy component. In addition, in cases where high concentrations of substrates inhibit the reaction, these can be added stepwise during the reaction after they are adjusted to concentrations that do not cause inhibition.

The reaction temperature that allows synthesis of peptide is 0 to 60° C., and preferably 5 to 40° C. In addition, the reaction pH that allows synthesis of peptide is 6.5 to 10.5, and preferably 7.0 to 10.0.

EXAMPLES

Hereinafter, the present invention will be explained by examples. However, the present invention is not limited to these examples. In addition to confirmation by ninhydrin coloring of thin-film chromatograms (qualitative), quantitative determinations were made by the following high-performance liquid chromatography in order to assay products.

Column: InertsiL ODS-2 (manufactured by GL Science, Inc.), eluate: an aqueous phosphate solution containing 5.0 mM sodium 1-octanesulfonate (pH 2.1):methanol=100:15 to 50, flow rate: 1.0 mL/min, detection: 210 nanometers (hereinafter, "nm").

Example 1

Microbe Culturing (*Empedobacter brevis* Strain FERM BP-8113)

A 50 mL medium (pH 6.2) containing 5 grams (g) of glucose, 5 g of ammonium sulfate, 1 g of monopotassium phosphate, 3 g of dipotassium phosphate, 0.5 g of magnesium sulfate, 10 g of yeast extract and 10 g of peptone in 1 liter (L) was transferred to a 500 mL Sakaguchi flask and sterilized at 115° C. for 15 minutes. This medium was then inoculated with one loopful cells of *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) that had been cultured at 30° C. for 16 hours in the same medium, followed by shake culturing at 30° C. for 16 hours and 120 strokes/min.

Example 2

Production of Peptide Using Microbial Cells

Microbial cells were collected by centrifuging (10,000 rounds per minute (rpm), 15 minutes) the culture broth obtained in Example 1, followed by suspending them to a concentration of 100 g/L in 100 mM borate buffer (pH 9.0) containing 10 mM EDTA. After respectively adding 1 mL of the suspension to 1 mL each of 100 mM borate buffer solutions (pH 9.0) containing 10 mM EDTA, 200 mM of the following carboxy components, and 400 mM of the following amino acids to make a final volume of 2 mL, the reaction was carried out at 18° C. for 2 hours. The peptides that were formed as a result of this reaction are shown in Table 1.

TABLE 1

| Carboxy component | Amine component | Formed peptide | (mM) |
| --- | --- | --- | --- |
| L-Ala-OMe | L-Leu | L-Ala-L-Leu | 38.2 |
|  | L-Met | L-Ala-L-Met | 68.3 |
|  | L-Phe | L-Ala-L-Phe | 62.4 |
|  | L-Ser | L-Ala-L-Ser | 51.3 |
|  | L-His | L-Ala-L-His | 52.1 |
|  | L-Arg | L-Ala-L-Arg | 72.1 |
|  | L-Gln | L-Ala-L-Gln | 68.0 |
| Gly-OMe | L-His | L-Gly-L-His | 22.1 |
| L-Ser-OMe | L-Ser | L-Ser-L-Ser | 29.0 |
| L-Val-OMe | L-Met | L-Val-L-Met | 10.5 |
| L-Met-OMe | L-Phe | L-Met-L-Phe | 28.5 |
| L-Thr-OMe | L-Leu | L-Thr-L-Leu | 23.0 |
| L-Ile-OMe | L-Met | L-Ile-L-Met | 8.3 |

Hydrochloride salts were used for all the carboxy components.

Example 3

Purification of Enzyme

The procedure after centrifugation was carried out either on ice or at 4° C. *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was cultured in the same manner in as Example 1, and the microbial cells were collected by centrifugation (10,000 rpm, 15 minutes). After washing 16 g of microbial cells with 50 mM Tris-HCl buffer (pH 8.0), they were suspended in 40 milliliters (ml or mL) of the same buffer and subjected to ultrasonic disrupting treatment for 45 minutes at 195 watts. This ultrasonically disrupted liquid was then centrifuged (10,000 rpm, 30 minutes) to remove the cell debris and obtain an ultrasonically disrupted liquid supernatant. This ultrasonically disrupted liquid supernatant was dialyzed overnight against 50 mM Tris-HCl buffer (pH 8.0) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 8.0), and the active fraction was collected from the non-adsorbed fraction. This active fraction was dialyzed overnight against 50 mM acetate buffer (pH 4.5) followed by removal of the insoluble fraction by centrifugation (10,000 rpm, 30 minutes) to obtain a dialyzed fraction in the form of the supernatant liquid. This dialyzed fraction was then applied to a Mono S column (manufactured by Amersham) pre-equilibrated with 50 mM acetate buffer (pH 4.5) to elute enzyme at a linear concentration gradient of the same buffer containing 0 to 1 M NaCl. The fraction that had the lowest level of contaminating protein among the active fractions was applied to a Superdex 200 pg column (manufactured by Amersham) pre-equilibrated with 50 mM acetate buffer (pH 4.5) containing 1 M NaCl, and gel filtration was performed by allowing the same buffer (pH 4.5) containing 1 M NaCl to flow through the column to obtain an active fraction solution. As a result of performing these operations, the peptide-forming enzyme used in the present invention was confirmed to have been uniformly purified based on the experimental results of electrophoresis. The enzyme recovery rate in the aforementioned purification process was 12.2% and the degree of purification was 707 folds.

Example 4

Measurement of Molecular Weight of Enzyme

SDS-Gel Electrophoresis

A 0.3 microgram (μg) equivalent of the purified enzyme fraction obtained by the method of Example 3 was applied to polyacrylamide electrophoresis. 0.3% (w/v) Tris, 1.44% (w/v) glycine and 0.1% (w/v) sodium laurylsulfate were used for the electrophoresis buffer solution, a gel having a concentration gradient of a gel concentration of 10 to 20% (Multigel 10 to 20, manufactured by Daiichi Pure Chemicals) was used for the polyacrylamide gel, and Pharmacia molecular weight markers were used as the molecular weight markers. Following completion of electrophoresis, the gel was stained with Coomassie brilliant blue R-250, and a uniform band was detected at the location of a molecular weight of about 75 kilodaltons (kDa).

Gel Filtration

The purified enzyme fraction obtained by the method of Example 3 was applied to a Superdex 200 pg column (manufactured by Amersham) pre-equilibrated with 50 mM acetate buffer (pH 4.5) containing 1 M NaCl, and gel filtration was carried out by allowing the same buffer (pH 4.5) containing 1 M NaCl to flow through the column to measure the molecular weight. Pharmacia molecular weight markers were used as standard proteins having known molecular weights to prepare a calibration curve. As a result, the molecular weight of the enzyme was about 150 kDa.

Based on the results of SDS-gel electrophoresis and gel filtration, the enzyme was suggested to be a homodimer having a molecular weight of about 75 kDa.

Example 5

Optimum pH for Enzyme Reaction

The effects of pH were examined in the reaction in which L-alanyl-L-glutamine is formed from L-alanine methyl ester hydrochloride and L-glutamine. Acetate buffer (pH 3.9 to 5.4), MES buffer (pH 5.4 to 6.4), phosphate buffer (pH 6.0 to 7.9), borate buffer (pH 7.8 to 9.3), CAPS buffer (pH 9.3 to 10.7), and $K_2HPO_4$—NaOH buffer (pH 10.8 to 11.6) were used as buffers. 1 microliter (µl) of the Mono S fraction enzyme obtained in Example 3 (about 180 U/ml) was added to 100 µl of each buffer (100 mM) containing 100 mM L-alanine methyl ester, 200 mM L-glutamine and 10 mM EDTA and allowed to react at 18° C. for 5 minutes to measure the effects of pH on the reaction. The results expressed by assigning a value of 100% to the case of using borate buffer (pH 9.3) are shown in FIG. 1. As a result, the optimum pH was found to be 8 to 9.5.

Example 6

Optimum Temperature for Enzyme Reaction

Figure 2:
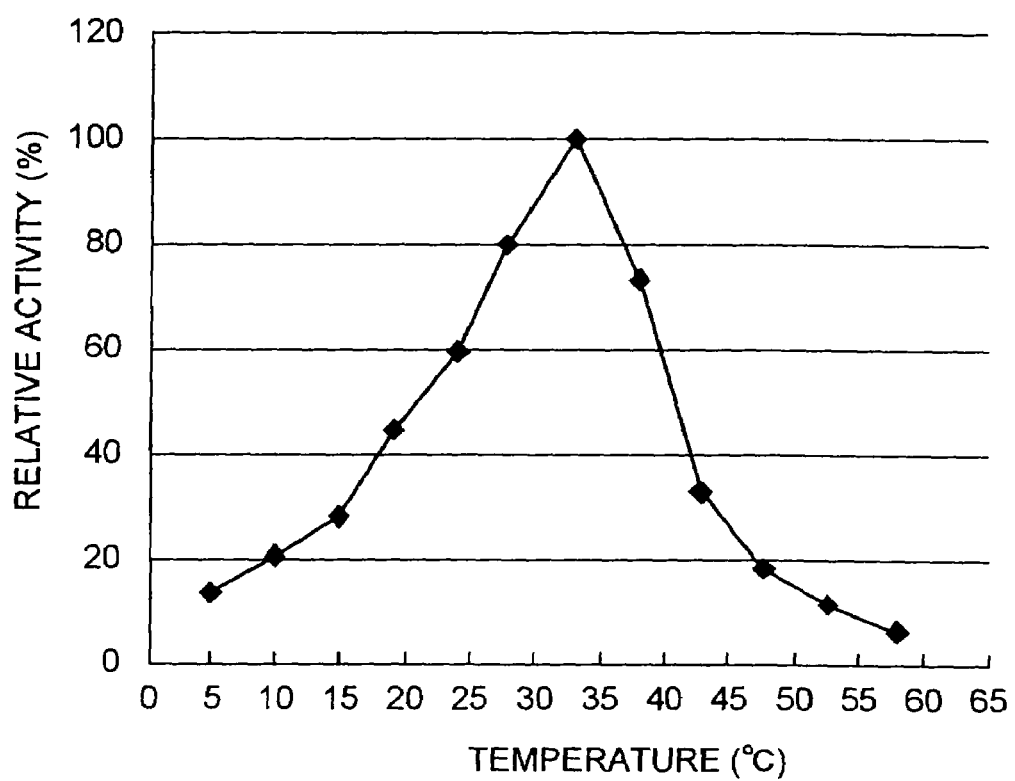
FIG. 2 is a graph illustrating the optimum temperature of the enzyme of *Empedobacter* of the present invention.

The effects of temperature were examined on the reaction in which L-alanyl-L-glutamine is formed from L-alanine methyl ester hydrochloride and L-glutamine. 1 µl of the same enzyme fraction used in Example 5 was added to 100 µl of 100 mM borate buffer (pH 9.0) containing 100 mM L-alanine methyl ester, 200 mM L-glutamine and 10 mM EDTA and allowed to react for 5 minutes at each temperature to measure the effects of temperature on the reaction. The results based on assigning a value of 100% to the activity at 34° C. are shown in FIG. 2. As a result, the optimum temperature was 30 to 40° C.

Example 7

Enzyme Inhibitors

The effects of inhibitors on the production of L-alanyl-L-glutamine were examined using L-alanine methyl ester hydrochloride and L-glutamine as substrates. 2 µl of the same enzyme fraction used in Example 5 was added to 50 µl of 100 mM borate buffer (pH 9.0) containing each of the enzyme inhibitors shown in Table 2 at 10 mM, and allowed to react at 25° C. for 5 minutes. Note that, o-phenanthroline, phenylmethylsulfonyl fluoride and p-nitrophenyl-p'-guanidinobenzoate were dissolved in methanol to a concentration of 50 mM before use. The enzyme activity under each condition was indicated as the relative activity in the case of assigning a value of 100 to the production of L-alanyl-L-glutamine in the absence of enzyme inhibitor. Those results are shown in Table 2. As a result, among the serine enzyme inhibitors tested, the enzyme was not inhibited by phenylmethylsulfonyl fluoride, but it was inhibited by p-nitrophenyl-p'-guanidinobenzoate.

TABLE 2

| | Enzyme inhibitor | Relative activity of L-Ala-L-Gln production (%) |
|---|---|---|
| | None | 100 |
| Metal enzyme inhibitor | EDTA | 96 |
| | o-Phenanthroline | 96 |
| SH enzyme inhibitor | N-Ethyl maleimide | 110 |
| | Monoiodoacetate | 101 |
| Serine enzyme inhibitor | Phenylmethylsulfonyl fluoride | 115 |
| | 4-(2-Aminoethyl)benzene sulfonyl fluoride | 75 |
| | p-Nitrophenyl-p'-guanidino benzoate | 0.1 |

Example 8

Production of L-Alanyl-L-Glutamine from L-Alanine Methyl Ester and L-Glutamine

Figure 3:
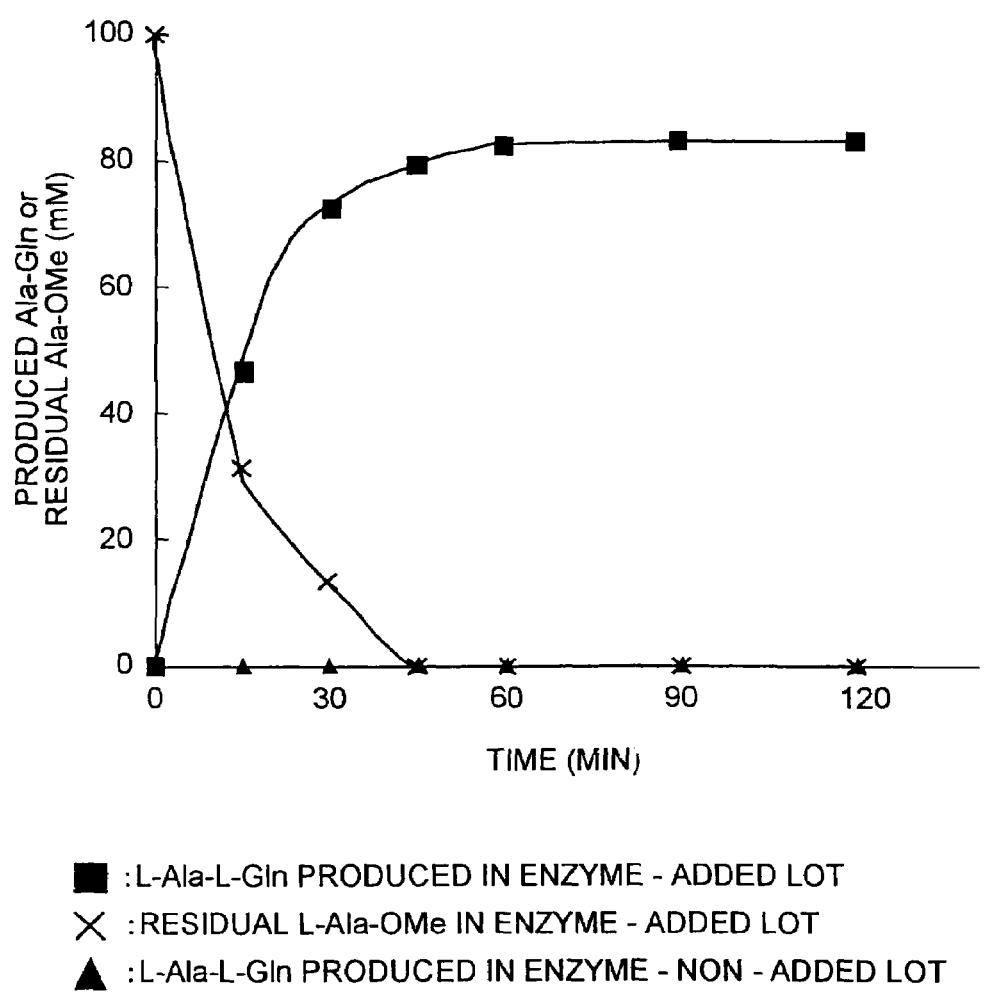
FIG. 3 is a graph illustrating the time course of L-alanyl-L-glutamine production from L-alanine methyl ester and L-glutamine.

3 µl of the same enzyme fraction as used in Example 5 was added to 100 µl of 100 mM borate buffer (pH 9.0) containing 100 mM L-alanine methyl ester hydrochloride, 200 mM L-glutamine and 10 mM EDTA, and allowed to react at 18° C. As a result, as shown in FIG. 3, 83 mM L-alanyl-L-glutamine (L-Ala-L-Gln) was formed in the case of an enzyme-added lot, and the concentration of by-product L-Ala-L-Ala-L-Gln was 1.3 mM. On the other hand, there was scarcely any production of L-Ala-L-Gln observed in an enzyme-non-added lot, and the enzyme concentration was only about 0.07 mM after reacting for 120 minutes.

Example 9

Effects of L-Glutamine Concentration on Production of L-Alanyl-L-Glutamine

1 µl of the same enzyme fraction as used in Example 5 was added to 100 µl of 100 mM borate buffer (pH 9.0) containing 100 mM L-alanine methyl ester hydrochloride, L-glutamine at the concentrations shown in Table 3 and 10 mM EDTA, and allowed to react at 18° C. for 2 hours. Those results are shown in Table 3.

TABLE 3

| L-Alanine methyl ester hydrochloride (mM) | L-Glutamine (mM) | L-Ala-L-Gln (mM) |
|---|---|---|
| 100 | 100 | 68.2 |
| | 110 | 72.1 |
| | 120 | 73.3 |
| | 130 | 75.1 |
| | 150 | 75.5 |
| | 200 | 82.0 |

Example 10

Substrate Specificity of Enzyme (1)

Ester specificity was examined in the case of using L-amino acid ester for the carboxy component. 2 µl of the same enzyme fraction as used in Example 5 was added to 100 µl of 100 mM borate buffer (pH 9.0) containing the carboxy components indicated in Table 4 at 100 mM, 200 mM L-glutamine and 10 mM EDTA, and allowed to react at 25° C. for 2 hours. The amounts of L-Ala-L-Gln formed in this reaction are shown in Table 4. HCl represents hydrochloride in Table 4.

TABLE 4

| Carboxy component | L-Ala-L-Gln formed (mM) |
|---|---|
| L-Alanine methyl ester•HCl | 84.3 |
| L-Alanine ethyl ester•HCl | 91.5 |
| L-Alanine isopropyl ester•HCl | 78.9 |
| L-Alanine-t-butyl ester•HCl | 7.5 |

Example 11

Substrate Specificity of Enzyme (2)

Peptide production was examined in the case of using L-alanine methyl ester for the carboxy component and using various L-amino acids for the amine component. 2 µl of the same enzyme fraction as used in Example 5 was added to 100 µl of 100 mM borate buffer (pH 9.0) containing 100 mM L-alanine methyl ester hydrochloride, the L-amino acids shown in Table 5 at 150 mM and 10 mM EDTA, and allowed to react at 25° C. for 3 hours. The amounts of various peptides formed in this reaction are shown in Table 5. The "+" mark indicates those peptides for which production was confirmed but which were unable to be quantified due to the absence of a standard, while "tr" indicates a trace amount.

TABLE 5

| Amine component | Formed peptide | (mM) |
|---|---|---|
| Gly | L-Ala-Gly | 13.7 |
| L-Ala | L-Ala-L-Ala | 25.4 |
| L-Val | L-Ala-L-Val | 20.8 |
| L-Leu | L-Ala-L-Leu | 45.3 |
| L-Ile | L-Ala-L-Ile | 33.9 |
| L-Met | L-Ala-L-Met | 83.3 |
| L-Phe | L-Ala-L-Phe | 74.4 |
| L-Trp | L-Ala-L-Trp | 53.9 |
| L-Ser | L-Ala-L-Ser | 62.5 |
| L-Thr | L-Ala-L-Thr | 53.9 |
| L-Asn | L-Ala-L-Asn | 65.5 |
| L-Gln | L-Ala-L-Gln | 79.3 |
| L-Tyr | L-Ala-L-Tyr | 17.6 |
| L-CySH | L-Ala-L-CySH | + |
| L-Lys | L-Ala-L-Lys | 71.8 |
| L-Arg | L-Ala-L-Arg | 88.0 |
| L-His | L-Ala-L-His | 66.9 |
| L-Asp | L-Ala-L-Asp | 2.1 |
| L-Glu | L-Ala-L-Glu | 42.9 |
| L-Pro | L-Ala-L-Pro | tr |

Example 12

Substrate Specificity of Enzyme (3)

Peptide production was examined in the case of using various types of L-amino acid methyl esters for the carboxy component and using L-glutamine for the amine component. 2 µl of the same enzyme fraction as used in Example 5 was added to 100 µl of 100 mM borate buffer (pH 9.0) containing the L-amino acid methyl ester hydrochloride salts (AA-OMe-.HCl) shown in Table 6 at 100 mM, 150 mM L-glutamine and 10 mM EDTA, and allowed to react at 25° C. for 3 hours. The amounts of various peptides formed in this reaction are shown in Table 6. The "+" mark indicates those peptides for which production was confirmed but which were unable to be quantified due to the absence of a standard, while "tr" indicates a trace amount. Furthermore, Tween-80 was added to the reaction system to a final concentration of 0.1% in the case of using L-Trp-OMe and L-Tyr-OMe.

TABLE 6

| Carboxy component | Formed peptide | (mM) |
|---|---|---|
| Gly-OMe | Gly-L-Gln | 54.7 |
| L-Ala-OMe | L-Ala-L-Gln | 74.6 |
| L-Val-OMe | L-Val-L-Gln | 15.4 |
| L-Leu-OMe | L-Leu-L-Gln | + |
| L-Ile-OMe | L-Ile-L-Gln | 8.4 |
| L-Met-OMe | L-Met-L-Gln | 12.0 |
| L-Phe-OMe | L-Phe-L-Gln | 0.9 |
| L-Trp-OMe | L-Trp-L-Gln | + |
| L-Ser-OMe | L-Ser-L-Gln | 24.0 |
| L-Thr-OMe | L-Thr-L-Gln | 81.9 |
| L-Asn-OMe | L-Asn-L-Gln | + |
| L-Gln-OMe | L-Gln-L-Gln | 0.3 |
| L-Tyr-OMe | L-Tyr-L-Gln | 3.4 |
| CySH-OMe | L-CySH-L-Gln | + |
| L-Lys-OMe | L-Lys-L-Gln | + |
| L-Arg-OMe | L-Arg-L-Gln | 7.1 |
| L-His-OMe | L-His-L-Gln | + |
| L-Asp-α-OMe | α-L-Asp-L-Gln | tr |
| L-Asp-β-OMe | β-L-Asp-L-Gln | tr |
| L-Glu-α-OMe | α-L-Glu-L-Gln | + |
| L-Glu-γ-OMe | γ-L-Glu-L-Gln | + |
| L-Pro-OMe | L-Pro-L-Gln | 2.2 |

Hydrochloride salts were used for all the carboxy components.

Example 13

Substrate Specificity of Enzyme (4)

Peptide production was examined in the case of using various L-amino acid methyl esters for the carboxy component and various L-amino acids for the amine component. 2 µl of the same enzyme fraction as used in Example 5 was added to 100 µl of 100 mM borate buffer (pH 9.0) containing the L-amino acid methyl ester hydrochloride salts (AA-OMe-.HCl) shown in Table 7 at 100 mM, the L-amino acids shown in Table 7 at 150 mM and 10 mM EDTA, and allowed to react at 25° C. for 3 hours. The amounts formed of each of the peptides formed in this reaction are shown in Table 7. The "tr" indicates a trace amount. Furthermore, Tween-80 was added to the reaction system to a final concentration of 0.1% in the case of using L-Trp-OMe. The "+" mark indicates those peptides for which production was confirmed but which were unable to be quantified due to the absence of a standard.

TABLE 7

| Carboxy component | Amine component | Formed peptide | (mM) |
|---|---|---|---|
| Gly-OMe | L-CySH | Gly-L-CySH | 45.6 |
| | L-Arg | Gly-L-Arg | 25.5 |
| | L-Phe | Gly-L-Phe | 44.0 |
| | L-His | Gly-L-His | 31.6 |
| | L-Lys | Gly-L-Lys | 9.8 |
| | L-Ser | Gly-L-Ser | 44.2 |
| L-Thr-OMe | Gly | L-Thr-Gly | 9.4 |
| | L-Ala | L-Thr-L-Ala | 9.4 |
| | L-Val | L-Thr-L-Val | 0.7 |
| | L-Leu | L-Thr-L-Leu | 28.4 |
| | L-Met | L-Thr-L-Met | 38.6 |
| | L-Ser | L-Thr-L-Ser | 58.2 |

TABLE 7-continued

| Carboxy component | Amine component | Formed peptide | (mM) |
|---|---|---|---|
| L-Ser-OMe | L-Ser | L-Ser-L-Ser | 38.0 |
| | L-Met | L-Ser-L-Met | 12.5 |
| | L-Phe | L-Ser-L-Phe | 20.3 |
| L-Val-OMe | L-Ser | L-Val-L-Ser | 30.8 |
| | L-Met | L-Val-L-Met | 10.3 |
| | L-Phe | L-Val-L-Phe | 6.1 |
| L-Met-OMe | L-Ser | L-Met-L-Ser | 12.8 |
| | L-Met | L-Met-L-Met | 25.0 |
| | L-Phe | L-Met-L-Phe | 34.0 |
| L-Ile-OMe | L-Ser | L-Ile-L-Ser | 17.2 |
| | L-Met | L-Ile-L-Met | 10.0 |
| | L-Phe | L-Ile-L-Phe | 5.2 |
| L-Arg-OMe | L-Ser | L-Arg-L-Ser | 3.6 |
| | L-Met | L-Arg-L-Met | 0.7 |
| | L-Phe | L-Arg-L-Phe | 1.9 |
| L-Leu-OMe | L-Met | L-Leu-L-Met | 12.2 |
| L-Trp-OMe | L-Met | L-Trp-L-Met | 4.1 |
| L-Lys-OMe | L-Met | L-Lys-L-Met | 6.8 |
| L-His-OMe | L-Met | L-His-L-Met | 6.5 |
| L-Asn-OMe | L-Glu | L-Asn-L-Glu | 10.2 |

Hydrochloride salts were used for all the carboxy components.

Example 14

Substrate Specificity of Enzyme (5)

Peptide production was examined in the case of using the L or D forms of various amino acid methyl esters for the carboxy component, and the L or D forms of various amino acids for the amine component. 2 µl of the same enzyme fraction as used in Example 5 was added to 100 µl of 100 mM borate buffer (pH 9.0) containing the various amino acid methyl ester hydrochloride salts (M-OMe.HCl) shown in Table 8 at 100 mM, the various amino acids shown in Table 8 at 150 mM and 10 mM EDTA, and allowed to react at 25° C. for 3 hours. The amounts of various peptides formed in this reaction are shown in Table 8. The "tr" indicates a trace amount.

TABLE 8

| Carboxy component | Amine component | Formed peptide | (mM) |
|---|---|---|---|
| D-Ala-OMe | L-Gln | D-Ala-L-Gln | 69.3 |
| D-Ala-OMe | L-Ser | D-Ala-L-Ser | 20.3 |
| D-Thr-OMe | | D-Thr-L-Ser | 1.0 |
| D-Ser-OMe | | D-Ser-L-Ser | 3.3 |
| D-Val-OMe | | D-Val-L-Ser | 0.6 |
| D-Met-OMe | | D-Met-L-Ser | 5.1 |
| L-Ala-OMe | D-Gln | L-Ala-D-Gln | 0.3 |
| L-Ala-OMe | D-Ser | L-Ala-D-Ser | 5.4 |
| L-Thr-OMe | | L-Thr-D-Ser | 6.9 |
| L-Ser-OMe | | L-Ser-D-Ser | 16.2 |
| L-Val-OMe | | L-Val-D-Ser | 1.4 |
| L-Met-OMe | | L-Met-D-Ser | 1.9 |
| D-Ala-OMe | D-Gln | D-Ala-D-Gln | tr |
| D-Ala-OMe | D-Ser | D-Ala-D-Ser | 0.2 |
| D-Thr-OMe | | D-Thr-D-Ser | 1.1 |
| D-Ser-OMe | | D-Ser-D-Ser | 2.5 |
| D-Val-OMe | | D-Val-D-Ser | 0.5 |
| D-Met-OMe | | D-Met-D-Ser | 2.7 |

Hydrochloride salts were used for all the carboxy components.

Example 15

Substrate Specificity of Enzyme (6)

Peptide production was examined using various L-amino acid amides for the carboxy component, and various L-amino acids for the amine component. 2 µl of the same enzyme fraction as that used in Example 5 was added to 100 µl of 100 mM borate buffer (pH 9.0) containing the L-amino acid amide hydrochloride salts (AA-NH$_2$.HCl) shown in Table 9 at 100 mM, the L-amino acids shown in Table 9 at 150 mM and 10 mM EDTA, and allowed to react at 25° C. for 3 hours. The amounts of various peptides formed in this reaction are shown in Table 9.

TABLE 9

| Carboxy component | Amine component | Formed peptide | (mM) |
|---|---|---|---|
| L-Phe-NH$_2$ | L-Gln | L-Phe-L-Gln | 0.2 |
| L-Phe-NH$_2$ | L-Ser | L-Phe-L-Ser | 0.6 |
| L-Ala-NH$_2$ | L-Gln | L-Ala-L-Gln | 7.6 |
| L-Ala-NH$_2$ | L-Met | L-Ala-L-Met | 3.4 |
| L-Ala-NH$_2$ | L-His | L-Ala-L-His | 3.9 |
| L-Thr-NH$_2$ | L-Gln | L-Thr-L-Gln | 0.3 |

Example 16

Substrate Specificity of Enzyme (7)

Peptide production was examined in the case of using various L-alanine methyl esters for the carboxy component and C-protected L-amino acids for the amine component. 2 µl of the same enzyme fraction as used in Example 5 was added to 100 µl of 100 mM borate buffer (pH 9.0) containing the L-alanine methyl ester hydrochloride salt (Ala-OMe.HCl) shown in Table 10 at 100 mM, the L-amino acid amide hydrochloride salts shown in Table 10 at 150 mM and 10 mM EDTA, and allowed to react at 25° C. for 3 hours. The amounts of various peptides formed in this reaction are shown in Table 10.

TABLE 10

| Carboxy component | Amine component | Formed peptide | (mM) |
|---|---|---|---|
| L-Ala-OMe | Gly-NH$_2$ | L-Ala-Gly-NH$_2$ | 7.4 |
| | L-Ala-NH$_2$ | L-Ala-L-Ala-NH$_2$ | 8.3 |
| | L-Phe-NH$_2$ | L-Ala-L-Phe-NH$_2$ | 12.2 |

Example 17

Substrate Specificity of Enzyme (8)

Peptide production was examined in the case of using various amino acid methyl esters for the carboxy component and methylamine for the amine component. 2 µl of the same enzyme fraction as used in Example 5 was added to 100 µl of 100 mM borate buffer (pH 9.0) containing the amino acid methyl ester hydrochloride salts (AA-OMe.HCl) shown in Table 11 at 100 mM, the methylamine shown in Table 11 at 150 mM and 10 mM EDTA, and allowed to react at 25° C. for 3 hours. The amounts of various peptides formed in this reaction are shown in Table 11.

TABLE 11

| Carboxy component | Amine component | Formed peptide | (mM) |
|---|---|---|---|
| Gly-OMe | Methylamine | Gly-methylamine | 1.1 |
| L-Thr-OMe | | L-Thr-methylamine | 0.2 |
| L-Ala-OMe | | L-Ala-methylamine | 0.3 |

Example 18

Substrate Specificity of Enzyme (9)

Peptide production was examined in the case of using β-amino acid ester for the carboxy component or β-amino acid for the amine component. 2 μl of the same enzyme fraction as used in Example 5 was added to 100 μl of 100 mM borate buffer (pH 9.0) containing the carboxy components shown in Table 12 at 100 mM, the amine components shown in Table 12 at 150 mM and 10 mM EDTA, and allowed to react at 25° C. for 3 hours. The amounts of various peptides formed in this reaction are shown in Table 12. The "tr" indicates a trace amount.

TABLE 12

| Carboxy component | Amine component | Formed peptide | (mM) |
|---|---|---|---|
| Gly-OMe | β-Ala | Gly-β-Ala | 2.2 |
| Gly-OMe | β-Phe | Gly-β-Phe | 0.4 |
| L-Ala-OMe | β-Ala | Ala-β-Ala | 7.7 |
| L-Ala-OMe | β-Phe | Ala-β-Phe | 1.4 |
| L-Thr-OMe | β-Ala | Thr-β-Ala | 3.2 |
| L-Thr-OMe | β-Phe | Thr-β-Phe | 1.4 |
| β-Ala-OMe | L-α-Ala | β-Ala-L-α-Ala | tr |
| β-Ala-OMe | β-Ala | β-Ala-β-Ala | 0.2 |
| β-Ala-OMe | L-Gln | β-Ala-L-Gln | 0.6 |
| β-Ala-OMe | L-Ser | β-Ala-L-Ser | 3.2 |

Hydrochloride salts were used for all of the carboxy components.

Example 19

Substrate Specificity of Enzyme (10)

Oligopeptide production was examined in the case of using L-amino acid ester for the carboxy component and peptide for the amine component. 2 μl of the same enzyme fraction as used in Example 5 was added to 100 μl of 100 mM borate buffer (pH 9.0) containing the carboxy components shown in Table 13 at 100 mM, the amine components shown in Table 13 at 150 mM and 10 mM EDTA, and allowed to react at 25° C. for 3 hours. The amounts of various peptides formed in this reaction are shown in Table 13. As a result, it was clearly demonstrated that the present enzyme can form not only dipeptide, but also long-chain peptides by using a peptide for the amine component.

As has been indicated in the aforementioned Examples 9 to 20, the present enzyme obtained from *Empedobacter brevis* strain FERM BP-18545 was determined to have extremely broad substrate specificity.

TABLE 13

| Carboxy component | Amine component | Produced peptide | (mM) |
|---|---|---|---|
| L-Ala-OMe | L-Ala | L-Ala-L-Ala | 28.7 |
| | L-Ala-L-Ala | L-Ala-L-Ala-L-Ala | 57.5 |
| | L-Ala-L-Ala-L-Ala | L-Ala-L-Ala-L-Ala-L-Ala | 44.5 |
| | L-Ala-L-Ala-L-Ala-L-Ala | L-Ala-L-Ala-L-Ala-L-Ala-L-Ala | 34.8 |
| | L-Ala-L-Ala-L-Ala-L-Ala-L-Ala | L-Ala-L-Ala-L-Ala-L-Ala-L-Ala-L-Ala | 1.4* |
| | L-Ala-L-Gln | L-Ala-L-Ala-L-Gln | 15.2 |
| | Gly-L-Ala | L-Ala-Gly-L-Ala | 25.9 |
| | Gly-Gly | L-Ala-Gly-Gly | 41.7 |
| | L-His-L-Ala | L-Ala-L-His-L-Ala | 55.9 |
| | L-Leu-L-Ala | L-Ala-L-Leu-L-Ala | 48.3 |
| | L-Phe-L-Ala | L-Ala-L-Phe-L-Ala | 49.7 |
| | L-Phe-Gly | L-Ala-L-Phe-Gly | 43.7 |
| Gly-OMe | L-Ala-L-Tyr | Gly-L-Ala-L-Tyr | 1.7 |
| | Gly-L-Gln | Gly-Gly-L-Gln | 7.2 |
| | Gly-L-Tyr-L-Ala | Gly-Gly-L-Tyr-L-Ala | 44.2 |
| L-Thr-OMe | Gly-Gly | L-Thr-Gly-Gly | 83.0 |

*Since the solubility of L-Ala-L-Ala-L-Ala-L-Ala-L-Ala was low, the carboxy component was used at a concentration of 10 mM and the amine component was used at 15 mM in this reaction system. The other conditions were the same as those explained in the example. Hydrochloride salts were used for all the carboxy components.

Example 20

Comparison of Ability to Catalyze Peptide Formation with Known Enzymes

The peptide-forming ability of the present enzyme was compared with that of known enzymes. Carboxypeptidase Y described in EP 278787A1 and the thiol endopeptidases (ficin, papain, bromelain, and chymopapain) described in EP 359399B1 were used as the known enzymes, and they were used in the form of purified enzymes (manufactured by Sigma). The enzyme uniformly purified in Example 3 was used as a source of the present enzyme of the present invention. These enzymes were added to a reaction system in the protein amounts shown in Table 14. The reaction was carried out by adding the enzyme to 100 μl of borate buffer (pH 9.0) containing 100 mM L-alanine methyl ester hydrochloride and 200 mM L-glutamine and allowing the resultant to react at 25° C. Note that the carboxypeptidase used was one dissolved in 10 mM acetate buffer (pH 5.0) containing 1 mM EDTA, while the thiol endopeptidase used was one dissolved in 10 mM acetate buffer (pH 5.0) containing 2 mM EDTA, 0.1 M KCl, and 5 mM dithiothreitol. The ratios of the production rates of L-alanyl-L-glutamine by these enzymes are shown in Table 14.

As a result, the production of an extremely trace small amount of L-alanyl-L-glutamine was observed even in the absence of enzymes, while a slight increase in the production rate was observed in the section where carboxypeptidase- or thiol endopeptidase-added lot as compared with the enzyme-non-added lot. In contrast, an overwhelmingly higher rate of production of L-alanyl-L-glutamine was observed in the enzyme-added lot, and that rate of production was about 5,000 to 100,000 times higher than those of carboxypeptidase Y and of thiol endopeptidase. As has been described above, the present enzyme was verified to have an extremely high peptide production rate unlike any known enzyme in the prior art. Furthermore, the enzyme of the present invention is a dimer having a molecular weight of about 75,000. In contrast, the molecular weight of the carboxypeptidase Y has been reported to be about 61,000, while the molecular weight of thiol endopeptidase has been reported to be about 23,000 to 36,000. Thus, the L-alanyl-L-glutamine production rate of the enzyme of the present invention as compared to those of the carboxypeptidase Y and the thiol endopeptidase is even greater when the rate is expressed per molecular weight than when it is expressed per unit weight as indicated in the examples.

TABLE 14

| Enzyme | Amount of enzyme added (protein mg/ml) | L-Ala-L-Gln production rate (mM/min) | Ratio of L-Ala-L-Gln production rate per enzyme unit weight |
| --- | --- | --- | --- |
| No enzyme | 0 | 0.0006 | |
| Carboxypeptidase Y | 0.61 | 0.0257 | 0.0191 |
| Ficin | 2.60 | 0.0096 | 0.0017 |
| Papain | 2.30 | 0.0106 | 0.0021 |
| Bromelain | 2.80 | 0.0062 | 0.0010 |
| Chymopapain | 3.60 | 0.0100 | 0.0013 |
| Enzyme of present invention | 0.02 | 4.4000 | 100.0 |

Example 21

Production of L-Alanyl-L-Glutamine Using Microbial Cell of *Sphingobacterium* sp A 50 ml medium (pH 7.0) containing 5 g of glucose, 5 g of ammonium sulfate, 1 g of monopotassium phosphate, 3 g of dipotassium phosphate, 0.5 g of magnesium sulfate, 10 g of yeast extract, and 10 g of peptone in 1 L was transferred to a 500 mL Sakaguchi flask and sterilized at 115° C. for 15 minutes for culturing *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). This was then inoculated with one loopful cells of *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) cultured at 30° C. for 24 hours in a slant agar medium (agar: 20 g/L, pH 7.0) containing 5 g of glucose, 10 g of yeast extract, 10 g of peptone and 5 g of NaCl in 1 L, followed by shake culturing at 30° C. for 20 hours and 120 strokes/minute. 1 ml of this culture broth was then added to the aforementioned medium (50 ml/500 mL Sakaguchi flask) and cultured at 30° C. for 18 hours. Following completion of the culturing, the microbial cells were separated from the culture broth by centrifugation and suspended in 0.1 M borate buffer (pH 9.0) containing 10 mM EDTA at a concentration of 100 g/L as wet microbial cells. 0.1 mL of 100 mM borate buffer (pH 9.0) containing 10 mM EDTA, 200 mM L-alanyl methyl ester hydrochloride and 400 mM L-glutamine was then added to 0.1 mL of this microbial cell suspension. The resulting 0.2 mL of mixture was allowed to react at 25° C. for 120 minutes. The concentration of L-alanyl-L-glutamine formed at this time was 62 mM.

Example 22

Purification of Enzyme from *Sphingobacterium* sp

The following procedure after centrifugation was carried out either on ice or at 4° C. *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultured in the same manner as Example 21, and the microbial cells were collected by centrifugation (10,000 rpm, 15 minutes). After washing 2 g of microbial cells with 20 mM Tris-HCl buffer (pH 7.6), they were suspended in 8 ml of the same buffer and subjected to ultrasonic disrupting treatment for 45 minutes at 195 W. This ultrasonically disrupted liquid was then centrifuged (10,000 rpm, 30 minutes) to remove the cell debris and obtain an ultrasonically disrupted liquid supernatant. This ultrasonically disrupted liquid supernatant was dialyzed overnight against 20 mM Tris-HCl buffer (pH 7.6) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 7.6), and the active fraction was collected from the non-adsorbed fraction. This active fraction was dialyzed overnight against 20 mM acetate buffer (pH 5.0) followed by removal of the insoluble fraction by centrifugation (10,000 rpm, 30 minutes) to obtain a dialyzed fraction in the form of the supernatant liquid. This dialyzed fraction was then applied to an SP-Sepharose HP column (manufactured by Amersham) pre-equilibrated with 20 mM acetate buffer (pH 5.0) to obtain the active fraction in which enzyme was eluted at a linear concentration gradient of the same buffer containing 0 to 1 M NaCl.

Example 23

Production of L-Alanyl-L-Glutamine Using Enzyme Fraction

10 μl of the SP-Sepharose HP fraction (about 27 U/ml) purified in Example 22 was added to 90 μl of 111 mM borate buffer (pH 9.0) containing 111 mM L-alanine methyl ester hydrochloride, 222 mM L-glutamine and 11 mM EDTA, and allowed to react at 25° C. for 120 minutes. As a result, 73 mM of L-alanyl-L-glutamine was formed in the enzyme-added lot. On the other hand, there was scarcely any production of L-Ala-L-Glu observed in the enzyme-non-added lot, and the production amount was only about 0.07 mM after reacting for 120 minutes.

Example 24

Substrate Specificity of Enzyme (11)

Substrate specificity was examined for enzyme derived from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). 100l of 100 mM borate buffer (pH 9.0) containing the various carboxy components at a final concentration of 100 mM and the various amine components at a final concentration of 150 mM shown in Tables 15-1 to 15-4, the SP-Sepharose HP fraction enzyme purified in Example 22 (addition of 0.33 units in the reaction liquid) and 10 mM EDTA were allowed to react at 25° C. for 1.5 hours. The amounts of various peptides formed in this reaction are shown in Table 15. The "+" mark indicates those peptides for which production was confirmed but which were unable to be quantified due to the absence of a standard, while "tr" indicates a trace amount. Furthermore, Tween-80 was added to the reaction system to a final concentration of 0.1% in the case of using L-Tyr-OMe. In addition, hydrochloride salts were used for all carboxy components.

TABLE 15-1

| Carboxy component | Amine component | Produced peptide | (mM) |
|---|---|---|---|
| L-Ala-OMe | Gly | L-Ala-Gly | 11.1 |
| | L-Ala | L-Ala-L-Ala | 13.1 |
| | L-Val | L-Ala-L-Val | 10.9 |
| | L-Leu | L-Ala-L-Leu | 33.0 |
| | L-Ile | L-Ala-L-Ile | 24.7 |
| | L-Met | L-Ala-L-Met | 86.9 |
| | L-Pro | L-Ala-L-Pro | 1.5 |
| | L-Phe | L-Ala-L-Phe | 69.5 |
| | L-Trp | L-Ala-L-Trp | 46.0 |
| | L-Thr | L-Ala-L-Thr | 47.3 |
| | L-Asn | L-Ala-L-Asn | 52.3 |
| | L-Tyr | L-Ala-L-Tyr | 11.1 |
| | L-CySH | L-Ala-L-CySH | + |
| | L-Lys | L-Ala-L-Lys | 71.2 |
| | L-Arg | L-Ala-L-Arg | 72.2 |
| | L-His | L-Ala-L-His | 73.6 |
| | L-Asp | L-Ala-L-Asp | 2.3 |
| | L-Glu | L-Ala-L-Glu | 39.1 |
| | L-Ser | L-Ala-L-Ser | 43.8 |
| | D-Ser | L-Ala-D-Ser | 3.3 |
| D-Ala-OMe | L-Ser | D-Ala-L-Ser | 24.1 |
| | D-Ser | D-Ala-D-Ser | 5.5 |

TABLE 15-2

| Carboxy component | Amine component | Produced peptide | (mM) |
|---|---|---|---|
| L-Thr-OMe | L-Gln | L-Thr-L-Gln | 36.1 |
| Gly-OMe | | Gly-L-Gln | 61.1 |
| L-Ser-OMe | | L-Ser-L-Gln | 12.9 |
| L-Val-OMe | | L-Val-L-Gln | 8.2 |
| L-Met-OMe | | L-Met-L-Gln | 32.6 |
| L-Ile-OMe | | L-Ile-L-Gln | 6.4 |
| L-Arg-OMe | | L-Arg-L-Gln | 17.2 |

TABLE 15-2-continued

| Carboxy component | Amine component | Produced peptide | (mM) |
|---|---|---|---|
| L-Tyr-OMe | | L-Tyr-L-Gln | 0.6 |
| L-Pro-OMe | | L-Pro-L-Gln | 1.8 |
| L-Phe-OMe | | L-Phe-L-Gln | 0.8 |
| L-Gln-OMe | | L-Gln-L-Gln | 0.1 |
| Asp-α-OMe | | α-L-Asp-L-Gln | 0.05 |

TABLE 15-3

| Carboxy component | Amine component | Produced peptide | (mM) |
|---|---|---|---|
| L-Thr-OMe | Gly | L-Thr-Gly | 0.4 |
| | L-Ala | L-Thr-L-Ala | 5.8 |
| | L-Val | L-Thr-L-Val | 1.3 |
| | L-Leu | L-Thr-L-Leu | 15.3 |
| | L-Met | L-Thr-L-Met | 28.9 |
| Gly-OMe | L-Arg | Gly-L-Arg | 17.9 |
| | L-Phe | Gly-L-Phe | 20.0 |
| | L-His | Gly-L-His | 36.2 |
| | L-Lys | Gly-L-Lys | 48.2 |
| | L-Ser | Gly-L-Ser | 53.8 |
| L-Ser-OMe | L-Ser | L-Ser-L-Ser | 9.9 |
| | L-Met | L-Ser-L-Met | 7.6 |
| | L-Phe | L-Ser-L-Phe | 4.3 |
| L-Val-OMe | L-Ser | L-Val-L-Ser | 31.9 |
| | L-Met | L-Val-L-Met | 6.8 |
| | L-Phe | L-Val-L-Phe | 1.0 |
| L-Met-OMe | L-Ser | L-Met-L-Ser | 25.3 |
| | L-Met | L-Met-L-Met | 28.4 |
| | L-Phe | L-Met-L-Phe | 8.9 |
| L-Ile-OMe | L-Ser | L-Ile-L-Ser | 17.3 |
| | L-Met | L-Ile-L-Met | 5.1 |
| | L-Phe | L-Ile-L-Phe | 1.5 |
| L-Arg-OMe | L-Ser | L-Arg-L-Ser | 2.2 |
| | L-Met | L-Arg-L-Met | tr |
| | L-Phe | L-Arg-L-Phe | tr |

TABLE 15-4

| Carboxy component | Amine component | Produced peptide | (mM) |
|---|---|---|---|
| L-Ala-OMe | Gly amide | L-Ala-Gly amide | 15.1 |
| | L-Ala amide | L-Ala-L-Ala amide | 9.2 |
| | L-Phe amide | L-Ala-Phe amide | 27.1 |
| L-Ala-OMe | Methylamine | L-Ala-methylamine | 0.6 |
| L-Thr-OMe | | L-Thr-methylamine | 0.3 |
| Gly-OMe | | Gly-methylamine | 1.0 |
| L-Ala amide | L-Gln | L-Ala-L-Gln | 0.3 |
| | L-Met | L-Ala-L-Met | tr |
| | L-His | L-Ala-L-His | tr |

Hydrochloride salts were used for all the amino acid amides.

Example 25

Substrate Specificity of Enzyme (12)

Substrate specificity with respect to oligopeptide production was examined for enzyme derived from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). 100 µl of 100 mM borate buffer (pH 9.0) containing the various carboxy components at a final concentration of 100 mM and the various amine components at a final concentration of 150 mM shown in Table 16, the SP-Sepharose HP fraction enzyme purified in Example 22 (addition of 0.33 units in the reaction liquid) and 10 mM EDTA were allowed to react for 1.5 hours at 25° C. The amounts of each oligopeptide formed in this reaction are shown in Table 16. Furthermore, hydrochloride salts were used for all carboxy components.

Abbreviations

H-Ala-OMe: L-alanine methyl ester hydrochloride

H-p-F-Phe-OMe: p-fluoro-L-phenylalanine methyl ester hydrochloride

H—Cl—F-Phe-OMe: p-chloro-L-phenylalanine methyl ester hydrochloride

H-p-$NO_2$-Phe-OMe: p-nitro-L-phenylalanine methyl ester hydrochloride

TABLE 16

| Carboxy component | Amine component | Produced peptide | (mM) |
|---|---|---|---|
| L-Ala-OMe | L-Ala | L-Ala-L-Ala | 25.6 |
|  | L-Ala-L-Ala | L-Ala-L-Ala-L-Ala | 41.1 |
|  | L-Ala-L-Ala-L-Ala | L-Ala-L-Ala-L-Ala-L-Ala | 30.1 |
|  | L-Ala-L-Ala-L-Ala-L-Ala | L-Ala-L-Ala-L-Ala-L-Ala-L-Ala | 22.8 |
|  | Gly-Gly | L-Ala-Gly-Gly | 33.7 |
|  | Gly-Ala | L-Ala-Gly-L-Ala | 35.1 |
|  | L-His-L-Ala | L-Ala-L-His-L-Ala | 58.0 |
|  | L-Phe-Gly | L-Ala-L-Phe-Gly | 34.0 |
|  | L-Leu-L-Ala | L-Ala-L-Leu-L-Ala | 40.7 |
|  | L-Phe-L-Ala | L-Ala-L-Phe-L-Ala | 24.8 |
| L-Thr-OMe | Gly-Gly | L-Thr-Gly-Gly | 8.4 |
| Gly-OMe | L-Ala-L-Tyr | Gly-L-Ala-L-Tyr | 0.6 |

Example 26

Substrate Specificity of Enzyme (13)

Substrate specificity was additionally assessed using the same enzyme fraction as that used in Example 5.

H-t-Leu-OMe: tert-L-leucine methyl ester hydrochloride

H-2-Nal-OMe: 3-(2-naphthyl)-L-alanine methyl ester hydrochloride

H-Aib-OMe: α-aminoisobutyric acid methyl ester hydrochloride

TABLE 17

| Carboxy component | (mM) | Amine component | (mM) | Produced peptide | (mM) | Reaction time (hr) |
|---|---|---|---|---|---|---|
| H-Ala-OMe | 50 mM | H-p-F-Phe-OH | 50 mM | H-Ala-p-F-Phe-OH | 21.9 mM | 3 |
| H-Ala-OMe | 40 mM | H-Cl-F-Phe-OH | 40 mM | H-Ala-Cl-F-Phe-OH | 20.8 mM | 3 |
| H-Ala-OMe | 40 mM | H-p-$NO_2$-Phe-OH | 40 mM | H-Ala-p-$NO_2$-Phe-OH | 27.5 mM | 3 |
| H-Ala-OMe | 100 mM | H-t-Leu-OH | 150 mM | H-Ala-t-Leu-OH | 0.4 mM | 3 |
| H-Ala-OMe | 20 mM | H-2-Nal-OH | 20 mM | H-Ala-2-Nal-OH | + | 3 |
| H-p-F-Phe-OMe | 100 mM | H-Gln-OH | 150 mM | H-p-F-Phe-H-Gln-OH | tr | 3 |
| H-Cl-F-Phe-OMe | 25 mM | H-Gln-OH | 50 mM | H-Cl-F-Phe-H-Gln-OH | tr | 3 |
| H-p-$NO_2$-Phe-OMe | 40 mM | H-Gln-OH | 40 mM | H-p-$NO_2$-Phe-H-Gln-OH | 1.1 mM | 3 |
| H-t-Leu-OMe | 100 mM | H-Gln-OH | 150 mM | H-t-Leu-H-Gln-OH | tr | 3 |
| H-2-Nal-OMe | 40 mM | H-Gln-OH | 40 mM | H-2-Nal-H-Gln-OH | tr | 3 |
| H-Aib-OMe | 100 mM | H-Gln-OH | 150 mM | H-Aib-H-Gln-OH | 18.8 mM | 3 |
| H-N-Me-Ala-OMe | 100 mM | H-Gln-OH | 150 mM | H-N-Me-Ala-H-Gln-OH | 0.5 mM | 3 |
| H-Aib-OMe | 100 mM | H-Phe-OH | 150 mM | H-Aib-Phe-OH | 17.2 mM | 3 |
| H-CHA-OMe | 40 mM | H-Phe-OH | 40 mM | H-CHA-Phe-OH | + | 3 |
| H-N-Me-Ala-OMe | 100 mM | H-Phe-OH | 150 mM | H-N-Me-Ala-Phe-OH | tr | 3 |
| H-Ala-OMe | 100 mM | H-Ser(tBu)-OH | 150 mM | H-Ala-Ser(tBu)-OH | 48.8 mM | 2 |
| H-Ser(tBu)-OMe | 100 mM | H-Gln-OH | 150 mM | H-Ser(tBu)-Gln-OH | tr | 2 |
| H-Ala-OMe | 100 mM | H-Asp(OtBu)-OH | 150 mM | H-Ala-Asp(OtBu)-OH | 62.6 mM | 2 |
| H-Asp(OtBu)-OMe | 100 mM | H-Gln-OH | 150 mM | H-Asp(OtBu)-Gln-OH | 0.9 mM | 2 |
| H-Ala-OMe | 100 mM | H-Lys(Boc)-OH | 150 mM | H-Ala-Lys(Boc)-OH | 51.0 mM | 2 |
| H-Lys(Boc)-OMe | 100 mM | H-Gln-OH | 150 mM | H-Lys(Boc)-Gln-OH | + | 2 |

100 μl of reaction solutions consisting of 100 mM borate buffer (pH 9.0) containing each of the carboxy components and amine components at the final concentrations shown in Table 17, enzyme (addition of 0.1 unit in reaction solution) and 10 mM EDTA were allowed to react at 25° C. for the reaction times shown in Table 17. The amounts of various peptides formed in the reactions are shown in Table 17. The "+" mark indicates those for which production was confirmed but which were unable to be quantified due to the absence of a standard, while "tr" indicates a trace amount.

H—N-Me-Ala-OMe: N-methyl-L-alanine methyl ester hydrochloride

H—CHA-OMe: β-cyclohexyl-L-alanine methyl ester hydrochloride

H-Ser(tBu)-OMe: O-tert-butyl-L-serine methyl ester hydrochloride

H-Asp(OtBu)-OMe: L-aspartic acid β-tert-butyl ester α-methyl ester hydrochloride H-Lys(Boc)-OMe: N-ε-tert-butoxycarbonyl-L-lysine methyl ester hydrochloride H-p-F-Phe-OH: p-fluoro-L-phenylalanine
H—Cl—F-Phe-OH: p-chloro-L-phenylalanine
H-p-NO$_2$-Phe-OH: p-nitro-L-phenylalanine
H-t-Leu-OH: tert-L-leucine
H-2-NaI-OH: 3-(2-naphthyl)-L-alanine
H-Gln-OH: L-glutamine
H-Phe-OH: L-phenylalanine
H-Ser(tBu)—OH: O-tert-butyl-L-serine
H-Asp(OtBu)—OH: L-aspartic acid β-tert-butyl ester
H-Lys(Boc)-OH: N-ε-tert-butoxycarbonyl-L-lysine Example 27

Substrate Specificity of Enzyme (14)

Substrate specificity with respect to oligopeptide production was assessed using the same enzyme fraction as Example 5 (derived from *Empedobacter brevis*). 100 μl of reaction solutions consisting of 100 mM borate buffer (pH 9.0) containing each of the carboxy components and amine components at the final concentrations shown in Table 18, enzyme (the numbers of units added to the reaction solution are described in Table 18) and 10 mM EDTA were allowed to react at 25° C. for 3 hours. The amounts of various oligopeptides formed in the reactions are shown in Table 18. A "+" mark indicates those for which production was confirmed but which were unable to be quantified due to the absence of a standard, while "tr" indicates a trace amount. It should be noted that hydrochloride salts were used for all the carboxy components.

TABLE 18

| Carboxy component | Amine component | Amount of enzyme (unit) | Produced peptide | (mM) |
|---|---|---|---|---|
| Gly-OMe | L-Phe-L-Met | 1.0 | Gly-Phe-Met | 13.3 |
| L-Ala-OMe | L-Phe-L-Met | 0.2 | L-Ala-L-Phe-L-Met | + |
| L-Tyr-OMe | Gly-Gly-L-Phe-L-Met | 1.0 | L-Tyr-Gly-Gly-L-Phe-L-Met | 2.7 |
| L-Ala-OMe | Gly-Gly-L-Phe-L-Met | 0.2 | L-Ala-Gly-Gly-L-Phe-L-Met | + |
| Gly-OMe | Gly-L-Phe | 0.1 | Gly-L-Phe | 17.3 |
| L-Ala-OMe | Gly-L-Phe | 0.1 | L-Ala-Gly-L-Phe | + |
| D-Ala-OMe | Gly-L-Phe | 0.1 | D-Ala-Gly-L-Phe | Tr |

Example 28 Isolation of Peptide-Forming Enzyme Gene Derived from *Empedobacter brevis*

Hereinafter, although the following provides a description of the isolation of a peptide-forming enzyme gene, will be explained. As the microbe was used *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was used as the microbe. In isolating the gene, *Escherichia coli* JM-109 was used as a host while pUC118 was used as a vector.

(1) Production of PCR Primer Based on Determined Internal Amino Acid Sequence

A mixed primer having the base sequences indicated in SEQ ID NO.: 3 and SEQ ID NO: 4, respectively, was produced based on the amino acid sequences (SEQ ID NOs: 1 and 2) determined according to the Edman's decomposition method from the a digestion product of lysyl endopeptidase of a peptide-forming enzyme derived from the *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) digested by a lysyl endopeptidase.

(2) Preparation of Microbial Cells

*Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was cultured at 30° C. for 24 hours on a CM2G agar medium (containing glucose at 50 g/l, yeast extract at 10 g/l, peptone at 10 g/l, sodium chloride at 5 g/l, and agar at 20 g/l, pH 7.0). One loopful of the resulting microbial cells was inoculated into a 500 ml Sakaguchi flask containing 50 ml of a CM2G liquid medium (the aforementioned medium excluding agar) followed by shake culturing at 30° C.

(3) Preparation of Chromosomal DNA from Microbial Cells

First, 50 ml of culture broth was centrifuged (12,000 rpm, 4° C., 15 minutes) to collect the microbial cells. Then, a chromosomal DNA was obtained from the microbial cells using the QIAGEN Genomic-Tip System (Qiagen) based on the procedure described in the manual therefor.

(4) Preparation of DNA Fragment Containing Part of Peptide-Forming Enzyme Gene by PCR A DNA fragment containing a portion of the peptide-forming enzyme gene derived from *Empedobacter brevis* strain FERM BP-8113 (Depositary institution: the independent administrative corporation, National Institute of Advanced Industrial Science and Technology, International Patent Organism Depositary, Address of depositary institution: Dai-6, 1-1 Higashi 1-Chome, Tsukuba-shi, Ibaraki-ken, Japan, International deposit transfer date: Jul. 8, 2002) was obtained by the PCR method using LA-Taq (manufactured by Takara Shuzo). A PCR reaction was then carried out on a chromosomal DNA obtained from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) using the primers having the base sequences of SEQ ID NOs: 3 and 4.

The PCR reaction was carried out for 30 cycles under the following conditions using the Takara PCR Thermal Cycler PERSONAL (manufactured by Takara Shuzo).

| | |
|---|---|
| 94° C. | 30 seconds |
| 52° C. | 1 minute |
| 72° C. | 1 minute |

After the reaction, 3 μl of the reaction liquid was applied to 0.8% agarose electrophoresis. As a result, it was verified that a DNA fragment of about 1.5 kilobases (kb) was confirmed to be amplified.

(5) Cloning of Peptide-Forming Enzyme Gene from Gene Library

In order to obtain the entire length of peptide-forming enzyme gene in full-length, Southern hybridization was carried out using the DNA fragment amplified in the PCR procedure as a probe. The procedure for Southern hybridization is explained in Molecular Cloning, 2nd edition, Cold Spring Harbor Press (1989).

The approximately 1.5 kb DNA fragment amplified by the PCR procedure was isolated by 0.8% agarose electrophoresis. The target band was then cut out and the DNA fragment was purified. The DNA fragment was labeled with probe digoxinigen using DIG High Prime (manufactured by Boehringer-Mannheim) based on the procedure described in the manual of the kit.

After completely digesting the chromosomal DNA of *Empedobacter brevis* obtained in the step (3) of the present Example 28(3) by reacting at 37° C. for 16 hours with restriction enzyme HindIII, the resultant DNA was electrophoresed with on 0.8% agarose gel. The electrophoresed chromosomal DNA was blotted onto a positively charged Nylon membrane filter (manufactured by Roche Diagnostics) from the agarose gel after the electrophoresis, followed by treatments consisting of alkaline denaturation, neutralization and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed for 20 minutes at room temperature with 2×SSC containing 0.1% SDS. Moreover, the filter was additionally washed twice at 65° C. for 15 minutes with 0.1×SSC.

Detection of bands that hybridized with the probe was carried out using the DIG Nucleotide Detection Kit (manufactured by Boehringer-Mannheim) based on the procedure described in the manual of the kit. As a result, a roughly 4 kb band was able to be detected that hybridized with the probe.

Then, the chromosomal DNA prepared in the step (3) of the present Example 28(3) was completely digested with HindIII. A roughly 4 kb of DNA was separated by 0.8% agarose gel electrophoresis, followed by purification of the DNA using the Gene Clean II Kit (manufactured by Funakoshi) and dissolving the DNA in 10 μl of TE. 4 μl of this product was then mixed with pUC118 HindIII/BAP (manufactured by Takara Shuzo) and a ligation reaction was carried out using the DNA Ligation Kit Ver. 2 (manufactured by Takara Shuzo). 5 pd of the ligation reaction mixture and 100 μl of competent cells of *Escherichia coli* JM109 (manufactured by Toyobo) were mixed to transform the *Escherichia coli*. Thus obtained transformants were then applied to a suitable solid medium to produce a chromosomal DNA library.

To obtain the entire full-length of peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter (Nylon Membrane for Colony and Plaque Hybridization, (manufactured by Roche Diagnostics) followed by treatments consisting of alkali denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added, followed by hybridization at 50° C. for 16 hours. Subsequently, the filter was washed for 20 minutes at room temperature with 2×SSC containing 0.1% SDS. Moreover, the filter was additionally washed twice at 65° C. for 15 minutes with 0.1×SSC.

Detection of colonies that hybridized with the labeled probe was carried out using the DIG Nucleotide Detection Kit (manufactured by Boehringer-Mannheim) based on the explanation described in the manual of the kit. As a result, two colonies were verified to hybridize with the labeled probe.

(6) Base Sequence of Peptide-Forming Enzyme Gene Derived from *Empedobacter brevis*

Plasmids possessed by *Escherichia coli* JM109 were prepared from the aforementioned two colonies that were verified to hybridize with the labeled probe using the Wizard Plus Minipreps DNA Purification System (manufactured by Promega) to and the base sequence of a portion where hybridization with the probe occurred and nearby was determined. The sequencing reaction was carried out using the CEQ DTCS-Quick Start Kit (manufactured by Beckman-Coulter) based on the procedure described in the manual of the kit. In addition, electrophoresis was carried out using the CEQ 2000-XL (manufactured by Beckman-Coulter).

As a result, it was verified that an open reading frame that encodes a protein containing the internal amino acid sequences of the peptide-forming enzyme (SEQ ID NOs: 1 and 2) did exist. Thus, the open reading frame was confirmed to be a gene encoding the peptide-forming enzyme. The base sequence of the full-length of the peptide-forming enzyme genes along with the corresponding amino acid sequences is shown in SEQ ID NO: 5. As a result of analysis on the homology of the resulting open reading frame with the BLASTP program, homology was discovered between the two enzymes; it showed with a homology of 34% as at the amino acid sequence level exhibited with the α-amino acid ester hydrolase of *Acetobacter pasteurianus* (see Appl. Environ. Microbiol., 68(1), 211-218 (2002), and a homology of 26% at the amino acid sequence level exhibited with the glutaryl-7ACA acylase of *Brevibacillus laterosporum* (see J. Bacteriol., 173(24), 7848-7855 (1991).

Example 29

Expression of Peptide-Forming Enzyme Gene Derived from *Empedobacter brevis* in *Escherichia coli*

A target gene region on the promoter region of the trp operon on the chromosomal DNA of *Escherichia coli* W3110 was amplified by carrying out PCR using the oligonucleotides indicated in SEQ ID NOs: 7 and 8 as primers, and the resulting DNA fragments were ligated to a pGEM-Teasy vector (manufactured by Promega). *E. coli* JM109 was then transformed in this ligation solution, and those strains having the target plasmid in which the direction of the inserted trp promoter is inserted in the opposite to the orientation from of the lac promoter were selected from ampicillin-resistant strains. Next, a DNA fragment containing the trp promoter obtained by treating this plasmid with EcoO109I/EcoRI was ligated to an EcoO109I/EcoRI treatment product of pUC19 (manufactured by Takara). *Escherichia coli* JM109 was then transformed with this ligation solution and those strains having the target plasmid were selected from ampicillin-resistant strains. Next, a DNA fragment obtained by treating this plasmid with HindIII/PvuII was ligated with to a DNA fragment containing an rrnB terminator obtained by treating pKK223-3 (manufactured by Amersham Pharmacia) with HindIII/HincII. *E. coli* JM109 was then transformed with this ligation solution, strains having the target plasmid were selected from ampicillin-resistant strains, and the plasmid was designated as pTrpT.

The target gene was amplified by PCR using the chromosomal DNA of *Empedobacter brevis* strain FERM BP-8113 (Depositary institution: the independent administrative corporation, National Institute of Advanced Industrial Science and Technology, International Patent Organism Depositary, Address of depositary institution: Chuo No Chuo Dai-6, 1-1 Higashi 1-Chome, Tsukuba-shi, Ibaraki-ken, Japan, International deposit transfer date: Jul. 8, 2002) as a template and the oligonucleotides indicated in SEQ ID NO: 9 and 10 as primers. This DNA fragment was then treated with NdeI/PstI, and the resulting DNA fragment was ligated with the NdeI/PstI treatment product of pTrpT. *Escherichia coli* JM109 was then transformed with this ligation solution, those strains having the target plasmid were selected from ampicillin-resistant strains, and this plasmid was designated as pTrpT_Gtg2.

*Escherichia coli* JM109 having pTrpT_Gtg2 was pre-cultured at 30° C. for 24 hours in LB medium containing 100 mg/l of ampicillin. 1 ml of the resulting culture broth was inoculated into a 500 ml Sakaguchi flask containing 50 ml of a medium (D glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l, and ampicillin at 100 mg/l), followed by culturing at 25° C. for 24 hours. The culture broth had an L-alanyl-L-glutamine forming activity of 0.44 Upper 1 ml of culture broth and it was verified that the cloned gene was expressed by *E. coli*. Furthermore, no activity was detected for a transformant in which only pTrpT had been introduced as a control.

Prediction of Signal Sequence

When the amino acid sequence of SEQ ID NO: 6 described in the Sequence Listing was analyzed with the Signal P v 1.1 program (see Protein Engineering, Vol. 12, No. 1, pp. 3-9, 1999), it was predicted that amino acids numbers 1 to 22 function as a signal for secretion of peptide into the periplasm, while the mature protein was estimated to be downstream of amino acid number 23.

Verification of Secretion

*Escherichia coli* JM109, having pTrpT_Gtg2, was pre-cultured at 30° C. for 24 hours in LB medium containing 100 mg/l of ampicillin. 1 ml of the resulting culture broth was inoculated into a 500 ml Sakaguchi flask containing 50 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l, and ampicillin at 100 mg/l), followed by final culturing at 25° C. for 24 hours to obtain microbial cells.

The cultured microbial cells were fractionated into a periplasm fraction and a cytoplasm fraction after disruption of cells by an osmotic pressure shock method using a 20 grams/deciliter (g/dl) sucrose solution. The disrupted microbial cells immersed in the 20 g/dl sucrose solution were immersed in a 5 mM aqueous $MgSO_4$ solution. The centrifuged supernatant was named a periplasm fraction ("Pe"). In addition, the centrifuged sediment was re-suspended and subjected to ultrasonic disruption. The resultant was named a cytoplasm fraction ("Cy"). The activity of glucose 6-phosphate dehydrogenase, which is known to be present in the cytoplasm, was used as an indicator to verify that the cytoplasm had been separated. This measurement was carried out by adding a suitable amount of enzyme to a reaction solution at 30° C. containing 1 mM glucose 6-phosphate, 0.4 mM NADP, 10 mM $MgSO_4$, and 50 mM Tris-Cl (pH 8), followed by measurement of absorbance at 340 nm to measure production of NADPH.

Figure 4:
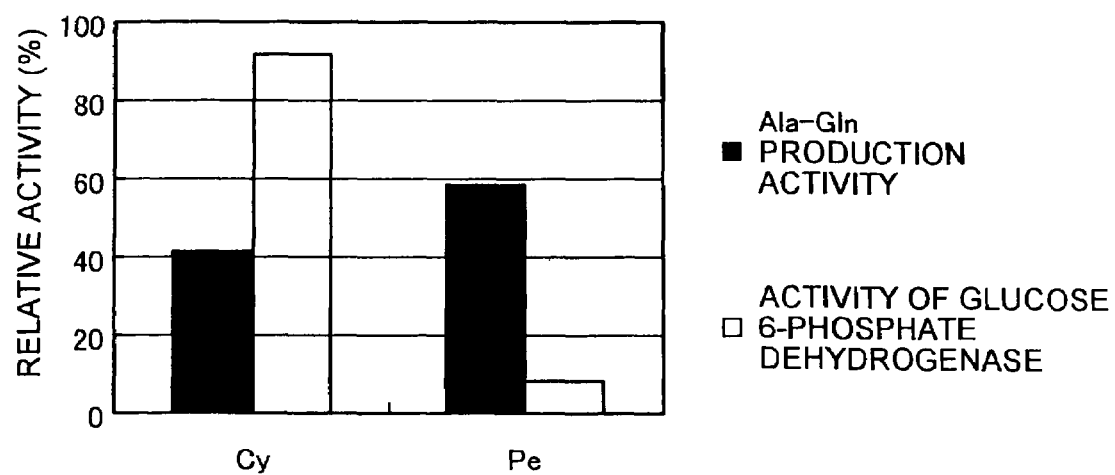
FIG. 4 is a bar graph illustrating the amount of enzyme present in a cytoplasm fraction (Cy) and a periplasm fraction (Pe).

FIG. 4 demonstrates that the amounts of enzymes of in the periplasm fraction and the cytoplasm fraction when the activity of a separately prepared cell-free extract was assigned a value of 100%. The glucose 6-phosphate dehydrogenase activity was not detected in the periplasm fraction. This indicates that the periplasm fraction did not mix in the cytoplasm fraction. About 60% of the Ala-Gln forming activity was recovered in the periplasm fraction, and it was verified that the Ala-Gln forming enzyme was secreted into the periplasm as predicted from the amino acid sequence using the Signal P v 1.1 program.

Example 30

Production of L-Alanyl-L-Glutamine Using Microbial Cells of *Sphingobacterium* sp A 50 ml medium (pH 7.0) containing 5 g of glucose, 5 g of ammonium sulfate, 1 g of monopotassium phosphate, 3 g of dipotassium phosphate, 0.5 g of magnesium sulfate, 10 g of yeast extract, and 10 g of peptone in 1 L was transferred to a 500 mL Sakaguchi flask and sterilized at 115° C. for 15 minutes for culturing *Sphingobacterium* sp. strain FERM BP-8124 (Depositary institution: the independent administrative corporation, National Institute of Advanced Industrial Science and Technology, International Patent Organism Depository, Address of depositary institution: Chuo Dai-6, 1-1 Higashi 1-Chome, Tsukuba-shi, Ibaraki-ken, Japan, International deposit date: Jul. 22, 2002). This was then inoculated with one loopful cells of *Sphingobacterium* sp. strain FERM BP-8124 (Depositary institution: National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) cultured at 30° C. for 24 hours in slant agar medium (agar: 20 g/L, pH 7.0) containing 5 g of glucose, 10 g of yeast extract, 10 g of peptone and 5 g of NaCl in 1 L, followed by shake culturing at 30° C. for 20 hours and 120 strokes/minute. 1 ml of this culture broth was then added to the aforementioned medium (50 ml/500 mL Sakaguchi flask) and cultured at 30° C. for 18 hours. After completion of the culture, the microbial cells were separated from the culture broth by centrifugation and suspended in 0.1 M borate buffer (pH 9.0) containing 10 mM EDTA at a concentration of 100 g/L as wet microbial cells. 0.1 mL of 100 mM borate buffer (pH 9.0) containing 10 mM EDTA, 200 mM L-alanine methyl ester hydrochloride and 400 mM L-glutamine was then added to 0.1 mL of this microbial cell suspension. The resulting 0.2 mL of mixture was allowed to react at 25° C. for 120 minutes. The concentration of L-alanyl-L-glutamine produced at this time was 62 mM.

Example 31

Purification of Enzyme from *Sphingobacterium* sp

The following procedure after centrifugation was carried out either on ice or at 4° C. *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultured in the same manner as Example 21, and the microbial cells were collected by centrifugation (10,000 rpm, 15 minutes). After washing 2 g of microbial cells with 20 mM Tris-HCl buffer (pH 7.6), they were suspended in 8 ml of the same buffer and subjected to ultrasonic disrupting treatment for 45 minutes at 195 W. This ultrasonically disrupted suspension was then centrifuged (10,000 rpm, 30 minutes) to remove the cell debris and obtain a supernatant. This supernatant was dialyzed overnight against 20 mM Tris-HCl buffer (pH 7.6) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 7.6), and the active fraction was collected from the non-adsorbed fraction. This active fraction was dialyzed overnight against 20 mM acetate buffer (pH 5.0), followed by removal of the insoluble fraction by centrifugation (10,000 rpm, 30 minutes) to obtain a dialyzed fraction in the form of the supernatant liquid. This dialyzed fraction was then applied to an SP-Sepharose HP column (manufactured by Amersham) pre-equilibrated with 20 mM acetate buffer (pH 5.0) to obtain the active fraction in which enzyme was eluted at a linear concentration gradient of the same buffer containing 0 to 1 M NaCl.

Example 32

Production of L-Alanyl-L-Glutamine Using Active Fraction

10 μl of the SP-Sepharose HP fraction (about 27 U/ml) purified in Example 31 was added to 90 μl of borate buffer (pH 9.0) containing 111 mM L-alanine methyl ester hydrochloride, 222 mM L-glutamine and 11 mM EDTA, and allowed to react at 25° C. for 120 minutes. As a result, 73 mM of L-alanyl-L-glutamine was produced in the section to which enzyme was added. On the other hand, there was scarcely any production of L-Ala-L-Glu observed in the lot to which enzyme was not added, and the amount produced was only about 0.07 mM after reacting for 120 minutes.

Example 33

Isolation of Peptide-Forming enzyme Gene Derived from *Sphingobacterium* sp

Although the following provides a description of the isolation of a peptide-forming enzyme gene, *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was used as the microbe. Gene isolation was carried out using *Escherichia coli* DH5α as the host, and pUC118 as the vector.

(1) Preparation of Microbe

*Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultured at 25° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 25° C.

(2) Preparation of Chromosomal DNA from Microbial Cells 50 ml of culture broth was centrifuged (12,000 rpm, 4° C., 15 minutes) to collect the microbial cells. A chromosomal DNA was then obtained from the microbial cells using the Qiagen Genomic-Tip System (Qiagen) therefor.

(3) Preparation of Probe DNA Fragment by PCR

A DNA fragment containing a portion of the peptide-forming enzyme gene derived from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was obtained by the PCR method using LA-Taq (manufactured by Takara Shuzo). A PCR reaction was then carried out on a chromosomal DNA obtained from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki 1-Chome, Japan, International deposit transfer date: Jul. 8, 2002) using primers having the base sequences of SEQ ID NOs: 3 and 4.

The PCR reaction was carried out for 30 cycles under the following conditions using the Takara PCR Thermal Cycler PERSONAL (manufactured by Takara Shuzo).

| | |
|---|---|
| 94° C. | 30 seconds |
| 52° C. | 1 minute |
| 72° C. | 1 minute |

After the reaction, 3 μl of reaction mixture was applied to 0.8% agarose electrophoresis. As a result, a DNA fragment of about 1.5 kb was confirmed to be amplified.

(4) Cloning of Peptide-Forming Enzyme Gene from Gene Library

In order to obtain the entire length of peptide-forming enzyme gene, Southern hybridization was carried out using the DNA fragment amplified in the aforementioned PCR procedure as a probe. The procedure for Southern hybridization is explained in Molecular Cloning, 2nd edition, Cold Spring Harbor Press (1989).

The approximately 1.5 kb DNA fragment amplified by the aforementioned PCR procedure was separated by 0.8% agarose electrophoresis. The target band was then cut out and the DNA fragment was purified. This DNA fragment was labeled with probe digoxinigen using DIG High Prime (manufactured by Boehringer-Mannheim) based on the procedure described in the manual of the kit.

After completely digesting the chromosomal DNA of *Sphingobacterium* sp. obtained in the step (2) of the present Example 33 by reacting at 37° C. for 16 hours with restriction enzyme SacI, it was electrophoresed with 0.8% agarose gel. The electrophoresed chromosomal DNA was blotted onto a positively charged Nylon membrane filter (manufactured by Roche Diagnostics) from the agarose gel following electrophoresis followed by treatment consisting of alkaline denaturation, neutralization and immobilization. Hybridization was carried out using EASY HYB (manufactured by Boehringer-Mannheim). After pre-hybridizing the filter at 37° C. for 1 hour, the probe labeled with digoxinigen prepared as described above was added and hybridization was carried out at 37° C. for 16 hours. Subsequently, the filter was washed twice at 60° C. with 1×SSC containing 0.1% SDS.

Detection of bands that hybridized with the probe was carried out using the DIG Nucleotide Detection Kit (manufactured by Boehringer-Mannheim) based on the procedure described in the manual of the kit. As a result, a roughly 3 kb band was able to be detected that hybridized with the probe.

The chromosomal DNA prepared in the step (2) of the present Example 33 was completely digested with Sac. Roughly 3 kb of DNA was separated by 0.8% agarose gel electrophoresis, followed by purification of the DNA using the Gene Clean II Kit (manufactured by Funakoshi) and dissolving in 10 µl of TE. After allowing 4 µl of this product to react with SacI at 37° C. for 16 hours to completely digest, it was mixed with pUC118 treated with alkaline phosphatase (*E. coli* C75) at 37° C. for 30 minutes and at 50° C. for 30 minutes, and a ligation reaction was carried out using the DNA Ligation Kit Ver. 2 (manufactured by Takara Shuzo). 5 µl of this ligation reaction liquid and 100 µl of competent cells of *Escherichia coli* DH5α (manufactured by Takara Shuzo) were mixed to transform the *Escherichia coli*. Thus obtained transformants were then applied to a suitable solid medium to produce a chromosomal DNA library.

In order to obtain the entire length of peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter—Nylon Membrane for Colony and Plaque Hybridization (manufactured by Roche Diagnostics), followed by treatment consisting of alkaline denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 1% SDS.

Detection of colonies that hybridized with the labeled probe was carried out using the DIG Nucleotide Detection Kit (manufactured by Boehringer-Mannheim) based on the explanation described in the manual of the kit. As a result, six strains of colonies were confirmed to hybridize with the labeled probe.

(5) Base Sequence of Peptide-Forming Enzyme Gene Derived from *Sphingobacterium* sp.

Plasmids possessed by *Escherichia coli* DH5α were prepared from the aforementioned six strains of microbial cells which were confirmed to hybridize with the labeled probe using the Wizard Plus Minipreps DNA Purification System (manufactured by Promega) to determine the nearby base sequences that hybridized with the probe. The sequencing reaction was carried out using the CEQ DTCS-Quick Start Kit (manufactured by Beckman-Coulter) based on the procedure described in the manual of the kit. In addition, electrophoresis was carried out using the CEQ 2000-XL (manufactured by Beckman-Coulter).

As a result, an open reading frame that encodes peptide-forming enzyme was found to exist. The base sequence of the full-length peptide-forming enzyme gene derived from *Sphingobacterium* sp. along with the corresponding amino acid sequence is shown in SEQ ID NO: 11. The peptide-forming enzyme derived from *Sphingobacterium* sp. exhibited homology of 63.5% at the amino acid sequence level with the peptide-forming enzyme derived from the aforementioned *Empedobacter brevis* (as determined using the BLASTP program).

Example 34

Expression of Peptide-Forming Enzyme Gene Derived from *Sphingobacterium* sp. in *Escherichia coli*

The target gene was amplified by carrying out PCR using a chromosomal DNA of *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) as template and the oligonucleotides shown in SEQ ID NOs: 13 and 14 as primers. This DNA fragment was treated with NdeI/XbaI, and the resulting DNA fragment and NdeI/XbaI treatment product of pTrpT were ligated. *Escherichia coli* JM109 was then transformed with this ligation solution, strains having the target plasmid were selected from ampicillin-resistant strains, and the plasmid was designated as pTrpT_Sm_aet.

*Escherichia coli* JM109 having pTrpT_Sm_aet was cultured at 25° C. for 20 hours by inoculating one loopful cells of the strain into an ordinary test tube containing 3 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l). Cloned gene having L-alanyl-L-glutamine production activity of 2.1 U per 1 ml of culture liquid was confirmed to be expressed by *E. coli*. Furthermore, activity was not detected for a transformant containing only pTrpT used as a control.

Prediction of Signal Sequence

When the amino acid sequence of SEQ ID NO: 12 described in the Sequence Listing was analyzed with the Signal P v1.1 program (see Protein Engineering, Vol. 12, No. 1, pp. 3-9, 1999), it was predicted that amino acids numbers 1 to 20 function as a signal for secretion of peptide into the periplasm, while the mature protein was estimated to be downstream of amino acid number 21.

Confirmation of Signal Sequence

*Escherichia coli* JM109, having pTrpT_Sm_aet, was cultured at 25° C. for 20 hours by inoculating one loopful cells of the strain into an ordinary test tube containing 50 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l).

The following procedure after centrifugation was carried out either on ice or at 4° C. Following completion of culturing, the microbial cells were separated from the culture broth by centrifugation, and after washing with 100 mM phosphate buffer (pH 7), were suspended in the same buffer. The microbial cells were then subjected to ultrasonic disruption for 20 minutes at 195 W, the ultrasonically disrupted liquid was centrifuged (12,000 rpm, 30 minutes) to remove the cell debris and obtain a soluble fraction. The resulting soluble fraction was applied to a CHT-II column (manufactured by Biorad) pre-equilibrated with 100 mM phosphate buffer (pH 7), and enzyme was eluted at a linear concentration gradient by 500 mM phosphate buffer. A solution obtained by mixing the active fraction with a 5-fold volume of 2 M ammonium sulfate and 100 mM phosphate buffer was applied to a Resource-PHE column (Amersham) pre-equilibrated with 2 M ammonium sulfate and 100 mM phosphate buffer, and enzyme was eluted at a linear concentration gradient by 2 to 0 M ammonium sulfate to obtain an active fraction solution. As a result of these procedures, the peptide-forming enzyme was confirmed to be uniformly purified in terms of electrophoresis.

When the amino acid sequence of the aforementioned peptide-forming enzyme was determined by Edman's decomposition method, the amino acid sequence of SEQ ID NO: 15 was obtained, and the mature protein was confirmed to be downstream from amino acid number 21 as was predicted by the SignalP v 1.1 program.

Example 35

Isolation of Peptide-Forming Enzyme Gene Derived from *Pedobacter heparinus* IFO 12017

Hereinafter, the isolation of a peptide-forming enzyme gene will be described. The microbe used is *Pedobacter heparinus* strain IFO 12017 (Depositary institution: Institute of Fermentation, Address of depositary institution: 2-17-85 Jusanbon-cho, Yodogawa-ku, Osaka-shi, Japan). *Escherichia coli* JM-109 was used as a host while pUC118 was used as a vector in isolating the gene.

(1) Preparation of Microbe

*Pedobacter heparinus* strain IFO-12017 (Depositary institution: Institute of Fermentation, Address of depositary institution: 2-17-85 Jusanbon-cho, Yodogawa-ku, Osaka-shi, Japan) was cultured at 25° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells were inoculated into a 500 ml Sakaguchi flask containing 50 ml of CM2G liquid medium (the aforementioned medium excluding agar) followed by shake culturing at 25° C.

(2) Preparation of Chromosomal DNA from Microbial Cells 50 ml of culture broth was centrifuged (12,000 rpm, 4° C., 15 minutes) to collect the microbial cells. A chromosomal DNA was then obtained from the microbial cells using the Qiagen Genomic-Tip System (Qiagen) based on the procedure described in the manual therefor.

(3) Preparation of Probe DNA Fragment by PCR

A DNA fragment containing a portion of the peptide-forming enzyme gene derived from *Pedobacter heparinus* strain IFO-12017 (Depositary institution: Institute of Fermentation, Address of depositary institution: 2-17-85 Jusanbon-cho, Yodogawa-ku, Osaka-shi, Japan) was obtained by the PCR method using LA-Taq (manufactured by Takara Shuzo). A PCR reaction was then carried out on a chromosomal DNA obtained from *Pedobacter heparinus* strain IFO-12017 (Depositary institution: Institute of Fermentation, Address of depositary institution: 2-17-85 Jusanbon-cho, Yodogawa-ku, Osaka-shi, Japan) using primers having the base sequences of SEQ ID NOs: 15 and 16. A DNA fragment of about 1 kb amplified by PCR was separated by 0.8% agarose electrophoresis. The target band was then cut out and thus obtained DNA fragment was purified. This DNA fragment was labeled with probe digoxinigen using DIG High Prime based on the procedure described in the manual (manufactured by Boehringer-Mannheim).

(4) Cloning of Peptide-Forming Enzyme Gene from Gene Library

To obtain the full-length peptide-forming enzyme gene, Southern hybridization was carried out using the DNA fragment amplified in the aforementioned PCR procedure as a probe. The procedure for Southern hybridization is explained in Molecular Cloning, 2nd edition, Cold Spring Harbor Press (1989).

After completely digesting the chromosomal DNA of *Pedobacter heparinus* strain IFO-12017 (Depositary institution: Institute of Fermentation, Address of depositary institution: 2-17-85 Jusanbon-cho, Yodogawa-ku, Osaka-shi, Japan) by reacting at 37° C. for 16 hours with restriction enzyme HindIII, it was electrophoresed with 0.8% agarose gel. The electrophoresed chromosomal DNA was blotted onto a positively charged Nylon membrane filter (manufactured by Roche Diagnostics) from the agarose gel after the electrophoresis, followed by treatment consisting of alkali denaturation, neutralization, and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed twice at 60° C. with 1×SSC containing 0.1% SDS.

Detection of bands that hybridized with the probe was carried out based on the procedure described in the manual using the DIG Nucleotide Detection Kit (manufactured by Boehringer-Mannheim). As a result, a roughly 5 kb band was able to be detected that hybridized with the probe.

The chromosomal DNA of *Pedobacter heparinus* strain IFO-12017 (Depositary institution: Institute of Fermentation, Address of depositary institution: 2-17-85 Jusanbon-cho, Yodogawa-ku, Osaka-shi, Japan) were completely digested with HindIII. Roughly 5 kb of DNA were separated by 0.8% agarose gel electrophoresis followed by purification of the DNA using the Gene Clean II Kit (manufactured by Funakoshi) and dissolving in 10 μl of TE. 4 μl of this product was then mixed with pUC118 HindIII/BAP (manufactured by Takara Shuzo) and a ligation reaction was carried out using the DNA Ligation Kit Ver. 2 (manufactured by Takara Shuzo). 5 μl of this ligation reaction liquid and 100 μl of competent cells of *Escherichia coli* JM109 (manufactured by Takara Shuzo) were mixed to transform the *Escherichia coli*. The obtained transformants were then applied to a suitable solid medium to produce a chromosomal DNA library.

In order to obtain the full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization, (manufactured by Roche Diagnostics), followed by treatment consisting of alkali denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 1% SDS.

Detection of colonies that hybridized with the labeled probe was carried out based on the explanation described in the manual using the DIG Nucleotide Detection Kit (manufactured by Boehringer-Mannheim). As a result, 1 strain of colonies was confirmed to hybridize with the labeled probe.

(5) Base Sequence of Peptide-Forming Enzyme Gene Derived from *Pedobacter heparinus* Strain IFO-12017

Plasmids retained by *Escherichia coli* JM109 were prepared from the aforementioned strain of microbial cells which were confirmed to hybridize with the labeled probe, and the nearby base sequence that hybridized with the probe was determined. The sequencing reaction was carried out using the CEQ DTCS-Quick Start Kit (manufactured by Beckman-Coulter) based on the procedure described in the manual. In addition, electrophoresis was carried out using the CEQ 2000-XL (Beckman-Coulter).

As a result, an open reading frame that encodes peptide-forming enzyme was found to exist. The base sequence of the full-length peptide-forming enzyme gene derived from *Pedobacter heparinus* strain IFO-12017 (Depositary institution: Institute of Fermentation, Address of depositary institution: 2-17-85 Jusanbon-cho, Yodogawa-ku, Osaka-shi, Japan), along with the corresponding amino acid sequence, is shown in SEQ ID NO: 17 of the Sequence Listing.

Example 36

Expression of Peptide-Forming Enzyme Gene Derived from *Pedobacter heparinus* strain IFO-12017 in *E. coli*

The target gene was amplified by carrying out PCR using a chromosomal DNA of *Pedobacter heparinus* strain IFO-12017 (Depositary institution: Institute of Fermentation, Osaka, Address of depositary institution: 2-17-85 Jusanbon-cho, Yodogawa-ku, Osaka-shi, Japan) as template and the oligonucleotides shown in SEQ ID NOs: 19 and 20 as primers. This DNA fragment was treated with NdeI/HindIII, and the resulting DNA fragment and NdeI/HindIII treatment product of pTrpT were ligated. *Escherichia coli* JM109 was then transformed with this ligation solution, strains having the target plasmid were selected from ampicillin-resistant strains, and the plasmid was designated as pTrpT_Ph_aet.

*Escherichia coli* JM109 having pTrpT_Ph_aet was cultured at 25° C. for 20 hours by inoculating one loopful cells of the strain into an ordinary test tube containing 3 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l). A cloned gene having L-alanyl-L-glutamine production activity of 0.3 Upper ml of culture liquid was confirmed to be expressed in *E. coli*. Furthermore, no activity was detected for a transformant containing only pTrpT used as a control.

Example 37

Isolation of Peptide-Forming Enzyme Gene Derived from *Taxeobacter gelupurpurascens* Strain DSMZ 11116

Hereinafter, the isolation of peptide-forming enzyme gene will be described. The microbe used is *Taxeobacter gelupurpurascens* strain DSMZ 11116 (Depositary institution: Deutche Sammiung von Mikroorganismen und Zellkulturen GmbH (German Collection of Microbes and Cell Cultures), Address of depositary institution: Mascheroder Weg 1b, 38124 Braunschweig, Germany) was used for the microbe. *Escherichia coli* JM-109 was used as a host while pUC118 was used as a vector in isolating the gene.

(1) Preparation of Microbe

*Taxeobacter gelupurpurascens* strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany) was cultured at 25° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells were inoculated into a 500 ml Sakaguchi flask containing 50 ml of CM2G liquid medium (the aforementioned medium excluding agar) followed by shake culturing at 25° C.

(2) Preparation of Chromosomal DNA from Microbial Cells 50 ml of culture liquid were centrifuged (12,000 rpm, 4° C., 15 minutes) to collect the microbial cells. A chromosomal DNA was then obtained from the microbial cells using the Qiagen Genomic-Tip System (Qiagen) based on the procedure described in the manual therefor.

(3) Preparation of Probe DNA Fragment by PCR

A DNA fragment containing a portion of the peptide-forming enzyme gene derived from *Taxeobacter gelupurpurascens* strain DSMZ 11116 (Depositary institution: Deutche Sammiung von Mikroorganismen und Zellkulturen GmbH (German Collection of Microbes and Cell Cultures), Address of depositary institution: Mascheroder Weg 1b, 38124 Braunschweig, Germany) was obtained by the PCR method using LA-Taq (manufactured by Takara Shuzo). A PCR reaction was then carried out on a chromosomal DNA obtained from *Taxeobacter gelupurpurascens* strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany) using primers having the base sequences of SEQ ID NOs: 21 and 16. A DNA fragment of about 1 kb amplified by PCR was separated by 0.8% agarose electrophoresis. The target band was then cut out and the DNA fragment was purified. This DNA fragment was labeled with probe digoxinigen using DIG High Prime (manufactured by Boehringer-Mannheim) based on the procedure described in the manual.

(4) Cloning of Peptide-Forming Enzyme Gene from Gene Library

To obtain the full-length peptide-forming enzyme gene, Southern hybridization was carried out using the DNA fragment amplified in the aforementioned PCR procedure as a probe. The procedure for Southern hybridization is explained in Molecular Cloning, 2nd edition, Cold Spring Harbor Press (1989).

After completely digesting the chromosomal DNA of *Taxeobacter gelupurpurascens* strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany) by reacting at 37° C. for 16 hours with restriction enzyme PstI, it was electrophoresed with 0.8% agarose gel. The electrophoresed chromosomal DNA was blotted onto a positively charged Nylon membrane filter (manufactured by Roche Diagnostics) from the agarose gel following electrophoresis followed by treatment consisting of alkali denaturation, neutralization and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed twice at 60° C. with 1×SSC containing 0.1% SDS.

Detection of bands that hybridized with the probe was carried out based on the procedure described in the manual using the DIG Nucleotide Detection Kit (manufactured by Boehringer-Mannheim). As a result, a roughly 5 kb band was able to be detected that hybridized with the probe.

The chromosomal DNA of *Taxeobacter gelupurpurascens* strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany) were completely digested with HindIII. Roughly 5 kb of DNA were separated by 0.8% agarose gel electrophoresis followed by purification of the DNA using the Gene Clean II Kit (manufactured by Funakoshi) and dissolving in 10 µl of TE. 4 µL of this product were then mixed with pUC118 PstI/BAP (manufactured by Takara Shuzo) and a ligation reaction was carried out using the DNA Ligation Kit Ver. 2 (manufactured by Takara Shuzo). 5 µl of this ligation reaction liquid and 100 µl of competent cells of *Escherichia coli* JM109 (manufactured by Takara Shuzo) were mixed to transform the *Escherichia coli*. Thus obtained transformants were then applied to a suitable solid medium to produce a chromosomal DNA library.

In order to obtain the entire length of peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization, (manufactured by Roche Diagnostics) followed by treatment consisting of alkaline denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 0.1% SDS.

Detection of colonies that hybridized with the labeled probe was carried out based on the manual using the DIG Nucleotide Detection Kit (manufactured by Boehringer-Mannheim). As a result, 1 strain of colonies was confirmed to hybridize with the labeled probe.

(5) Base Sequence of Peptide-Forming Enzyme Gene Derived from *Taxeobacter gelupurpurascens* Strain DSMZ 11116

Plasmids retained by *Escherichia coli* JM109 were prepared from the aforementioned strain of microbial cells which were confirmed to hybridize with the labeled probe, and the nearby base sequence that hybridized with the probe was determined. The sequencing reaction was carried out using the CEQ DTCS-Quick Start Kit (manufactured by Beckman-Coulter) based on the procedure described in the manual. In addition, electrophoresis was carried out using the CEQ 2000-XL (manufactured by Beckman-Coulter).

As a result, an open reading frame that encodes peptide-forming enzyme was found to exist. The base sequence of the entire length of the peptide-forming enzyme gene derived from *Taxeobacter gelupurpurascens* strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany), along with the corresponding amino acid sequence, are shown in SEQ ID NO: 22 of the Sequence Listing.

Example 38

Isolation of Peptide-Forming Enzyme Gene Derived from *Cyclobacterium marinum* Strain ATCC 25205

Hereinafter, the isolation of peptide-forming enzyme gene will be described. The microbe used is *Cyclobacterium marinum* strain ATCC 25205 (Depositary institution: American Type Culture Collection, Address of depositary institution: P.O. Box 1549, Manassas, Va. 20110, the United States of America). *Escherichia coli* JM-109 was used as a host while pUC118 was used for the vector in isolating the gene.

(1) Preparation of Microbial Cells

*Cyclobacterium marinum* strain ATCC 25205 (Depositary institution: American Type Culture Collection, Address of depositary institution: P.O. Box 1549, Manassas, Va. 20110, the United States of America) was cultured at 25° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells was inoculated into a 500 ml Sakaguchi flask containing 50 ml of CM2G liquid medium (the aforementioned medium excluding agar), followed by shake culturing at 25° C.

(2) Preparation of Chromosomal DNA from Microbial Cells 50 ml of culture broth were centrifuged (12,000 rpm, 4° C., 15 minutes) to collect the microbial cells. A chromosomal DNA was then obtained from the microbial cells based on the procedure described in the manual using the Qiagen Genomic-Tip System (Qiagen).

(3) Preparation of Probe DNA Fragment by PCR

A DNA fragment containing a portion of the peptide-forming enzyme gene derived from *Cyclobacterium marinum* strain ATCC 25205 (Depositary institution: American Type Culture Collection, Address of depositary institution: P.O.

Box 1549, Manassas, Va. 20110, the United States of America) was obtained by the PCR method using LA-Taq (manufactured by Takara Shuzo). A PCR reaction was then carried out on a chromosomal DNA obtained from *Cyclobacterium marinum* strain ATCC 25205 (Depositary institution: American Type Culture Collection, Address of depositary institution: P.O. Box 1549, Manassas, Va. 20110, the United States of America) using primers having the base sequences of SEQ ID NOs: 15 and 16. A DNA fragment of about 1 kb amplified by PCR was separated by 0.8% agarose electrophoresis. The target band was then cut out and the DNA fragment was purified. This DNA fragment was labeled with probe digoxinigen based on the procedure described in the manual using DIG High Prime (manufactured by Boehringer-Mannheim).

(4) Cloning of Peptide-Forming Enzyme Gene from Gene Library

In order to obtain the full-length peptide-forming enzyme gene, Southern hybridization was first carried out using the DNA fragment amplified in the aforementioned PCR procedure as a probe. The procedure for Southern hybridization is explained in Molecular Cloning, 2nd edition, Cold Spring Harbor Press (1989).

After completely digesting the chromosomal DNA of *Cyclobacterium marinum* strain ATCC 25205 (Depositary institution: American Type Culture Collection, Address of depositary institution: P.O. Box 1549, Manassas, Va. 20110, the United States of America) by reacting at 37° C. for 16 hours with restriction enzyme HincII, each was electrophoresed with 0.8% agarose gel. The electrophoresed chromosomal DNA was blotted onto a positively charged Nylon membrane filter (manufactured by Roche Diagnostics) from the agarose gel following electrophoresis followed by treatment consisting of alkali denaturation, neutralization and immobilization. Hybridization was carried out using EASY HYB (manufactured Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed twice at 60° C. with 1×SSC containing 0.1% SDS.

Detection of bands that hybridized with the probe was carried out based on the procedure described in the manual using the DIG Nucleotide Detection Kit (manufactured by Boehringer-Mannheim). As a result, a roughly 7 k band was able to be detected that hybridized with the probe in the PstI digestion product, while a 2 k band was able to be detected that hybridized with the probe in the HincII digestion product.

The chromosomal DNA of *Cyclobacterium marinum* strain ATCC 25205 (Depositary institution: American Type Culture Collection, Address of depositary institution: P.O. Box 1549, Manassas, Va. 20110, the United States of America) were completely digested with PstI or HincII. Roughly 7 kb or 2 kb of DNA were respectively separated by 0.8% agarose gel electrophoresis, followed by purification of the DNA using the Gene Clean II Kit (Funakoshi) and dissolving in 10 µl of TE. 4 µl of this product were then mixed with pUC118 PstI/BAP (manufactured by Takara Shuzo) or pUC118 HincII/BAP (manufactured by Takara Shuzo) and a ligation reaction was carried out using the DNA Ligation Kit Ver. 2 (manufactured by Takara Shuzo). 5 µl of this ligation reaction liquid and 100 µl of competent cells of *Escherichia coli* JM109 (manufactured by Takara Shuzo) were respectively mixed to transform the *Escherichia coli*. Thus obtained transformants were then applied to a suitable solid medium to produce a chromosomal DNA library.

To obtain the full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization, (manufactured by Roche Diagnostics), followed by treatment consisting of alkali denaturation, neutralization, and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 0.1% SDS.

Detection of colonies that hybridized with the labeled probe was carried out based on the manual using the DIG Nucleotide Detection Kit (manufactured by Boehringer-Mannheim). As a result, 1 strain of colonies each was confirmed to hybridize with the labeled probe.

(5) Base Sequence of Peptide-Forming Enzyme Gene Derived from *Cyclobacterium marinum* Strain ATCC 25205

Plasmids retained by *Escherichia coli* JM109 were prepared from each of the aforementioned strains of microbial cells which were confirmed to hybridize with the labeled probe, and the nearby base sequence that hybridized with the probe was determined. The sequencing reaction was carried out using the CEQ DTCS-Quick Start Kit (manufactured by Beckman-Coulter) based on the procedure described in the manual of the kit. In addition, electrophoresis was carried out using the CEQ 2000-XL (manufactured by Beckman-Coulter).

As a result, an open reading frame that encodes peptide-forming enzyme was found to exist. The base sequence of the full-length peptide-forming enzyme gene derived from *Cyclobacterium marinum* strain ATCC 25205 (Depositary institution: American Type Culture Collection, Address of depositary institution: P.O. Box 1549, Manassas, Va. 20110, the United States of America), along with the corresponding amino acid sequence, is shown in SEQ ID NO: 24 of the Sequence Listing.

Example 39

Isolation of Peptide-Forming Enzyme Gene Derived from *Psycloserpens burtonensis* Strain ATCC 700359

Hereinafter, the isolation of a peptide-forming enzyme gene will be explained. The microbe used is *Psycloserpens burtonensis* strain ATCC 700359 (Depositary institution: American Type Culture Collection, Address of depositary institution: P.O. Box 1549, Manassas, Va. 20110, the United States of America). *Escherichia coli* JM-109 was used for the host while pUC118 was used for the vector in isolating the gene.

(1) Preparation of Microbe

*Psycloserpens burtonensis* strain ATCC 700359 (Depositary institution: American Type Culture Collection, Address of depositary institution: P.O. Box 1549, Manassas, Va. 20110, the United States of America) was cultured at 10° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 10° C.

(2) Preparation of Chromosomal DNA from Microbial Cells 50 ml of culture liquid were centrifuged (12,000 rpm, 4° C., 15 minutes) to collect the microbial cells. A chromosomal DNA was then obtained from the microbial cells using the Qiagen Genomic-Tip System (Qiagen) based on the procedure described in the manual therefor.

(3) Preparation of Probe DNA Fragment by PCR

A DNA fragment containing a portion of the peptide-forming enzyme gene derived from *Psycloserpens burtonensis* strain ATCC 700359 (Depositary institution: American Type Culture Collection, Address of depositary institution: P.O. Box 1549, Manassas, Va. 20110, the United States of America) was obtained by the PCR method using LA-Taq (manufactured by Takara Shuzo). A PCR reaction was then carried out on a chromosomal DNA obtained from *Psycloserpens burtonensis* strain ATCC 700359 (Depositary institution: American Type Culture Collection, Address of depositary institution: P.O. Box 1549, Manassas, Va. 20110, the United States of America) using primers having the base sequences of SEQ ID NOs: 15 and 16. A DNA fragment of about 1 kb amplified by PCR was separated by 0.8% agarose electrophoresis. The target band was then cut out and the DNA fragment was purified. This DNA fragment was labeled with probe digoxinigen based on the procedure described in the manual using DIG High Prime (manufactured by Boehringer-Mannheim).

(4) Cloning of Peptide-Forming Enzyme Gene from Gene Library

In order to obtain the entire length of peptide-forming enzyme gene, Southern hybridization was carried out using the DNA fragment amplified in the aforementioned PCR procedure as a probe. The procedure for Southern hybridization is explained in Molecular Cloning, 2nd edition, Cold Spring Harbor Press (1989).

After completely digesting the chromosomal DNA of *Psycloserpens burtonensis* strain ATCC 700359 (Depositary institution: American Type Culture Collection, Address of depositary institution: P.O. Box 1549, Manassas, Va. 20110, the United States of America) by reacting at 37° C. for 16 hours with restriction enzyme EcoRI, it was electrophoresed with 0.8% agarose gel. The electrophoresed chromosomal DNA was blotted onto a positively charged Nylon membrane filter (manufactured by Roche Diagnostics) from the agarose gel following electrophoresis followed by treatment consisting of alkaline denaturation, neutralization and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed twice at 60° C. with 1×SSC containing 0.1% SDS.

Detection of bands that hybridized with the probe was carried out using the DIG Nucleotide Detection Kit (manufactured by Boehringer-Mannheim) based on the procedure described in the manual of the kit. As a result, a roughly 7 kb band was able to be detected that hybridized with the probe.

The chromosomal DNA of *Psycloserpens burtonensis* strain ATCC 700359 (Depositary institution: American Type Culture Collection, Address of depositary institution: P.O. Box 1549, Manassas, Va. 20110, the United States of America) were completely digested with EcoRI. Roughly 7 kb of DNA were separated by 0.8% agarose gel electrophoresis followed by purification of the DNA using the Gene Clean II Kit (manufactured by Funakoshi) and dissolving in 10 μl of TE. 4 μl of this product were then mixed with pUC118 EcoRI/BAP (manufactured by Takara Shuzo) and a ligation reaction was carried out using the DNA Ligation Kit Ver. 2 (manufactured by Takara Shuzo). 5 μl of this ligation reaction liquid and 100 μl of competent cells of *Escherichia coli* JM109 (manufactured by Takara Shuzo) were mixed to transform the *Escherichia coli*. Thus obtained transformants were then applied to a suitable solid medium to produce a chromosomal DNA library.

To obtain the full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization, (manufactured by Roche Diagnostics), followed by treatment consisting of alkali denaturation, neutralization, and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 0.1% SDS.

Detection of colonies that hybridized with the labeled probe was carried out based on the manual using the DIG Nucleotide Detection Kit (manufactured by Boehringer-Mannheim). As a result, 1 strain of colonies was confirmed to hybridize with the labeled probe.

(5) Base Sequence of Peptide-Forming Enzyme Gene Derived from *Psycloserpens burtonensis* Strain ATCC 700359

Plasmids retained by *Escherichia coli* JM109 were prepared from the aforementioned strain of microbial cells which were confirmed to hybridize with the labeled probe, and the nearby base sequence that hybridized with the probe was determined. The sequencing reaction was carried out using the CEQ DTCS-Quick Start Kit (manufactured by Beckman-Coulter) based on the procedure described in the manual. In addition, electrophoresis was carried out using the CEQ 2000-XL (manufactured by Beckman-Coulter).

As a result, an open reading frame that encodes peptide-forming enzyme was found to exist. The base sequence of the full-length peptide-forming enzyme gene derived from *Psycloserpens burtonensis* strain ATCC 700359 (Depositary institution: American Type Culture Collection, Address of depositary institution: P.O. Box 1549, Manassas, Va. 20110, the United States of America), along with the corresponding amino acid sequence, are shown in SEQ ID NO: 26 of the Sequence Listing.

INDUSTRIAL APPLICABILITY

According to the present invention, a novel enzyme is provided that can produce a peptide easily, at high yield and inexpensively by reducing complex synthetic methods such as introduction and elimination of protecting groups. The use of the enzyme of the present invention enables efficient industrial production of a peptide.

Sequence Listing

SEQ ID NO: 3: Synthetic primer 1
SEQ ID NO: 4: Synthetic primer 2
SEQ ID NO: 5: Gene encoding a peptide-forming enzyme
SEQ ID NO: 7: Synthetic primer for preparing pTrpT
SEQ ID NO: 8: Synthetic primer for preparing pTrpT
SEQ ID NO: 9: Synthetic primer for preparing pTrpT_Gtg2
SEQ ID NO: 10: Synthetic primer for preparing pTrpT_Gtg2
SEQ ID NO: 11: Gene encoding peptide-forming enzyme
SEQ ID NO: 13: Synthetic primer for preparing pTrpT_Sm_aet
SEQ ID NO: 14: Synthetic primer for preparing pTrpT_Sm_aet
SEQ ID NO: 15: Mix primer 1 for Aet
SEQ ID NO: 16: Mix primer 2 for Aet
SEQ ID NO: 19: Primer 1 for constructing aet expression vectors derived from *Pedobacter*.
SEQ ID NO: 20: Primer 2 for constructing aet expression vectors derived from *Pedobacter*.
SEQ ID NO: 21: Mix primer 3 for Aet

The invention claimed is:

1. An isolated enzyme having peptide-forming activity, said enzyme consisting of a sequence selected from the group consisting of (C), (D), (O), (P), (C2), and (D2):

(C) an amino acid sequence consisting of amino acid residue numbers 21 to 619 of SEQ ID NO:12, (D) an amino acid sequence including substitution, deletion, insertion, and/or addition of one to 30 amino acid residues of the amino acid sequence of amino acid residue numbers 21 to 619 of SEQ ID NO:12, and has at least 50% of the peptide-forming activity of a protein corresponding to unmutated amino acid residue numbers 21 to 619 of SEQ ID NO:12 at 50° C. and a pH of 8, (O) an amino acid sequence consisting of SEQ ID NO:12, (P) an amino acid sequence including substitution, deletion, insertion, and/or addition of one to 30 amino acid residues of the amino acid sequence of SEQ ID NO:12, and has at least 50% of the peptide-forming activity of a protein corresponding to unmutated SEQ ID NO:12 at 50° C. and a pH of 8, (C2) an amino acid sequence encoded by a polynucleotide consisting of nucleotide numbers 121 to 1917 in SEQ ID NO: 11, and (D2) an amino acid sequence encoded by a polynucleotide that hybridizes with a polynucleotide comprising a nucleotide sequence complementary to the nucleotide sequence of nucleotide numbers 121 to 1917 in SEQ ID NO: 11 under stringent conditions, wherein said stringent conditions are 0.1×SSC and 0.1% SDS at 60° C., wherein said has at least 50% of the peptide-forming activity of a protein corresponding to unmutated SEQ ID NO:12 at 50° C. and a pH of 8.

2. The enzyme of claim 1, wherein said enzyme has an amino acid sequence consisting of amino acid residue numbers 21 to 619 of SEQ ID NO:12.

3. The enzyme of claim 1, wherein said enzyme has an amino acid sequence including substitution, deletion, insertion, and/or addition of one to 30 amino acid residues of the amino acid sequence of amino acid residue numbers 21 to 619 of SEQ ID NO:12, and has at least 50% of the peptide-forming activity of a protein corresponding to unmutated amino acid residue numbers 21 to 619 of SEQ ID NO:12 at 50° C. and a pH of 8.

4. The enzyme of claim 3, wherein the number of substitution, deletion, insertion, and/or addition is 1 to 10 amino acid residues.

5. The enzyme of claim 1, wherein said enzyme has an amino acid sequence consisting of SEQ ID NO:12.

6. The enzyme of claim 1, wherein said enzyme has an amino acid sequence including substitution, deletion, insertion, and/or addition of one to 30 amino acid residues of the amino acid sequence of SEQ ID NO:12, and has at least 50% of the peptide-forming activity of a protein corresponding to unmutated SEQ ID NO:12 at 50° C. and a pH of 8.

7. The enzyme of claim 6, wherein the number of substitution, deletion, insertion, and/or addition is 1 to 10 amino acid residues.

8. The enzyme of claim 1, wherein said enzyme has an amino acid sequence encoded by a polynucleotide consisting of nucleotide numbers 121 to 1917 in SEQ ID NO: 11.

9. The enzyme of claim 1, wherein said enzyme has an amino acid sequence encoded by a polynucleotide that hybridizes with a polynucleotide comprising a nucleotide sequence complementary to the nucleotide sequence of nucleotide numbers 121 to 1917 in SEQ ID NO: 11 under stringent conditions, wherein said stringent conditions are 0.1×SSC and 0.1% SDS at 60° C., wherein said has at least 50% of the peptide-forming activity of a protein corresponding to unmutated SEQ ID NO:12 at 50° C. and a pH of 8.

10. A method for producing a dipeptide comprising contacting a carboxy component and an amine component with the enzyme of claim 1.

11. The method of claim 10, wherein said carboxy component is an amino acid ester or an amino acid amide.

12. The method of claim 10, wherein said carboxy component is selected from the group consisting of an L-amino acid ester, a D-amino acid ester, an L-amino acid amide, and a D-amino acid amide.

13. The method of claim 10, wherein said amine component is selected from the group consisting of an amino acid and a C-protected amino acid.

14. The method of claim 10, wherein said amine component is selected from the group consisting of an L-amino acid, a C-protected L-amino acid, a D-amino acid, a C-protected D-amino acid, and an amine.

* * * * *